US012064826B2

(12) United States Patent
Simi et al.

(10) Patent No.: US 12,064,826 B2
(45) Date of Patent: Aug. 20, 2024

(54) MACHINING FIXTURE

(71) Applicant: MEDICAL MICROINSTRUMENTS, INC., Wilmington, DE (US)

(72) Inventors: Massimiliano Simi, Pisa (IT); Giuseppe Maria Prisco, Pisa (IT)

(73) Assignee: MEDICAL MICROINSTRUMENTS, INC., Wilmington, DE (US)

( * ) Notice: Subject to any disclaimer, the term of this patent is extended or adjusted under 35 U.S.C. 154(b) by 417 days.

(21) Appl. No.: 17/375,679

(22) Filed: Jul. 14, 2021

(65) Prior Publication Data

US 2021/0339328 A1 Nov. 4, 2021

Related U.S. Application Data

(63) Continuation of application No. 15/768,520, filed as application No. PCT/EP2016/074811 on Oct. 14, 2016, now Pat. No. 11,090,747.

(30) Foreign Application Priority Data

Oct. 16, 2015 (IT) .......................... 102015000062548

(51) Int. Cl.
*B23H 7/02* (2006.01)
*A61B 17/00* (2006.01)
(Continued)

(52) U.S. Cl.
CPC .............. *B23H 7/02* (2013.01); *A61B 17/00* (2013.01); *A61B 34/30* (2016.02); *A61B 34/71* (2016.02);
(Continued)

(58) Field of Classification Search
CPC ... A61B 34/30; A61B 34/71; A61B 2034/305; A61B 34/37; A61B 17/29;
(Continued)

(56) References Cited

U.S. PATENT DOCUMENTS 4,463,241 A * 7/1984 Smith .................. B23H 11/003
269/37
4,739,143 A 4/1988 Sakai et al.
(Continued)

FOREIGN PATENT DOCUMENTS

DE 39 39 078 C1 2/1990
FR 2 867 995 A1 9/2005
(Continued)

OTHER PUBLICATIONS

International Search Report and Written Opinion of the International Searching Authority for International Patent No. PCT/EP2016/074811 mailed Dec. 14, 2016, 8 pages.
(Continued)

*Primary Examiner* — Vy T Nguyen
(74) *Attorney, Agent, or Firm* — Merchant & Gould P.C.

(57) ABSTRACT

A method of manufacturing a jointed device of a medical instrument includes providing a machining fixture on a wire electrical discharge machine having an electrical discharge wire. The fixture includes member holes each adapted to accommodate at least one workpiece, the workpiece being adapted to form a portion of the jointed device of the medical instrument. At least two workpieces each include a first workpiece and a second workpiece, accommodated within at least two member holes of the member holes. The fixture is associated with the wire electrical discharge machine so that the electrical discharge wire can cut at most one workpiece at a time. The machining fixture is rotated around a fixture rotation axis at a predetermined angle, which is chosen to provide that the electrical discharge wire can cut only one workpiece at a time. The workpieces are cut by the electrical discharge wire.

15 Claims, 25 Drawing Sheets

Figure 1B:
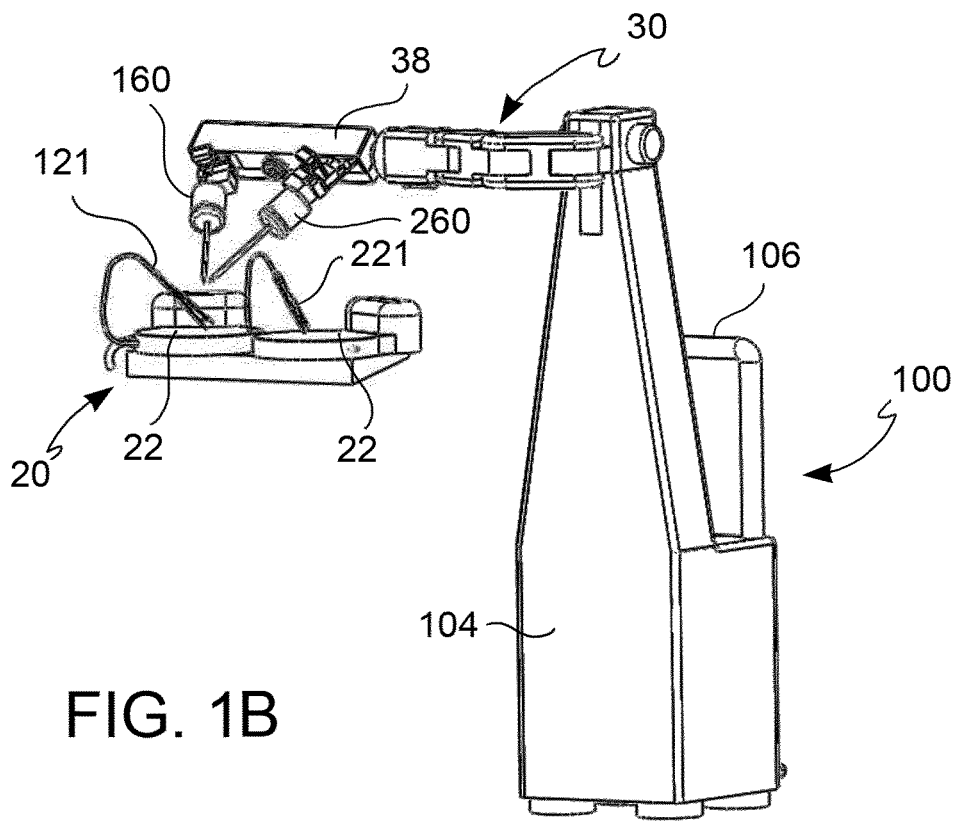

(51) Int. Cl.
*A61B 34/00* (2016.01)
*A61B 34/30* (2016.01)
*B23H 11/00* (2006.01)

(52) U.S. Cl.
CPC ............ *A61B 34/72* (2016.02); *B23H 11/003* (2013.01); *A61B 2017/00526* (2013.01); *A61B 2034/305* (2016.02); *B23H 2200/00* (2013.01)

(58) Field of Classification Search
CPC .. A61B 2017/00477; A61B 2017/2905; A61B 2034/301; A61B 2034/715; A61B 2017/2927; A61B 34/35; A61B 34/70; A61B 17/00; A61B 17/3421; A61B 17/3423; A61B 17/3431; A61B 17/3439; A61B 17/3474; A61B 1/00149; A61B 2017/00398; A61B 2017/00473; A61B 2017/00526; A61B 2017/00845; A61B 2017/2904; A61B 2017/2908; A61B 2017/2929; A61B 2017/2936; A61B 2017/3419; A61B 2017/3429; A61B 2017/3445; A61B 2017/3447; A61B 2017/3454; A61B 2017/3466; A61B 2034/2059; A61B 2034/2061; A61B 34/73; A61B 34/76; A61B 90/50; A61B 90/90; A61B 90/92; A61B 10/04; A61B 17/00234; A61B 17/0218; A61B 17/062; A61B 17/320016; A61B 17/3211; A61B 17/34; A61B 17/3462; A61B 17/3498; A61B 18/1445; A61B 1/00193; A61B 1/313; A61B 1/3132; A61B 2017/003; A61B 2017/00318; A61B 2017/00345; A61B 2017/00867; A61B 2017/0419; A61B 2017/2901; A61B 2017/291; A61B 2017/2932; A61B 2017/2938; A61B 2017/2939; A61B 2017/2948; A61B 2017/3441; A61B 2034/2048; A61B 2034/2051; A61B 2034/302; A61B 2034/306; A61B 2034/742; A61B 2090/061; A61B 2090/064; A61B 34/10; A61B 34/72; A61B 46/10; A61B 50/13; A61B 90/03; A61B 90/20; A61B 90/25; A61B 90/361; A61B 90/37; B25J 9/104; B25J 15/0028; B25J 15/0052; B25J 15/0286; B25J 17/02; B25J 17/025; B25J 3/04; B25J 9/1015; B25J 9/1045; B25J 9/1669; Y10S 901/29; Y10S 901/00; Y10S 901/15; Y10S 901/21; Y10S 901/36; Y10S 901/38; Y10S 901/39; Y10S 901/41; A61M 25/0041; A61M 25/0105; G05B 19/402; G05B 2219/45117; Y10T 74/20335
See application file for complete search history.

(56) References Cited

U.S. PATENT DOCUMENTS

| | | |
|---|---|---|
| 4,751,361 A | 6/1988 | Inoue et al. |
| 4,778,973 A | 10/1988 | Derighetti et al. |
| 4,960,971 A | 10/1990 | Kawanabe |
| 5,004,883 A | 4/1991 | Brown et al. |
| 5,315,087 A | 5/1994 | Itoh |
| 5,463,917 A | 11/1995 | Kothe |
| 5,981,895 A | 11/1999 | Grace et al. |
| 6,325,675 B1 | 12/2001 | Harmeyer |
| 6,371,952 B1 | 4/2002 | Madhani et al. |
| 6,394,998 B1 | 5/2002 | Wallace et al. |
| 6,768,076 B2 | 7/2004 | Walter |
| 7,155,316 B2 | 12/2006 | Sutherland et al. |
| 8,241,321 B2 | 8/2012 | Scheller et al. |
| 2001/0031983 A1 | 10/2001 | Brock et al. |
| 2002/0108226 A1 | 8/2002 | Miller |
| 2003/0213776 A1 | 11/2003 | Walter |
| 2004/0175541 A1 | 9/2004 | Smeenk et al. |
| 2009/0012571 A1 | 1/2009 | Perrow et al. |
| 2010/0011901 A1 | 1/2010 | Burbank |
| 2011/0196419 A1 | 8/2011 | Cooper |
| 2013/0046317 A1 | 2/2013 | Blumenkranz |
| 2013/0110289 A1 | 5/2013 | Cho et al. |
| 2017/0072490 A1 | 3/2017 | Hamada et al. |

FOREIGN PATENT DOCUMENTS

| | | |
|---|---|---|
| GB | 814 202 A | 6/1959 |
| WO | 2010/005657 A2 | 1/2010 |
| WO | 2010/009221 A2 | 1/2010 |

OTHER PUBLICATIONS

Extended European Search Report for corresponding European Patent Application No. 19190094.3 mailed Nov. 28, 2019, 9 pages.

* cited by examiner

MACHINING FIXTURE

This application is a Continuation of U.S. patent application Ser. No. 15/768,520, filed 13 Apr. 2018, which is a National Stage Application of PCT/EP2016/074811, filed 14 Oct. 2016, which claims benefit of Serial No. 102015000062548, filed 16 Oct. 2015 in Italy and which applications are incorporated herein by reference. To the extent appropriate, a claim of priority is made to each of the above-disclosed applications.

FIELD OF INVENTION

The present invention relates to a method of manufacturing for a medical instrument.

In particular, the present invention relates to a method of manufacturing for a medical instrument comprising a jointed device.

STATE-OF-THE-ART

Robotic assemblies for surgery or microsurgery comprising multi joint robotic arms terminating with surgical instruments are known in the field. For instance, document US-71553116-B2 discloses a robotic assembly for performing brain microsurgery under MRI (Magnetic Resonance Imaging).

The adoption of robotic technologies can bring about great benefits, allowing both a high degree of miniaturization of the instruments and scaling the size of the movements in the operating field, hence eliminating the effect of physiological tremor and easing the manual task. For example, microsurgical procedures are carried out in several phases of the reconstruction of biological tissues, such as for example in the execution of blood vessel anastomosis, comprising small diameter vessels, and nerves. Such procedures are carried out to reconstruct anatomy after the occurrence of traumatic lesions or of lesions produced by surgical removal of tissue, to reattach limbs and to revascularize tissues, all performed in an open surgery set-up given the pre-existence of a superficial lesion. Others examples of application of microsurgical techniques are found in transplant surgery, neurosurgery or in vascular surgery, as well as in surgery around and inside the eye, and in the inner ear, as in the case of cochlear implants. Also the prominent surgical procedure of cardiac by-pass comprises the critical step of anastomosis of the coronary arteries. The need for instrument miniaturization is also felt in other surgical techniques, for example in minimal invasive surgery, such as laparoscopy and endoscopy, that are aimed at limiting the invasiveness of surgical instruments on biological tissue. With reference to laparoscopy, the technical solutions known in the art do not allow a satisfactory miniaturization of the diameter of the laparoscopic instruments employed in Single Incision Laparoscopic Surgery or Single Port Surgery. Moreover, it is worth noticing that the endoscopes typically employed in MIS have an instrument channel with a diameter between 1 mm and 3.2 mm. Such dimensions limit the functionality of current surgical instrumentation available through the endoscope instrument channel, which at present is typically just capable of gripping action.

Medical instruments comprising a jointed device suitable to work on the patient, are generally known in the art. For example, document WO-2010-009221-A2 shows a robotic surgical instrument comprising a distally jointed device, capable of providing three degrees of freedom of motion, respectively pitch, yaw and grip, employing just four actuation cables. Such cables slide inside guiding channels, or sheaths, present inside the body of the articulating device. Said technical solution limits the miniaturization of the robotic articulating device, because friction between the guiding channels surfaces and the cables that slide inside them limits the positioning precision achievable by the articulating device.

As it is known in the art, as the physical dimensions of a medical instruments are reduced, difficulties arise which are related to the increase of relevance of superficial forces, such as friction, that become dominant over volume forces. Such a phenomenon requires to resort to solutions that minimize friction forces, and at the same time reduce lost motions of mechanics to a minimum. The loss of positioning precision of an articulating device is a fundamental technological obstacle to further miniaturization of articulating instrument, since, with miniaturization, also the stiffness of the driving members (tendons) goes down with the second power of their diameter, making it even more difficult to overcome friction for the precise positioning of the instrument tip. Moreover such a solution requires a tendon guiding system comprising channels and guiding surfaces that surround the cables that make the pitch and yaw links, as well as the instrument shaft, very difficult to miniaturize using known fabrication methods, such as for example injection molding and machining, and would be prone to have several locations of mechanical weakness.

Further examples of actuation cables for surgical instruments suited to slide, when pulled or pushed, inside sheaths or guiding channels, for example obtained on the lateral surfaces of pulleys, are disclosed in documents U.S. Pat. Nos. 6,371,952-B1, 6,394,998-B1 and WO-2010-005657-A2. Specifically, the latter document discloses a solution where actuation cables follow trajectories that cross as they go around pulleys that comprise guiding channels to avoid that such cables interfere with one another, a condition that limits their efficacy in transmitting motion to the articulating device, such as for instance in case of bundling up or sliding of one tendon onto another one.

A further obstacle to the miniaturization of jointed or articulated devices is the challenge of fabricating and assembling three dimensional micromechanical parts with sufficient precision at a reasonable process cost. The need to develop relatively high forces at the tip in devices with a sub-millimeter size suggests the use extremely rigid metals for such components, such as for example tool steel.

It is known that biomedical devices are generally fabricated using fabrication techniques derived from the micro-electronic industry. For example, laser or water-jet cutting is not appropriate for fast machining in three dimensions. Injection molding does not currently produce sufficiently high tolerance parts. In contrast, electrical discharge machining (EDM) are capable of producing satisfactory performance both in terms of surface finishing and with respect to the geometric tolerance required by the mechanical designs. EDM generally entails a slow and expensive process. For example, the document U.S. Pat. No. 6,768,076-B2 discloses a fixture for EDM able to support pieces to be cut in a single plane.

Nevertheless the fixture is not suitable for repeated placement of the piece, for example it is not possible to rotate the fixture while it is being machined in a way that the EDM can work in multiple cutting planes, resulting in a laborious fabrication process that necessitates complex operations of recalibration every time a cut is carried out in a different plane. This results in a loss of precision and hence less precise dimensional and geometric tolerances.

Hence there is a felt need to provide a jointed or articulated medical instrument, or an assembly comprising an jointed or articulated device, which is structurally and functionally suitable for extreme miniaturization without compromising its reliability and safety. There is also a felt need to provide a jointed or articulated medical instrument, or an assembly comprising a jointed device, suitable for carrying out a wide variety of medical-surgical therapies. Finally, there is a felt need to provide a jointed or articulated medical instrument, or an assembly comprising an jointed or articulated device, that is durable and able to undergo periodic maintenance without compromising its sterility or reliability.

There is a felt need to provide a jointed or articulated medical instrument, or an assembly comprising a jointed device, that requires simplified manufacturing compared to known solutions.

There is a felt need to provide a fabrication method of said medical instrument that is more efficient with respect to known solutions and that guarantees the required level of precision for the assembly.

There is a felt need to provide a manufacturing method for a medical instrument that guarantees a faster machining process, without compromising precision in production.

Furthermore, there is a felt need to provide a method of fabrication suitable for producing parts subject to extreme miniaturization without reducing neither the precision of detailed manufacturing nor the ease of assembly of the parts produced.

Are known solutions for cutting a plurality of pieces by means of a wire electro-discharge machining. For example, document FR-2867995-A1 shows a solution of cutting simultaneously a number of identical pieces of a glass frame, wherein each of said pieces can rotate around its longitudinal axis, during machining. The pieces produced by means of this solution are identical for each cut, therefore this solution is unsuitable to cut pieces to be joined to each other and having high surface finishing, therefore this solution in unsuitable for providing pieces to be joined to each other of micrometrical size with an acceptable degree of tolerance. For example, document DE-3939078-C1 also shows a similar solution.

For example, document GB-814202-A shows a wire electro discharge machine having a plurality of cutting wires which perform holes in a plurality of workpieces mounted on a annular machining fixture.

For example, document U.S. Pat. No. 5,004,883-A shows a wire electro discharge machining process of cutting the same workpiece along two orthogonal cutting planes. Although satisfactory under some point of views, this solution force long time of manufacturing for a single workpiece.

For example, document U.S. Pat. No. 4,463,241-A shows a wire electro discharge machine having a machining fixture suitable to host a plurality of workpieces for performing a cut in a single cutting plane to produce workpieces of different shapes.

It is felt the need of producing workpieces suitable to joint to each other with a higher degree of precision, avoiding to raise the machining time.

It is felt the need of providing a wire electro discharge machining method of manufacturing a plurality of workpieces with an higher degree of precision, suitable for applications at the microscale.

It is felt the need of providing a machining fixture for a wire electro discharge machine suitable to host a plurality of workpieces during machining, and at the same time suitable to allow successive cuts on different cutting planes.

Solution

One of the goals of the invention described here is to overcome the limitations of known solutions described above and to provide a solution to the needs mentioned with reference to the state of the art.

FIGURES

Figure 1A:
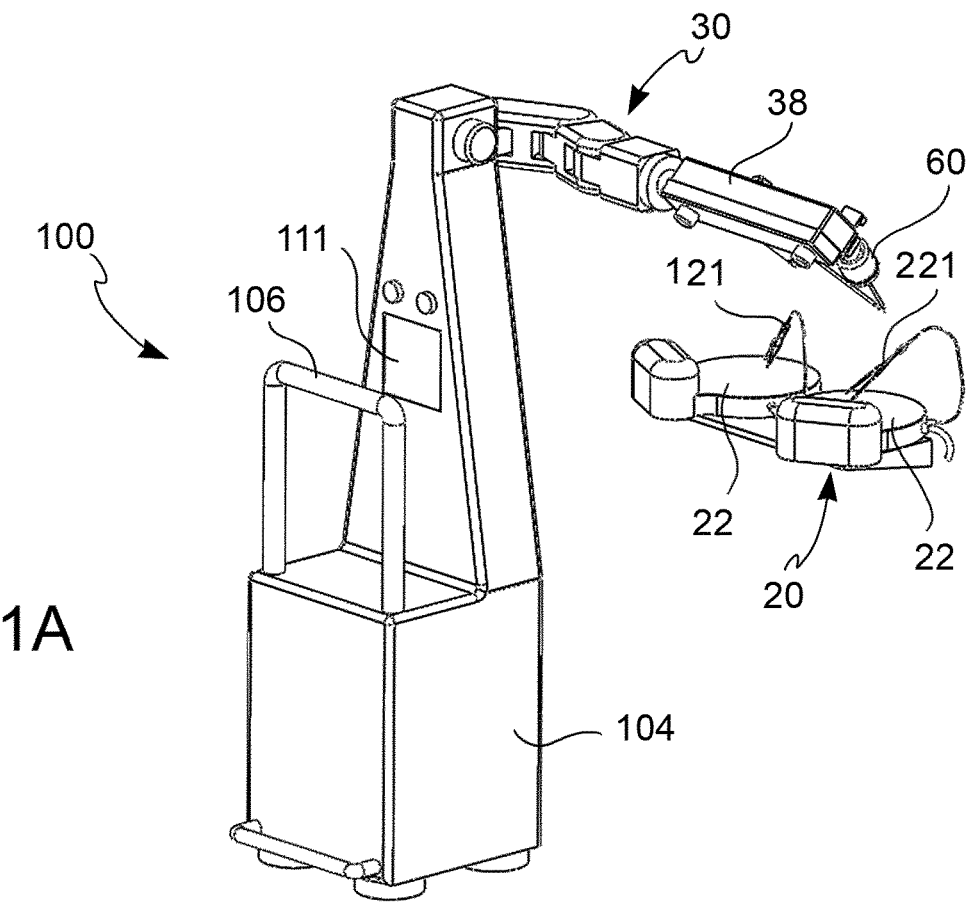
Figure 1C:
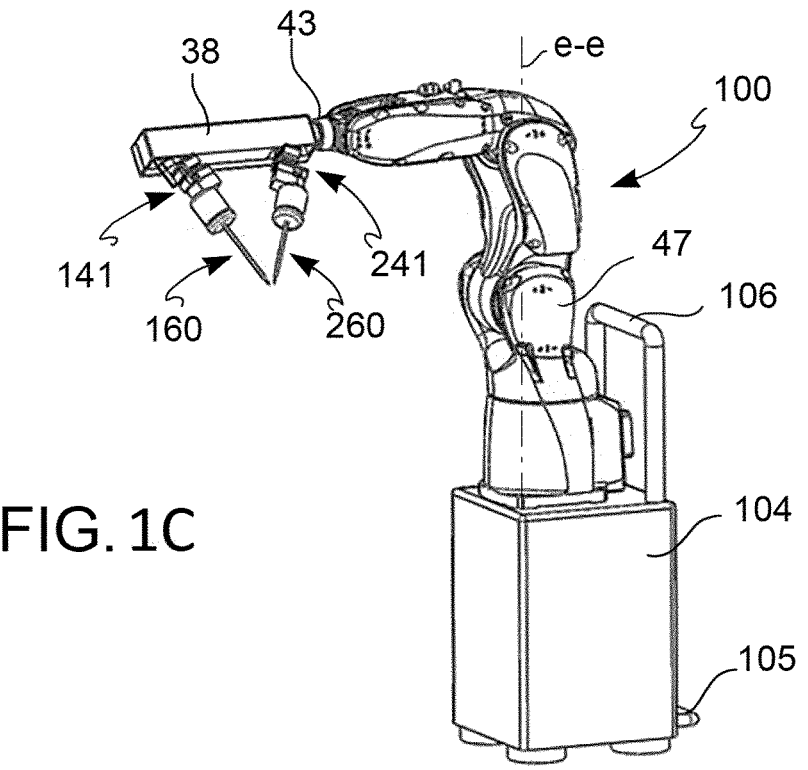
Figure 2A:
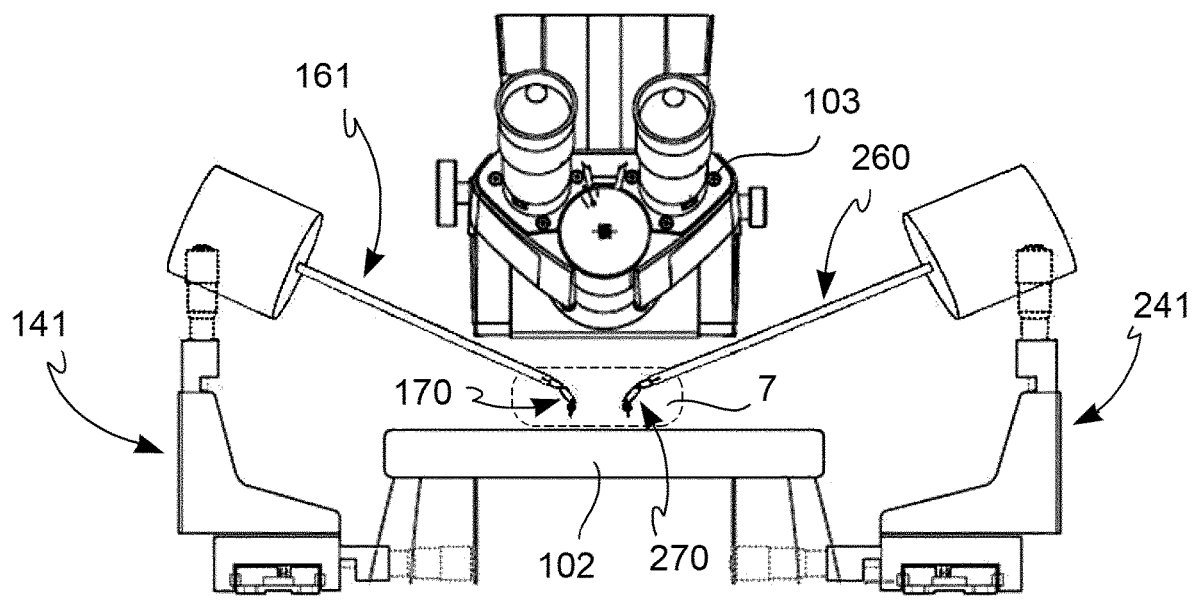
Figure 2B:
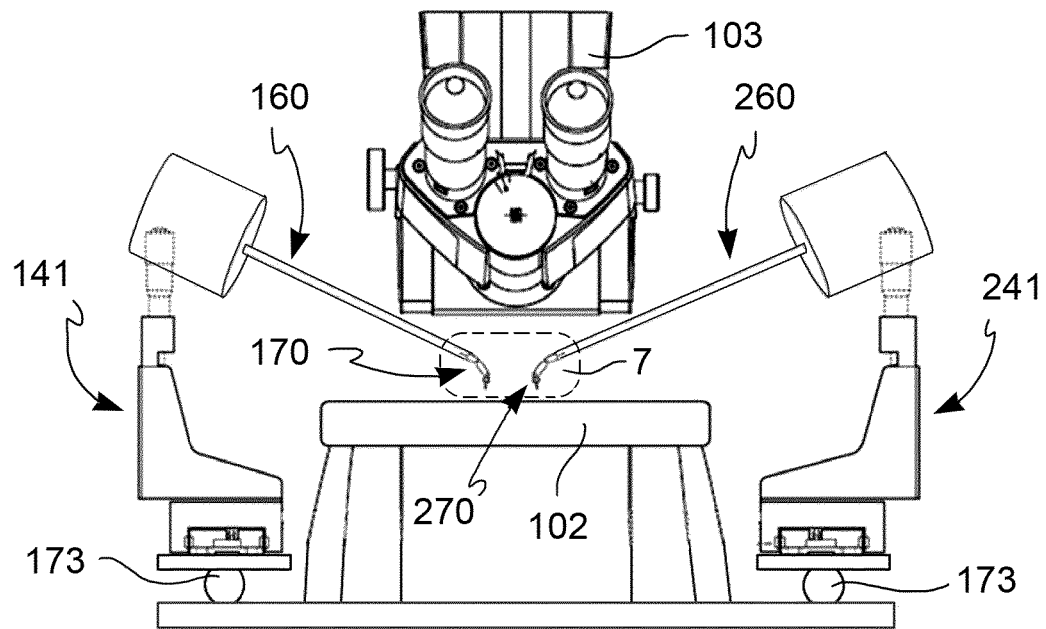
Figure 3:
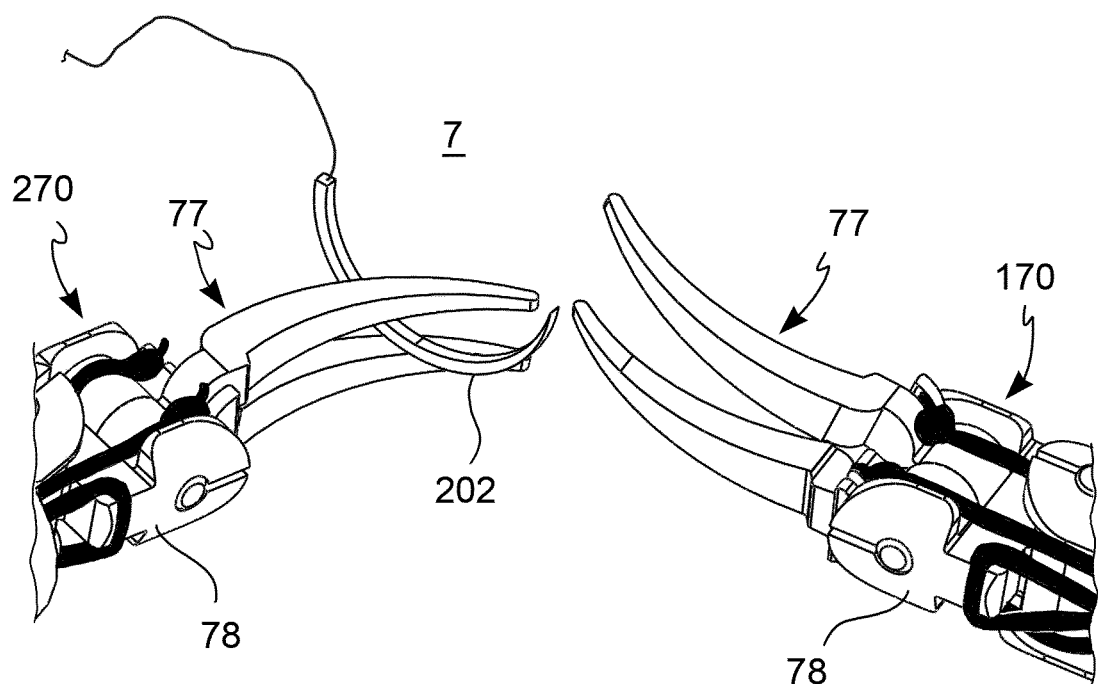
Figure 4B:
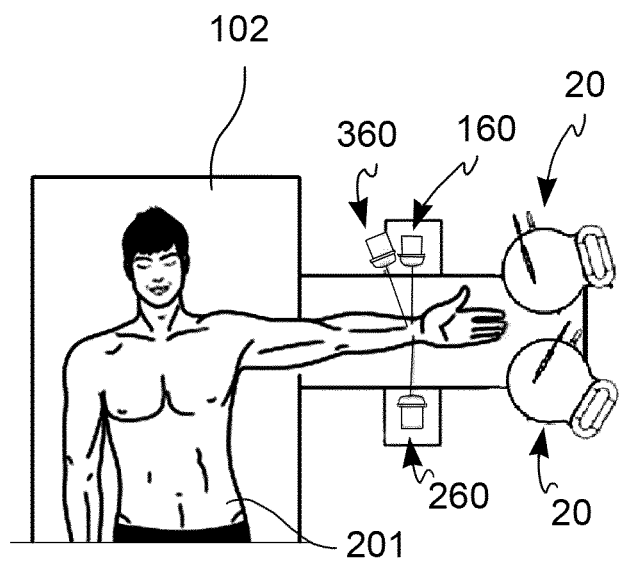
Figure 4A:
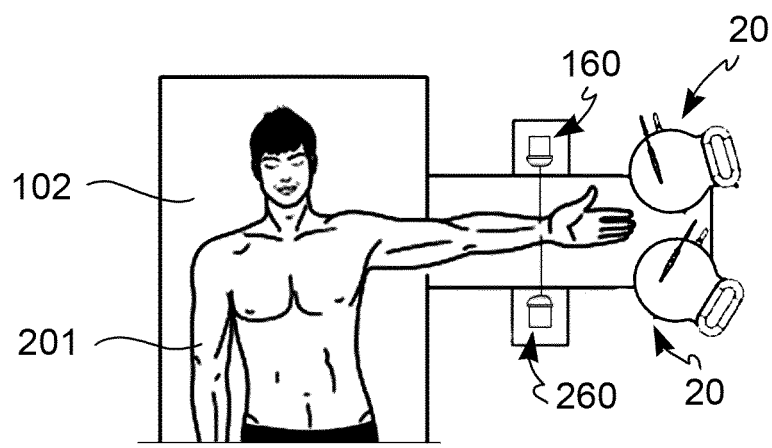
Figure 5:
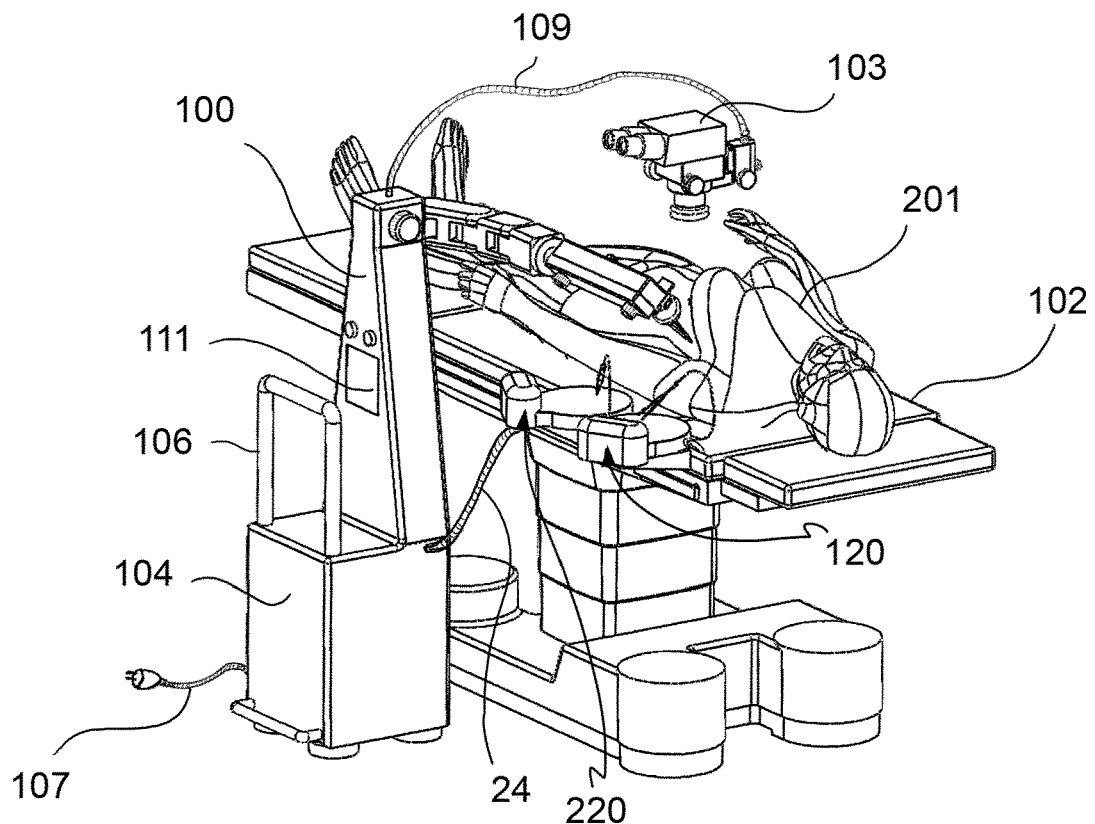
Figure 6:
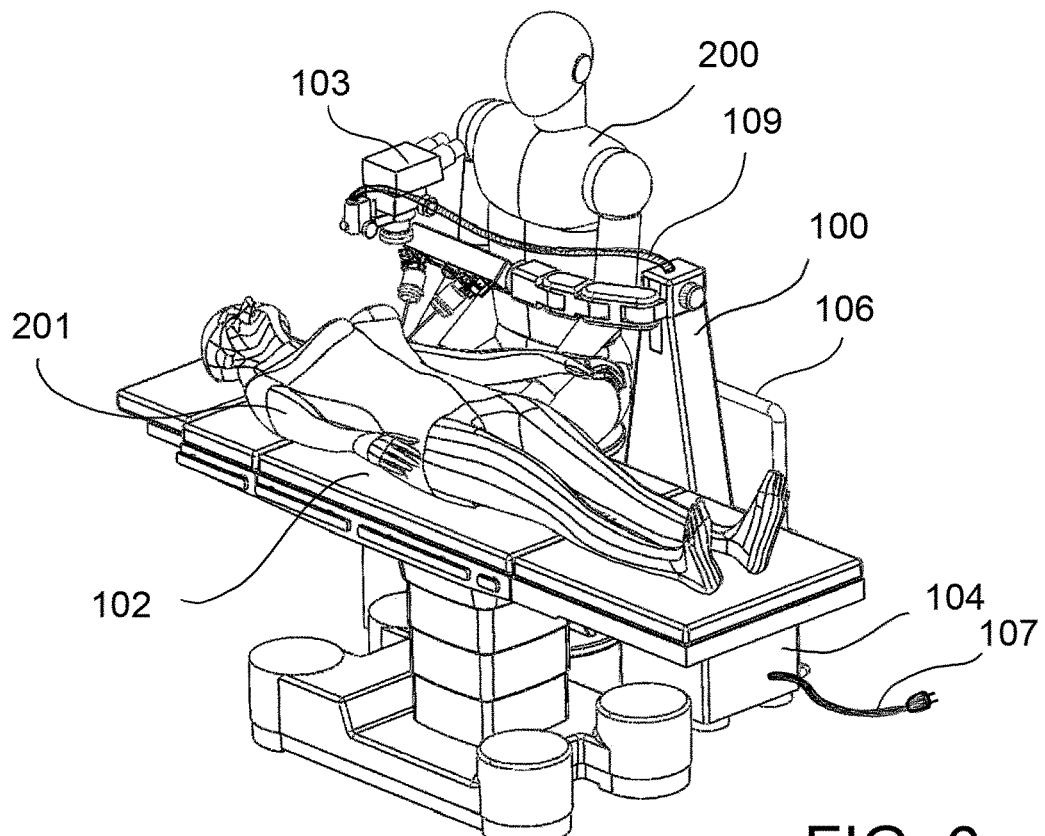
Figure 7:
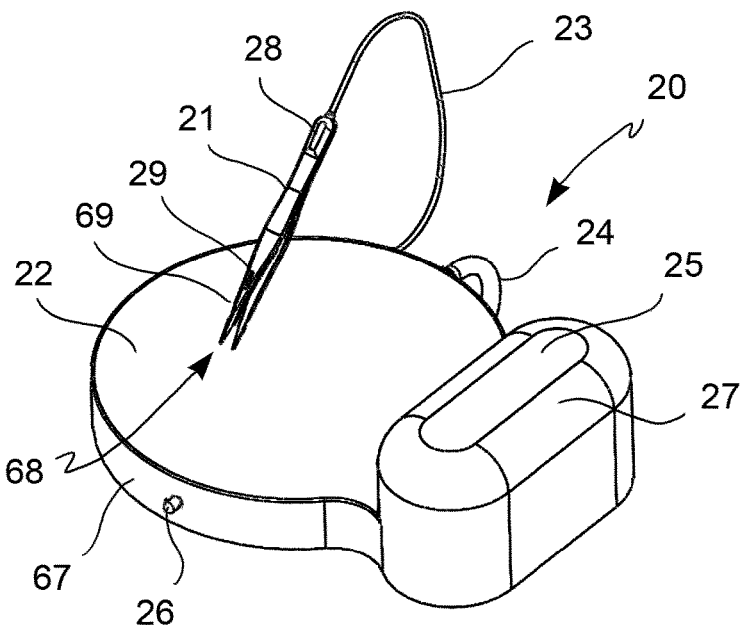
Figure 8:
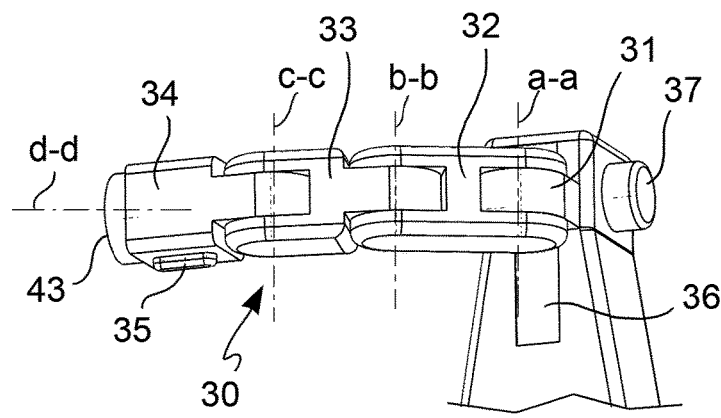
Figure 9A:
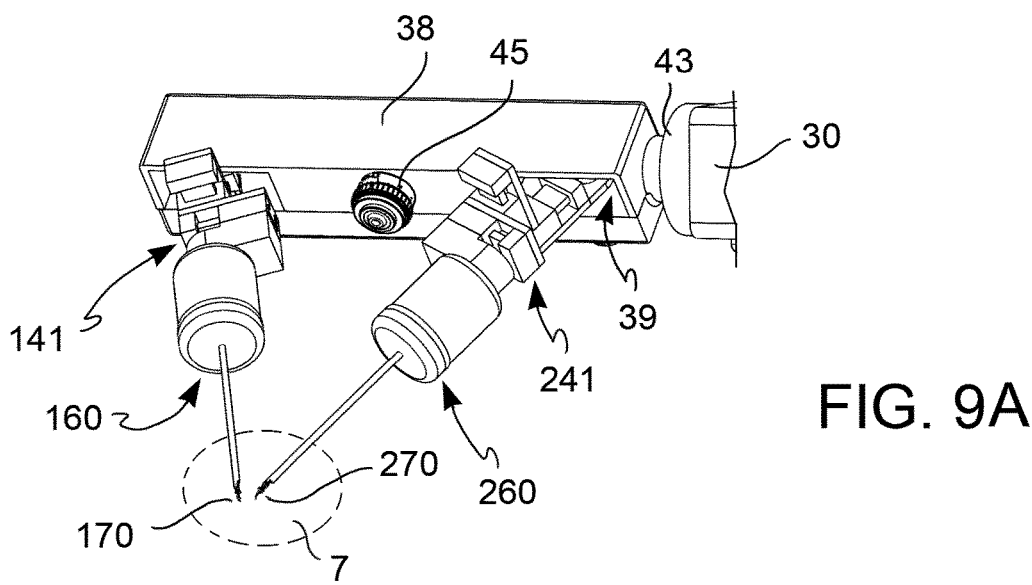
Figure 9B:
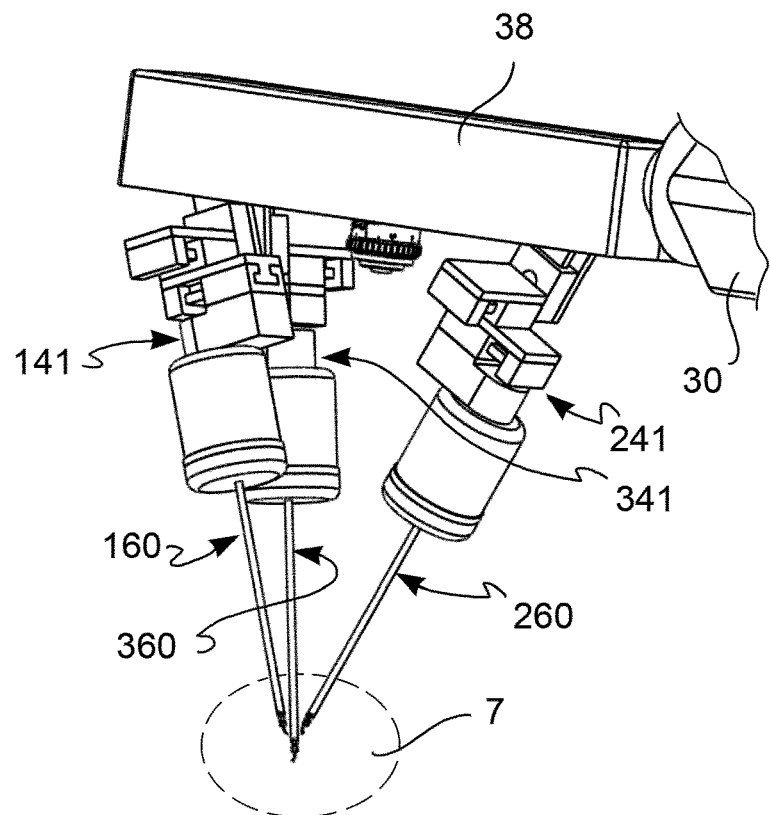
Figure 9C:
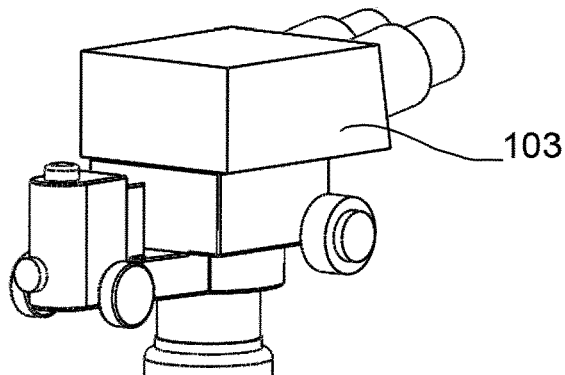
Figure 9C:
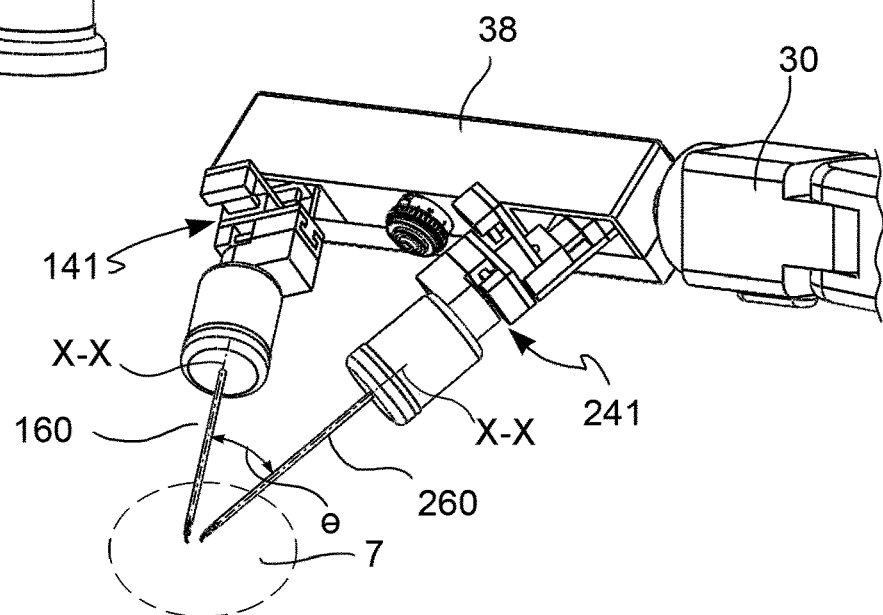
Figure 9D:
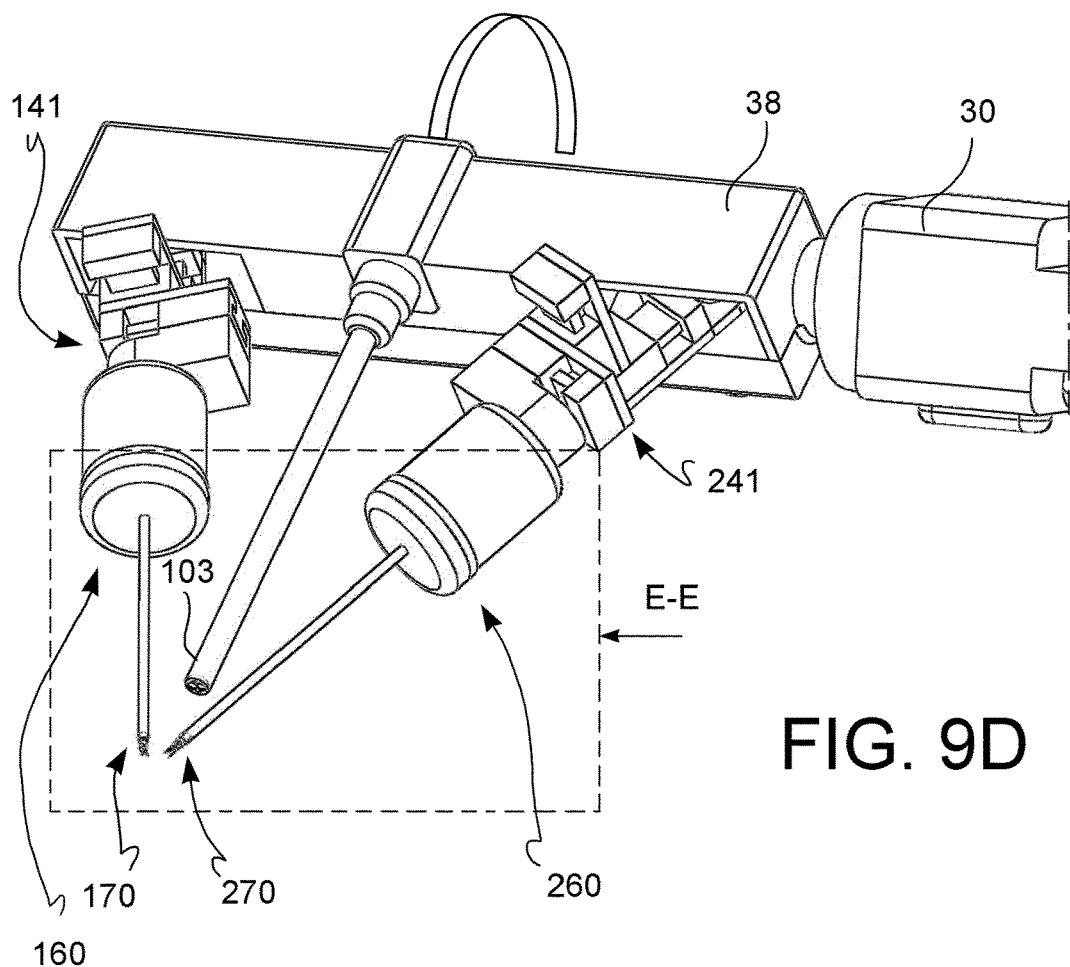
Figure 9E:
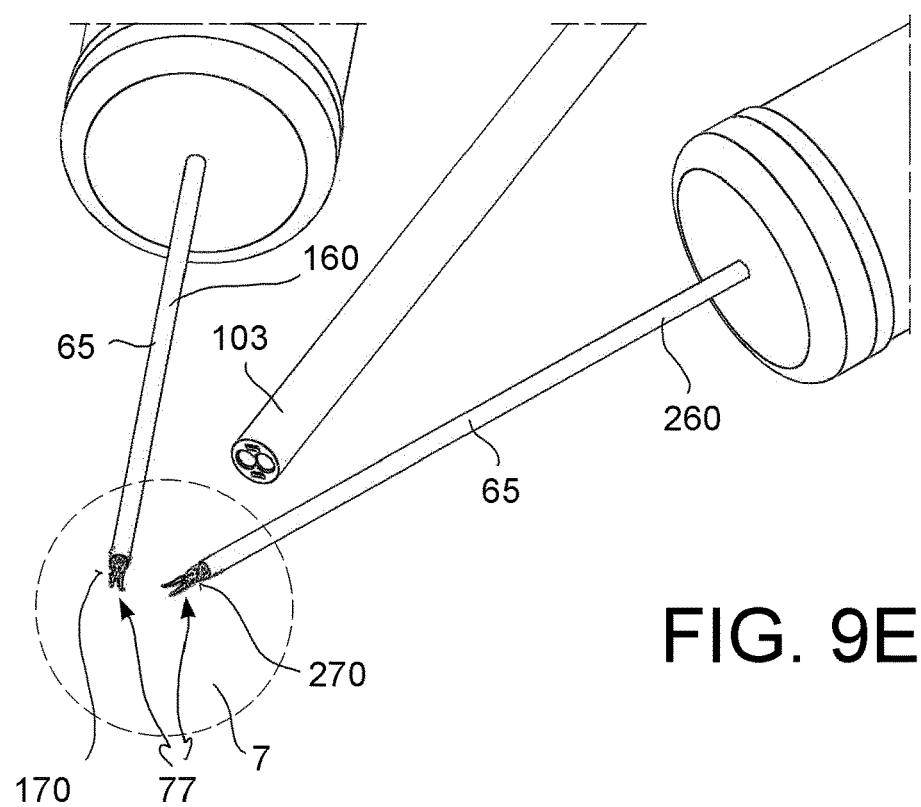
Figure 10:
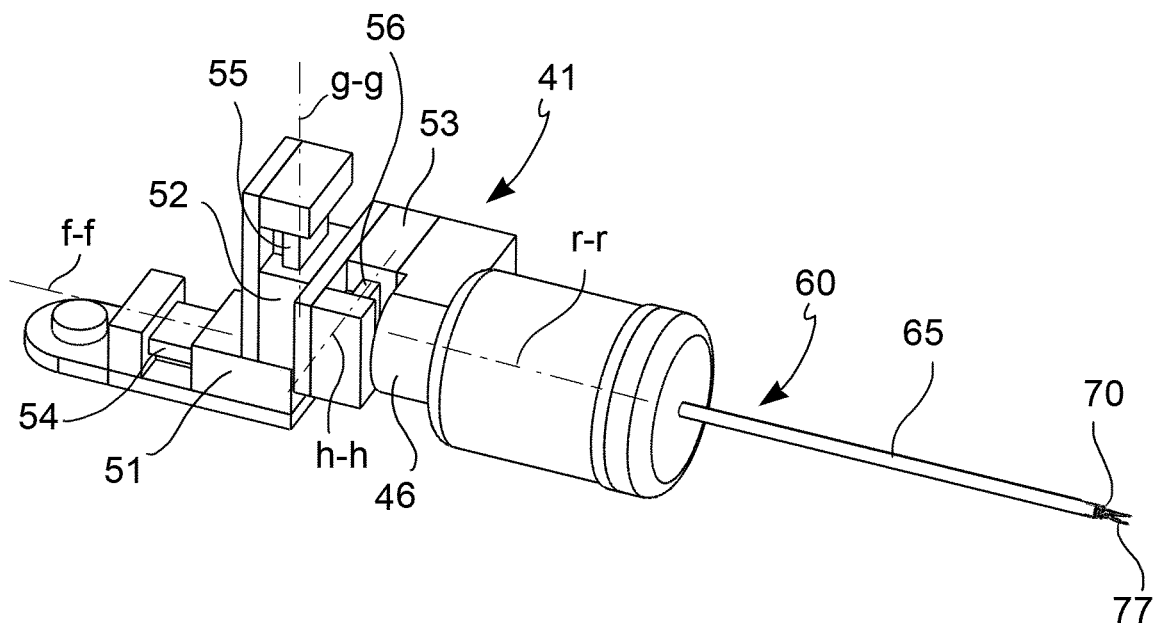
Figure 11:
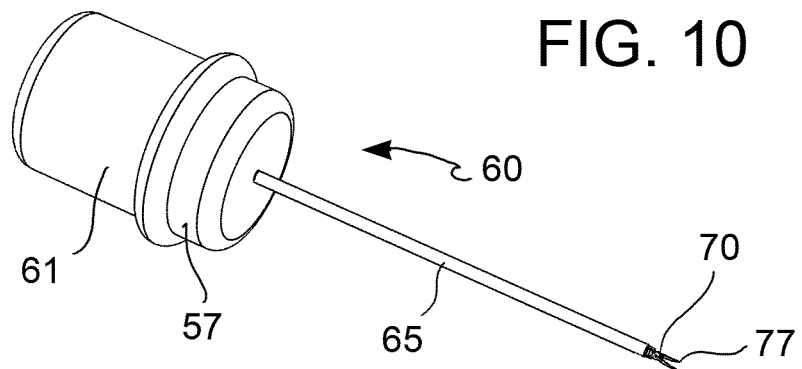
Figure 12:
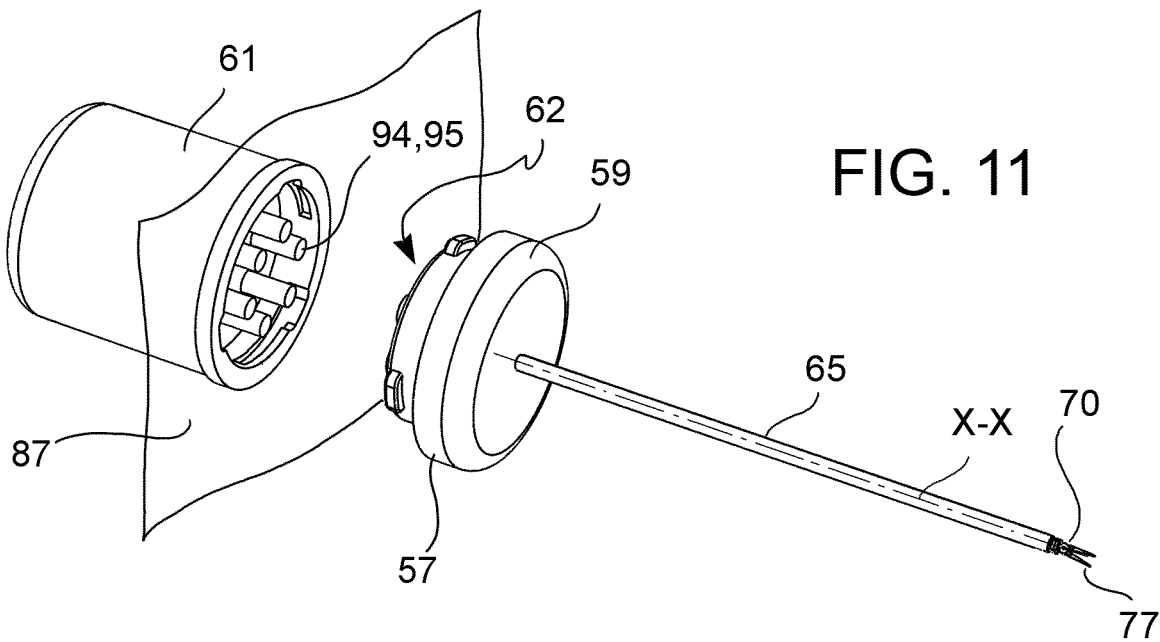
Figure 13A:
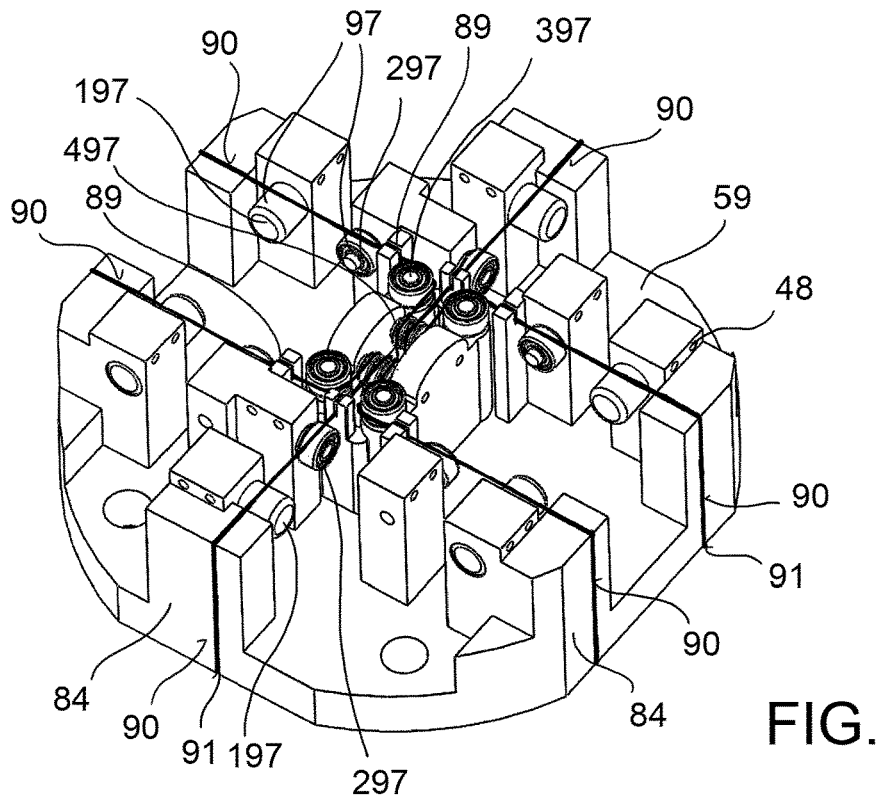
Figure 14A:
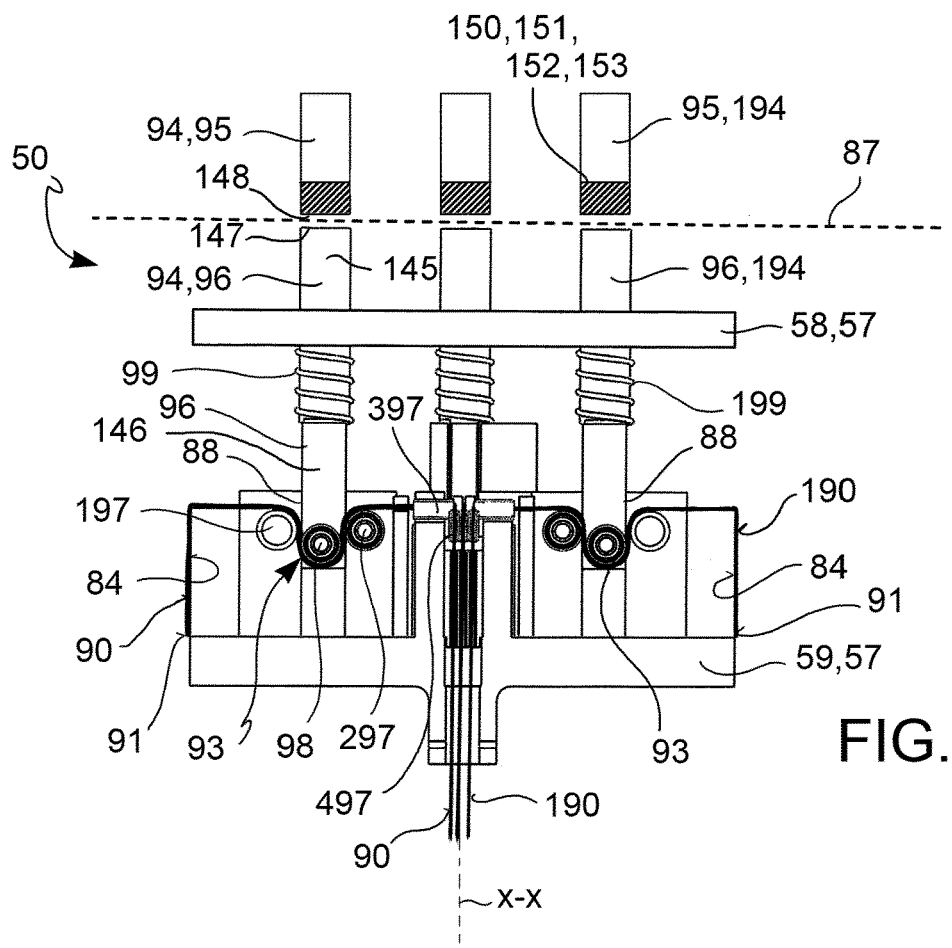
Figure 35:
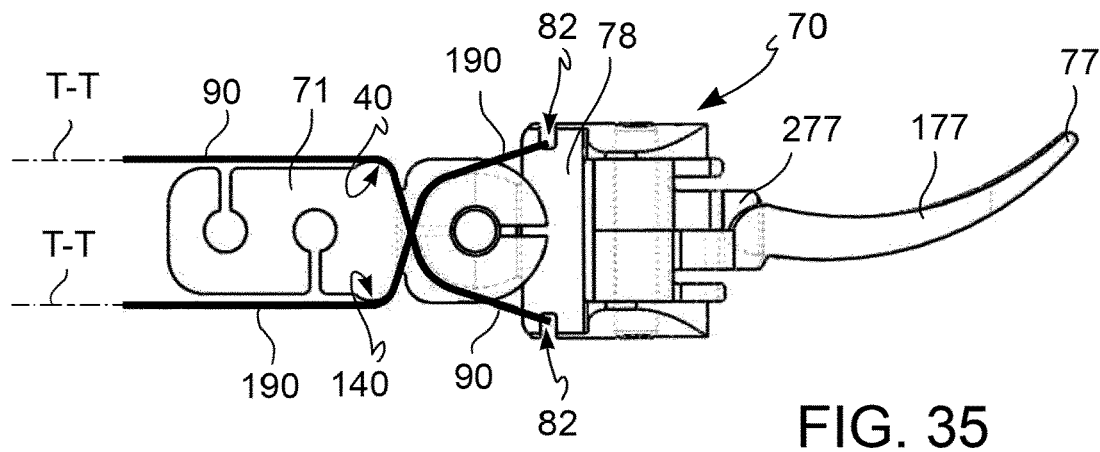
Figure 36:
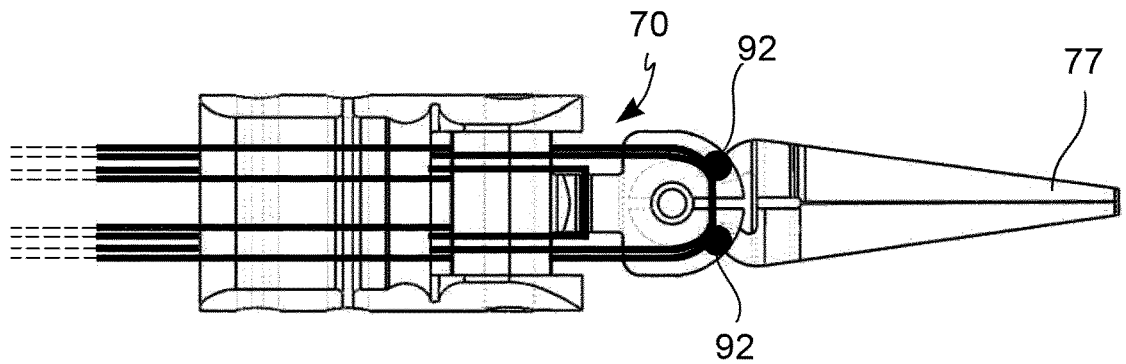
Figure 13B:
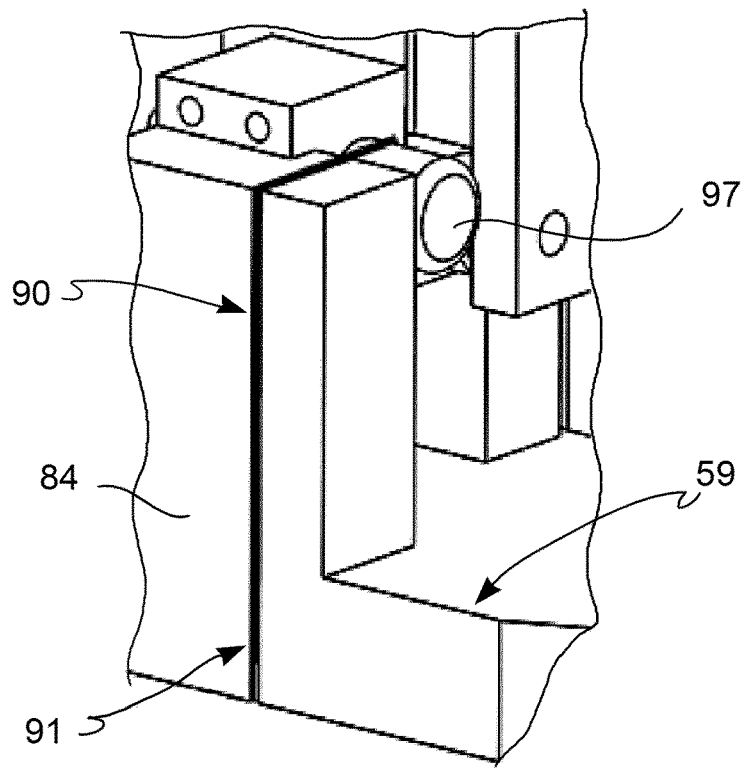
Figure 14B:
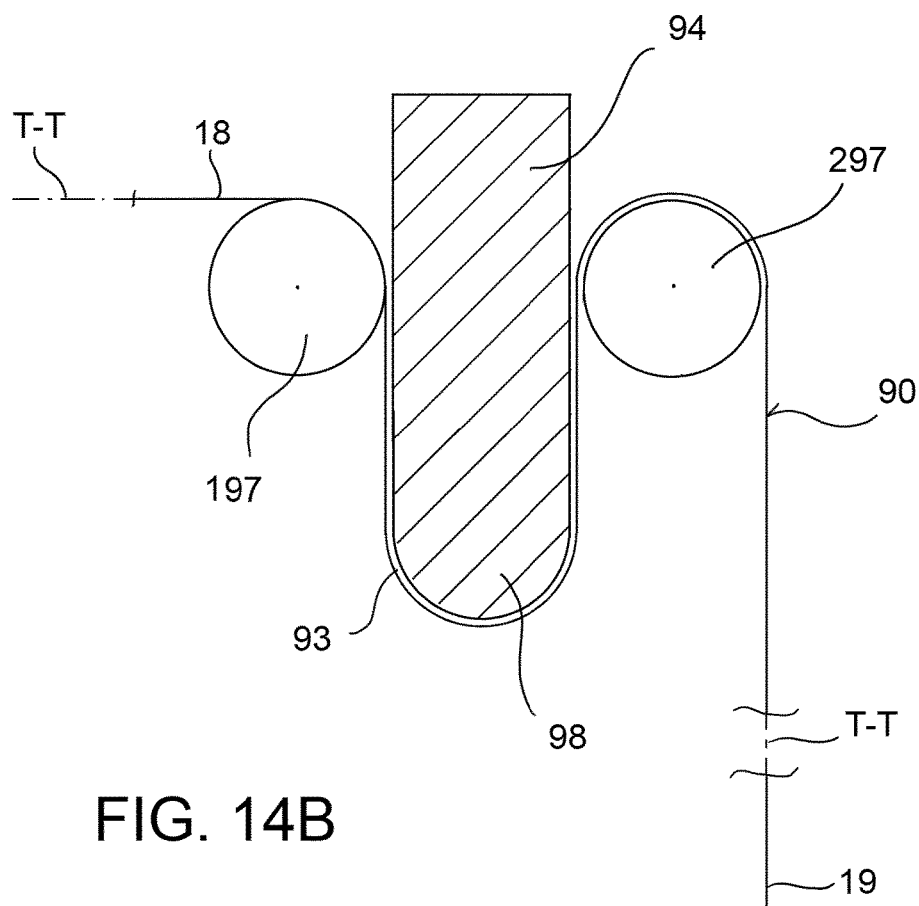

Further characteristics and advantages of the invention will appear from the description reported below of preferred embodiments, which are given as examples and are not meant to be limiting, which makes reference to the attached figures, in which:

the FIG. 1A is a perspective view, which shows the surgical robotic assembly;

the FIG. 1B is a perspective view, which shows the surgical robotic assembly;

the FIG. 1C is a perspective view, which shows a surgical robotic assembly;

the FIG. 2A is a perspective view, which shows a surgical robotic assembly associated with other elements of the operating room;

the FIG. 2B is a frontal view, which shows a surgical robotic assembly associated with other elements of the operating room;

the FIG. 3 is a perspective view, which shows a portion of a couple of jointed or articulated devices.

the FIG. 4A is a view from above, which shows a portion of a surgical robotic assembly associated with other elements of the operating room and a patient.

the FIG. 4B is a top view, which shows a portion of a surgical robotic assembly associated with other elements of the operating room and a patient.

the FIG. 5 is a perspective view, which shows a portion of a surgical robotic assembly associated with other elements of the operating room and a patient.

the FIG. 6 is a perspective view, which shows a portion of a surgical robotic assembly associated with other elements of the operating room, the surgeon and a patient.

the FIG. 7 is a perspective view, which shows a control device.

the FIG. 8 is a perspective view, which shows a macro-positioning arm.

the FIG. 9A is a perspective view, which shows a portion of a robotic assembly.

the FIG. 9B is a perspective view, which shows a portion of a robotic assembly.

the FIG. 9C is a perspective view, which shows a portion of a robotic assembly, associated with a microscope.

the FIG. 9D is a perspective view, which shows a portion of a robotic assembly, associated with an endoscope.

the FIG. 9E is an enlarged view of the detail indicated with the arrow E-E of FIG. 9C.

the FIG. 10 is a perspective view, which shows a portion of a robotic assembly.

the FIG. 11 is a perspective view, which shows a medical instrument.

the FIG. 12 is a perspective view, and a depiction of separate parts, which shows a medical instrument.

the FIGS. 13A and 13B show, in a perspective view, portions of a driving system.

the FIG. 14A is a schematic section view of a portion of a driving system.

the FIG. 14B is a schematic section view of a portion of a driving system.

Figure 15A:
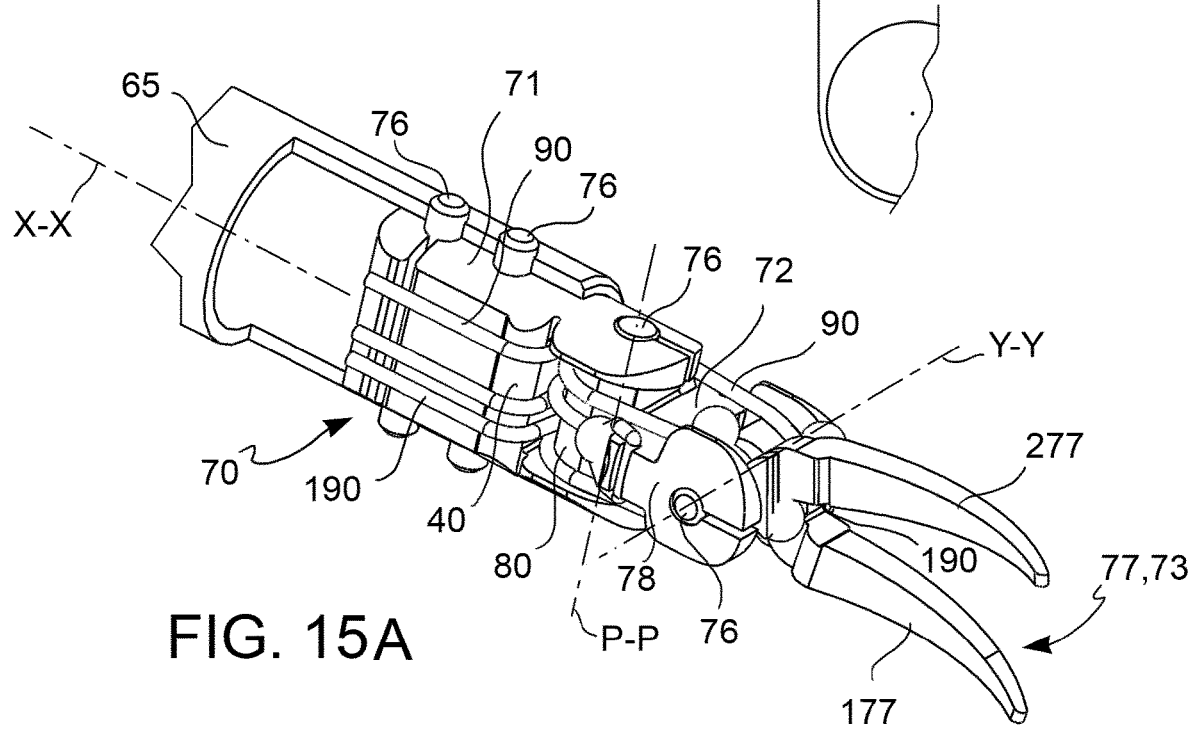
Figure 16:
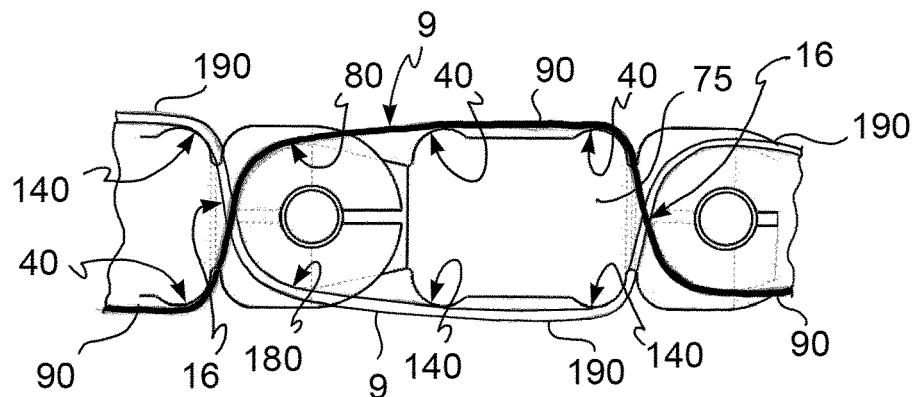
Figure 17:
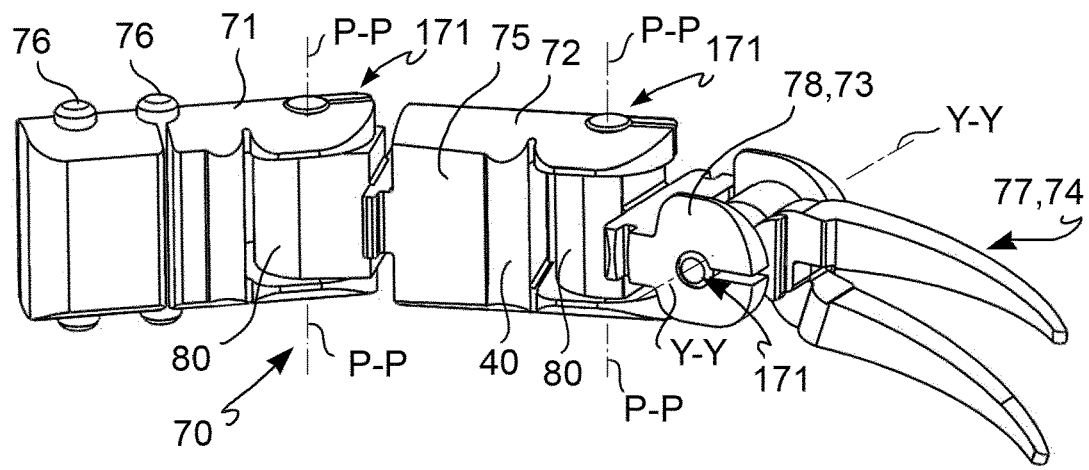
Figure 15B:
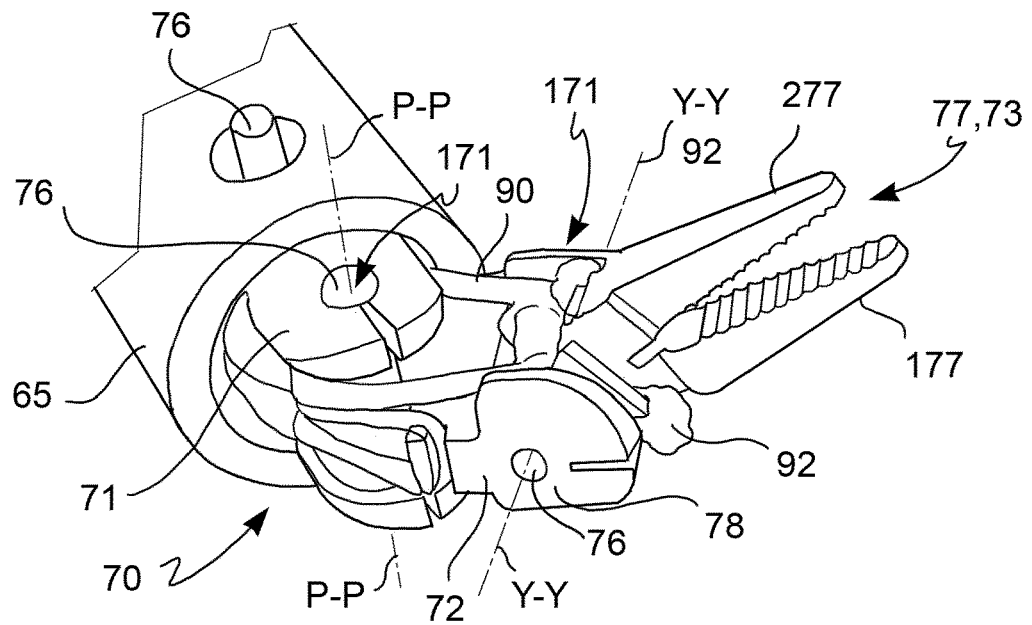
Figure 15C:
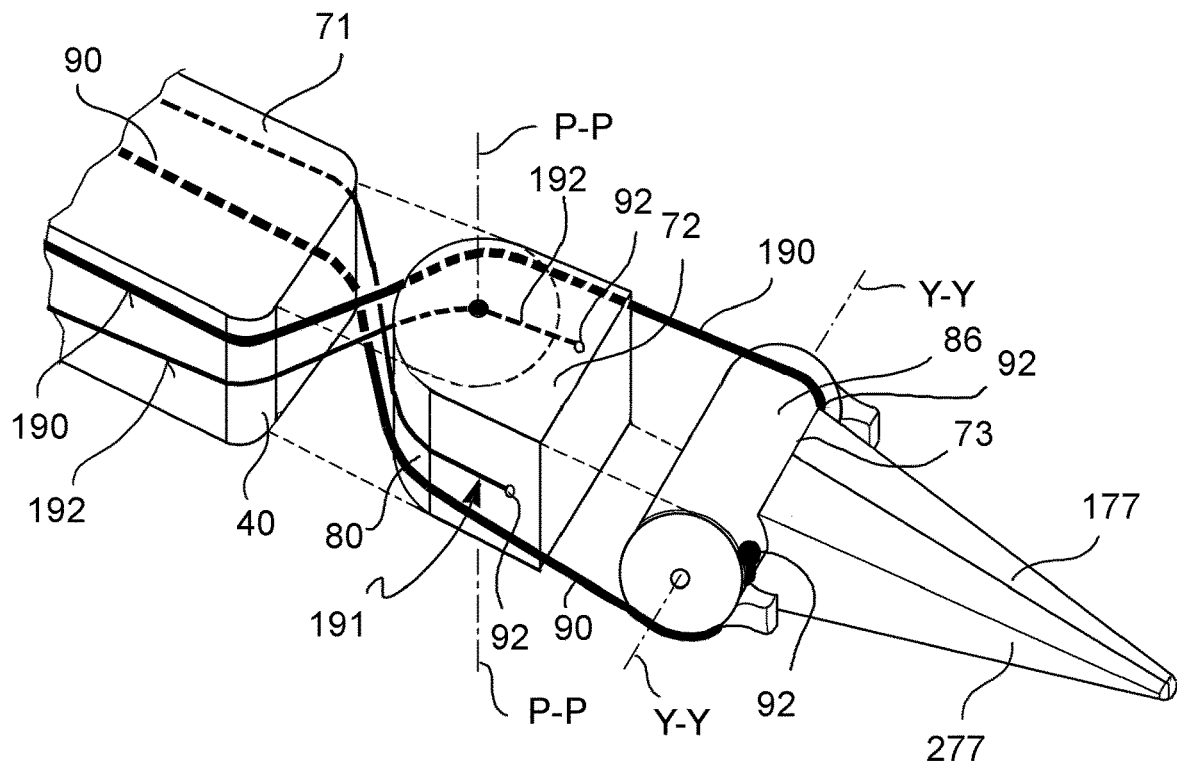
Figure 15D:
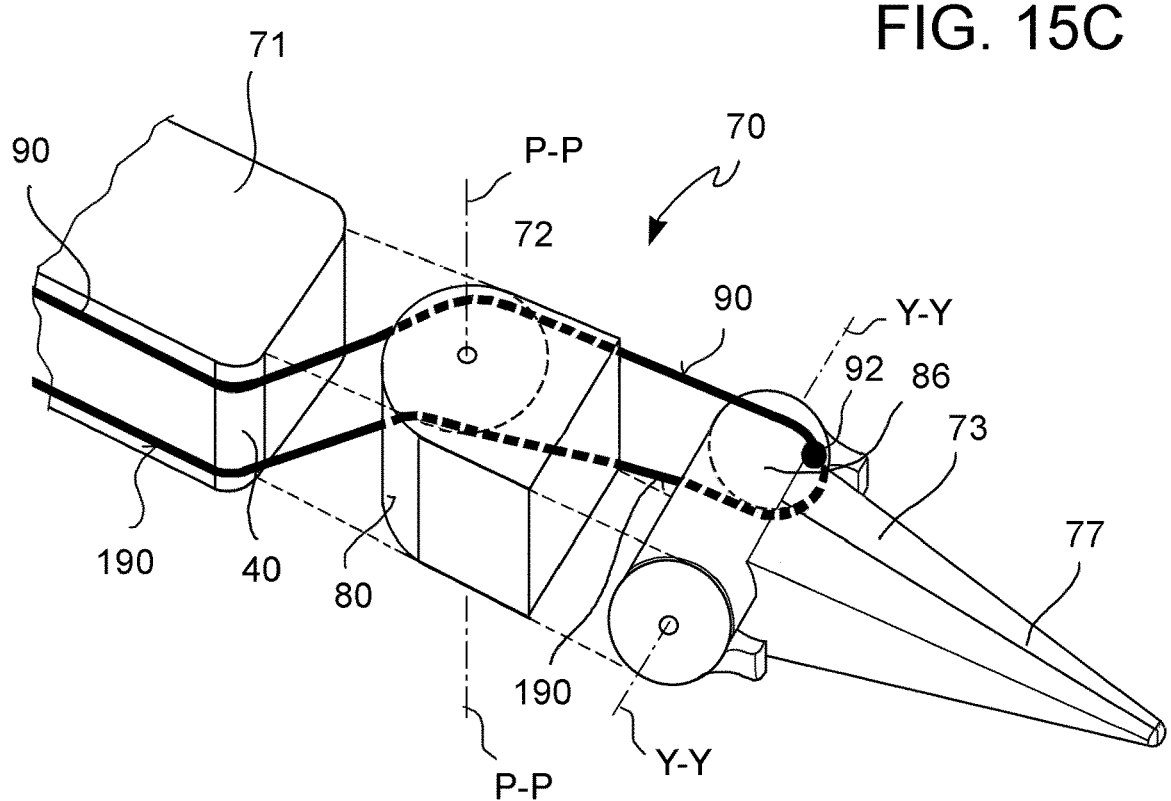
Figures 18, 19:
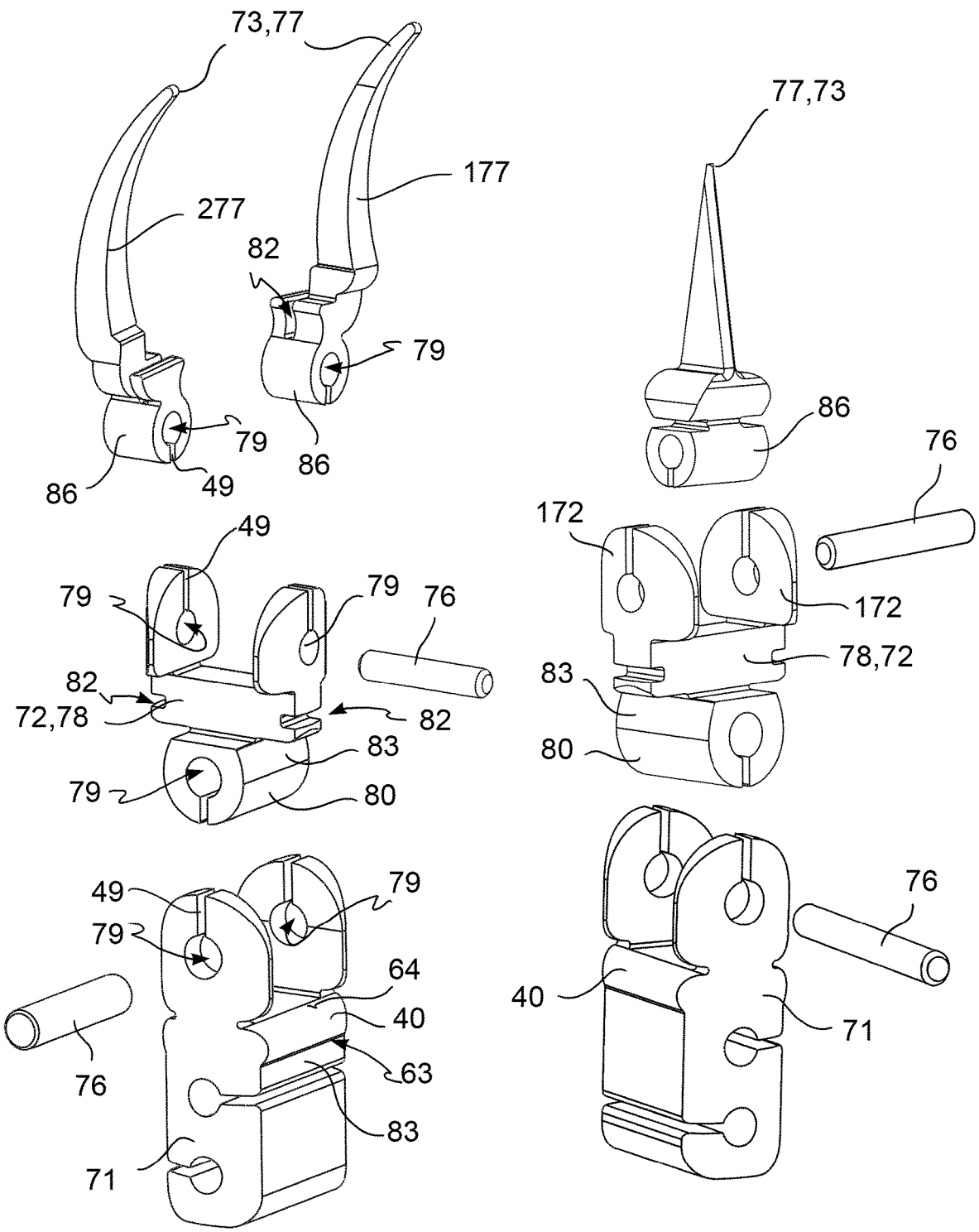
Figures 20, 21:
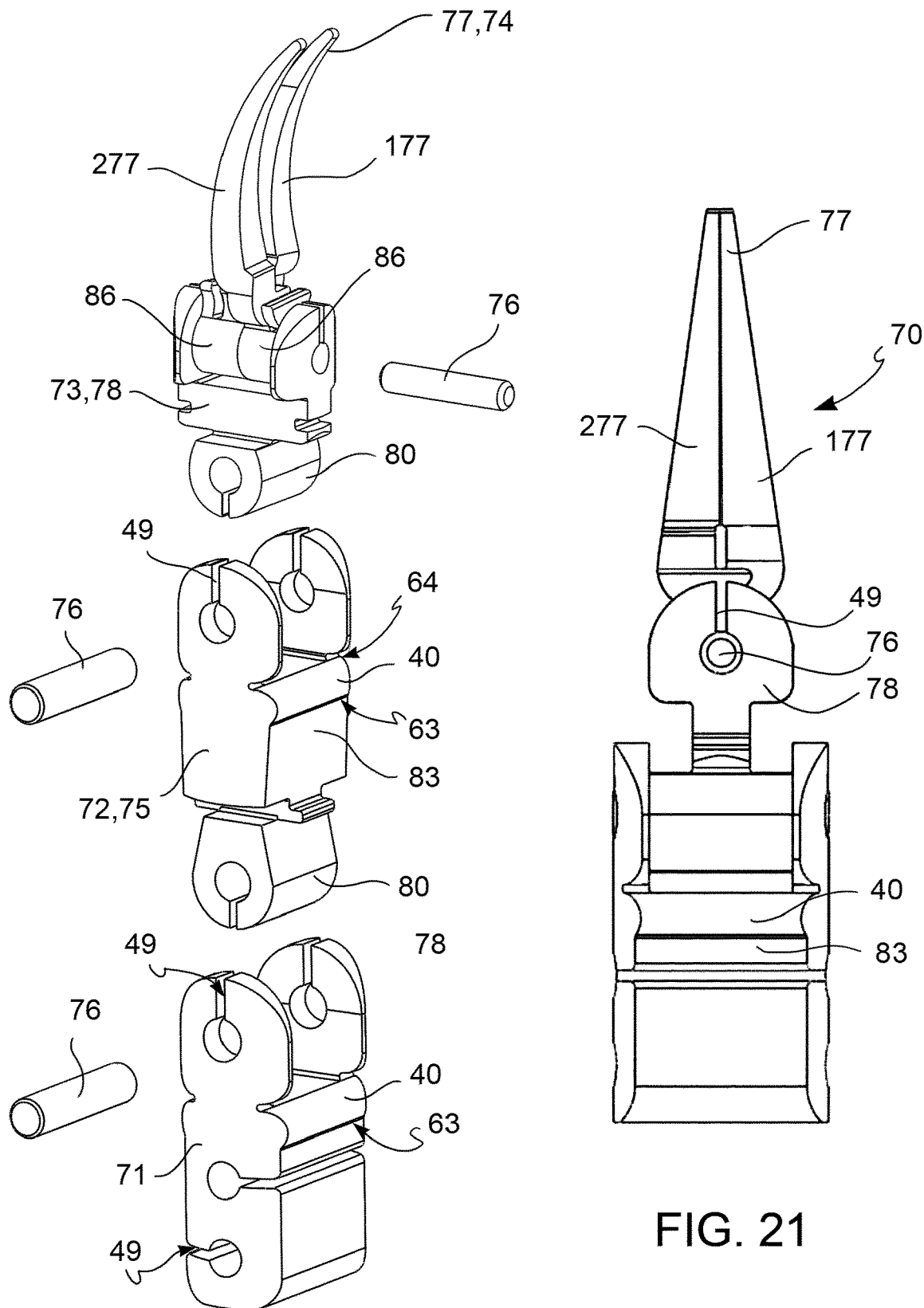
Figure 22:
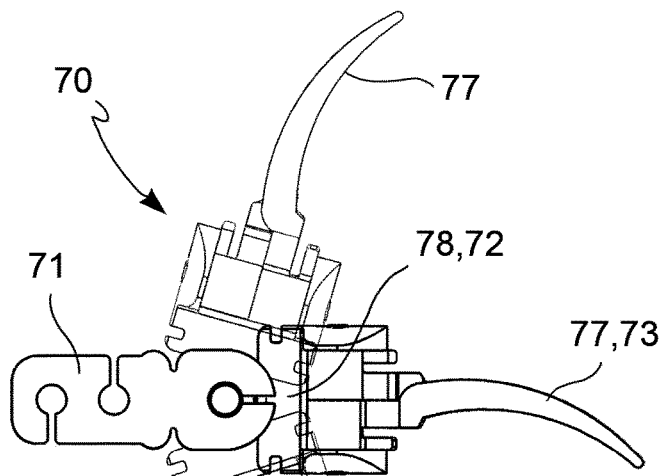
Figure 23:
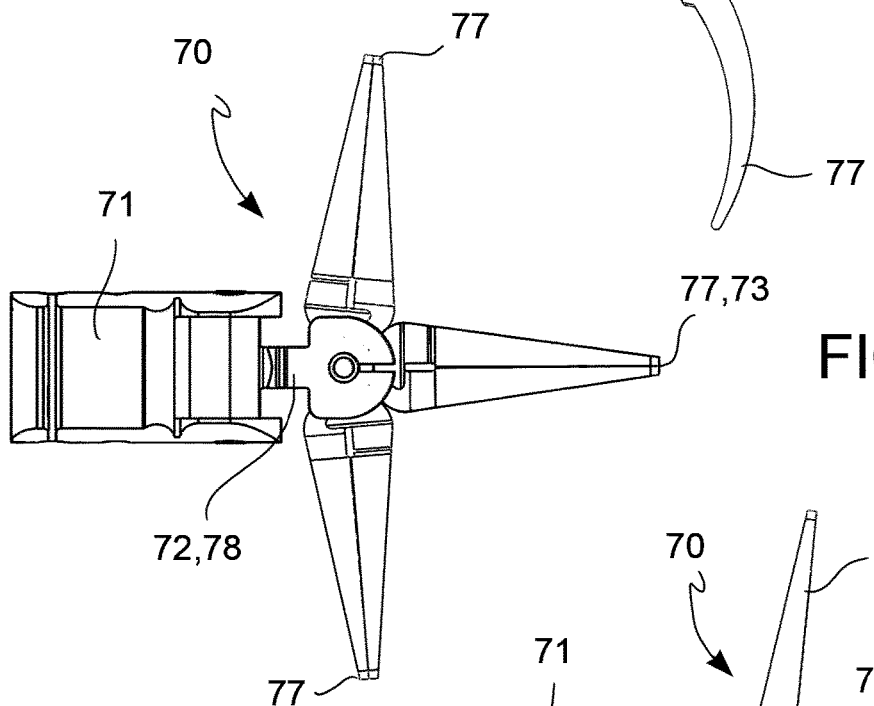
Figure 24:
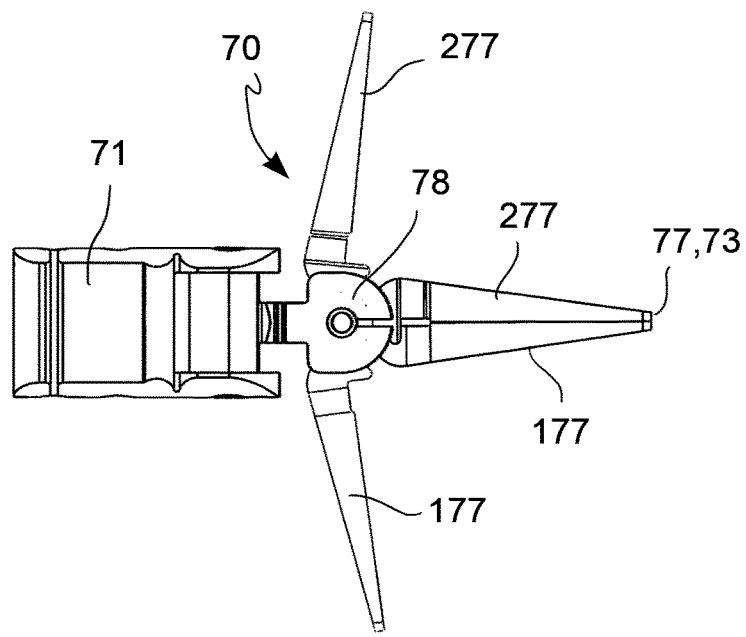
Figure 25:
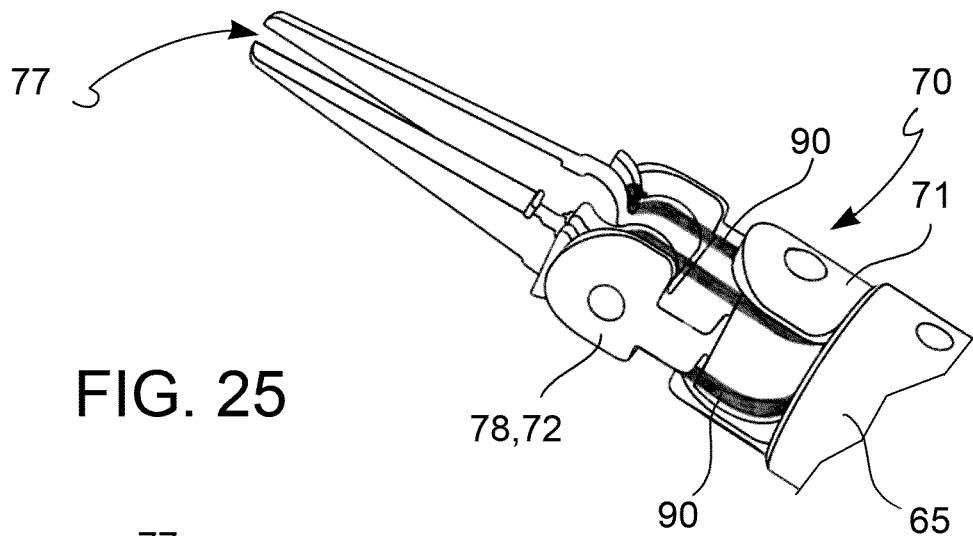
Figure 26:
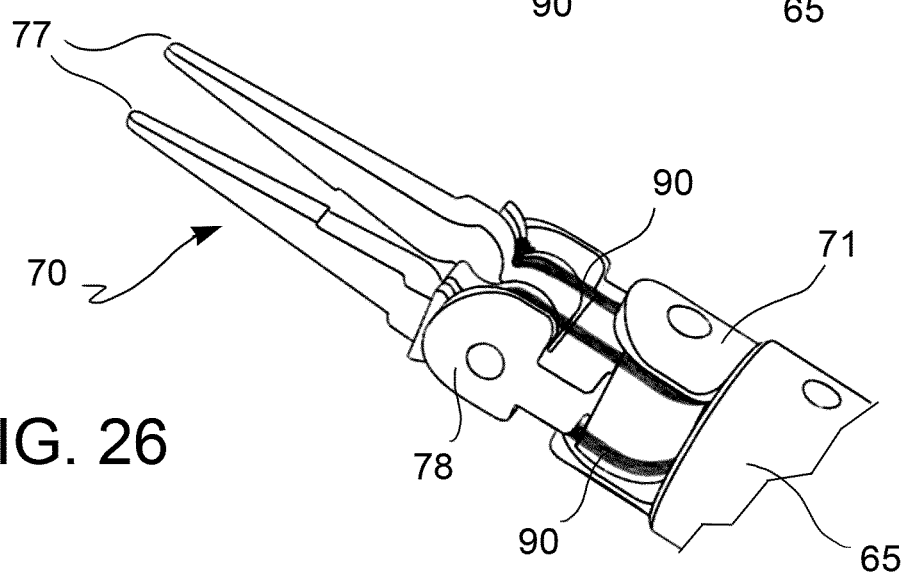
Figure 27:
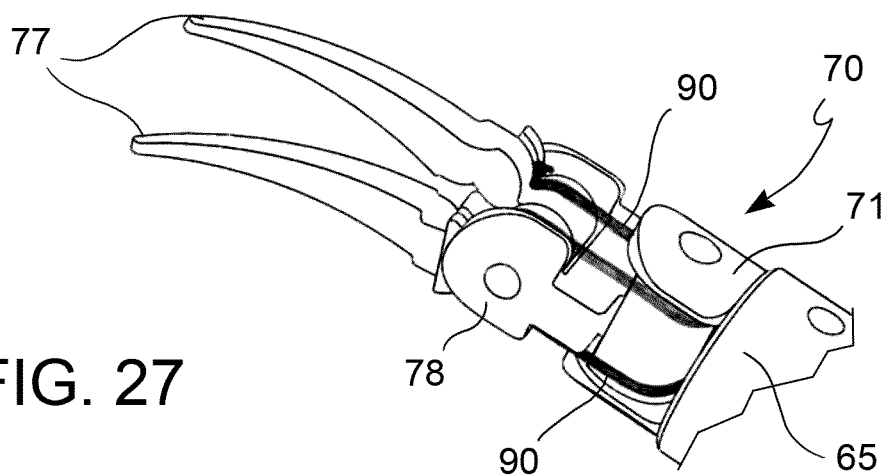
Figures 28, 29:
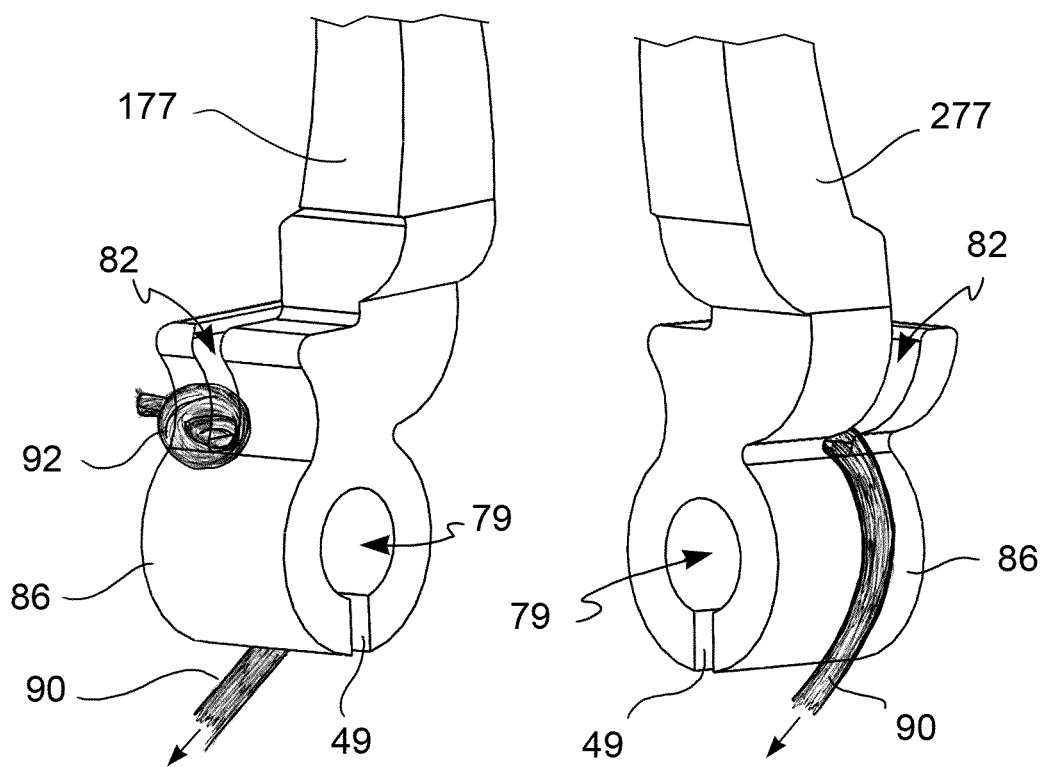
Figure 30:
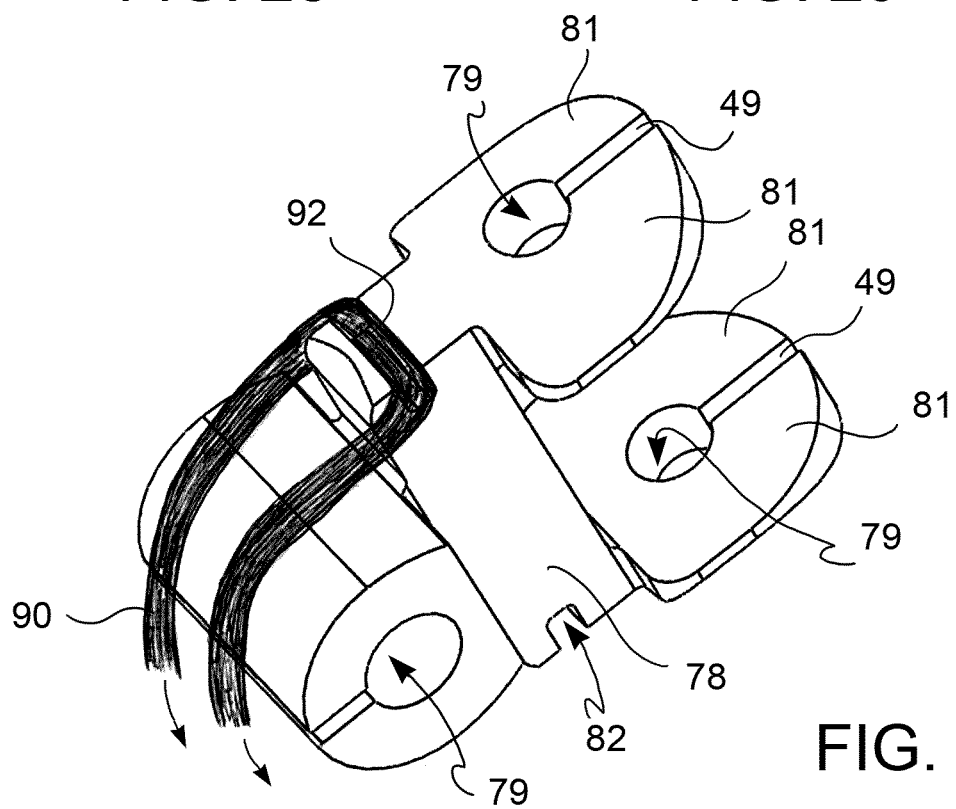
Figure 31:
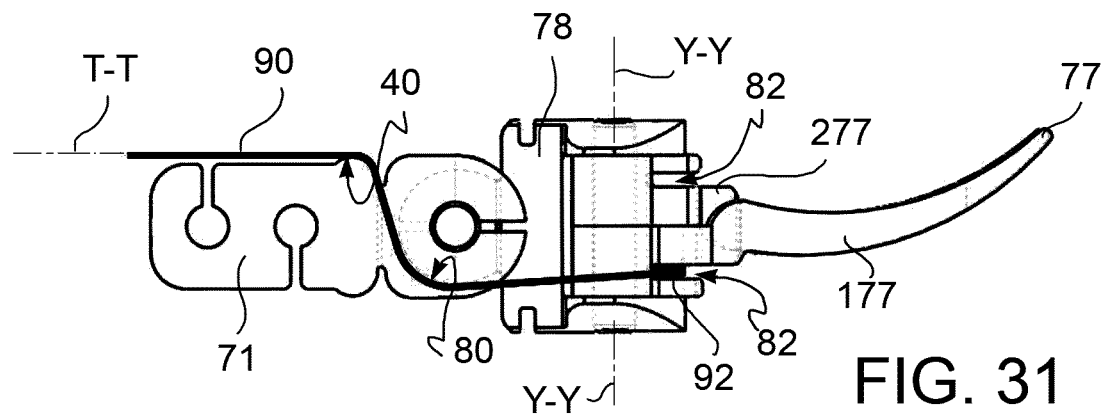
Figure 32:
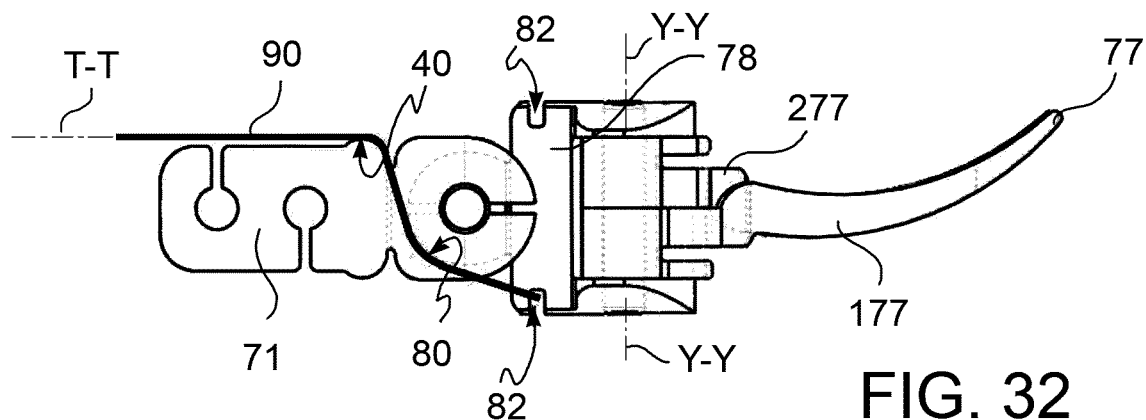
Figure 33:
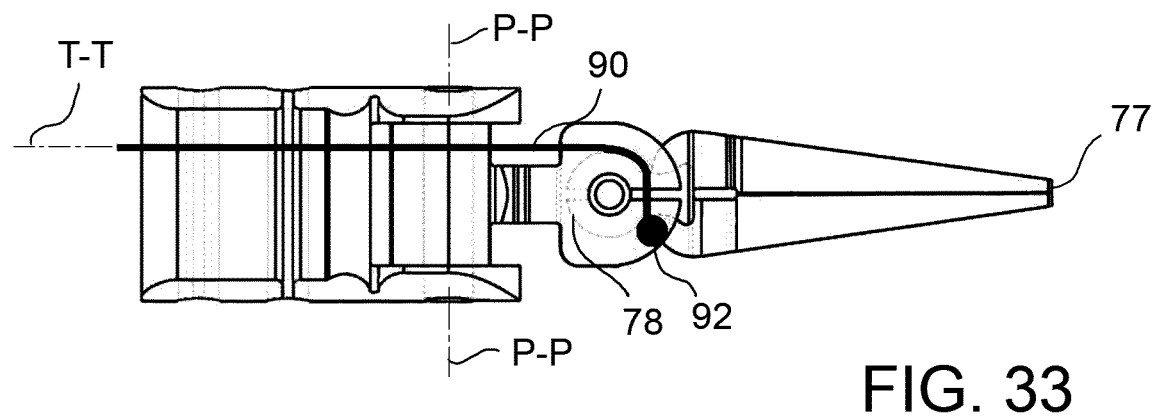
Figure 34:
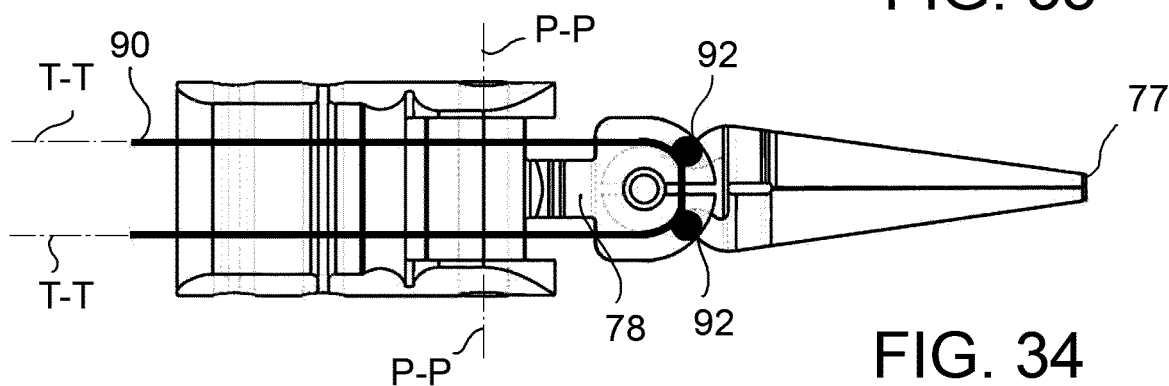
Figure 37:
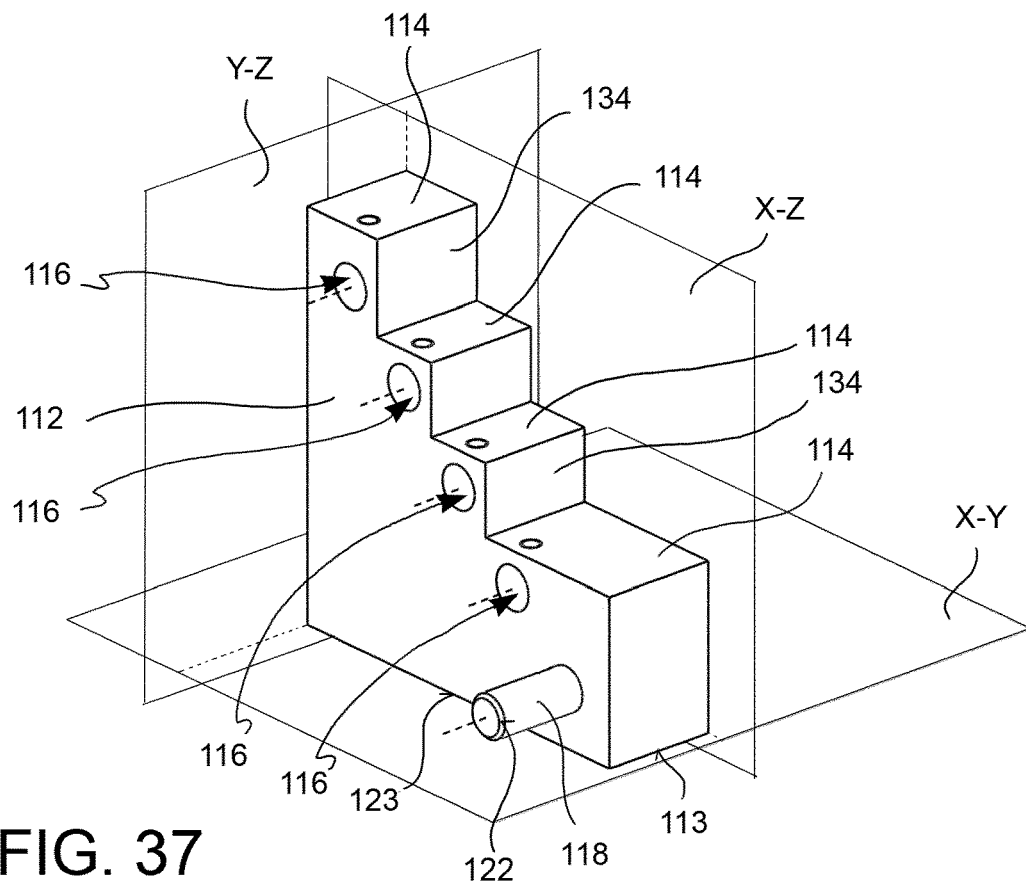
Figure 38:
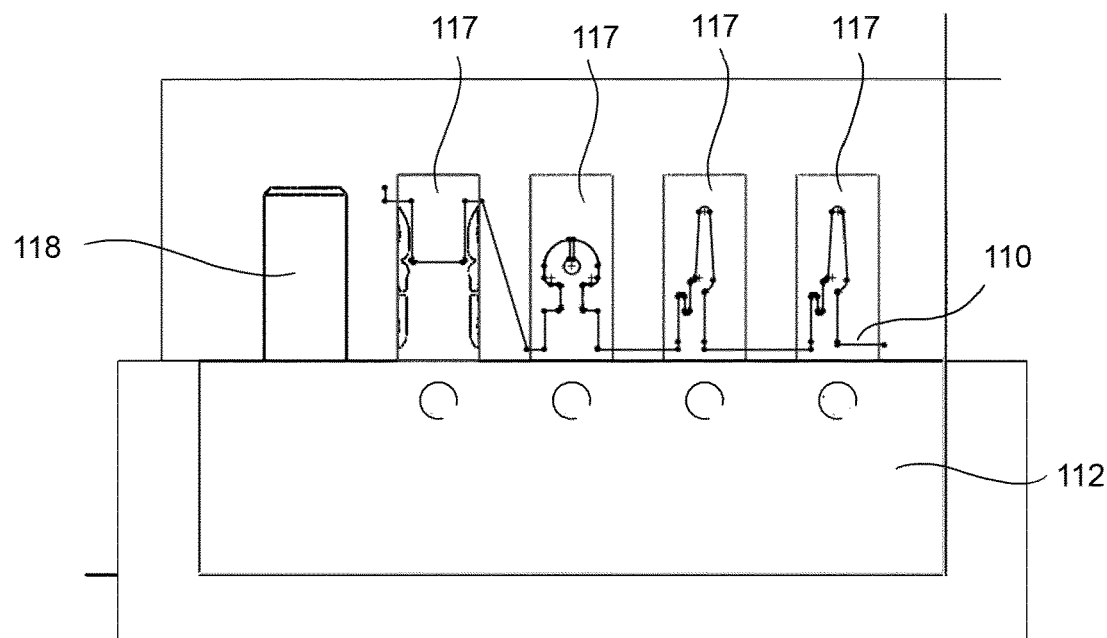
Figure 39:
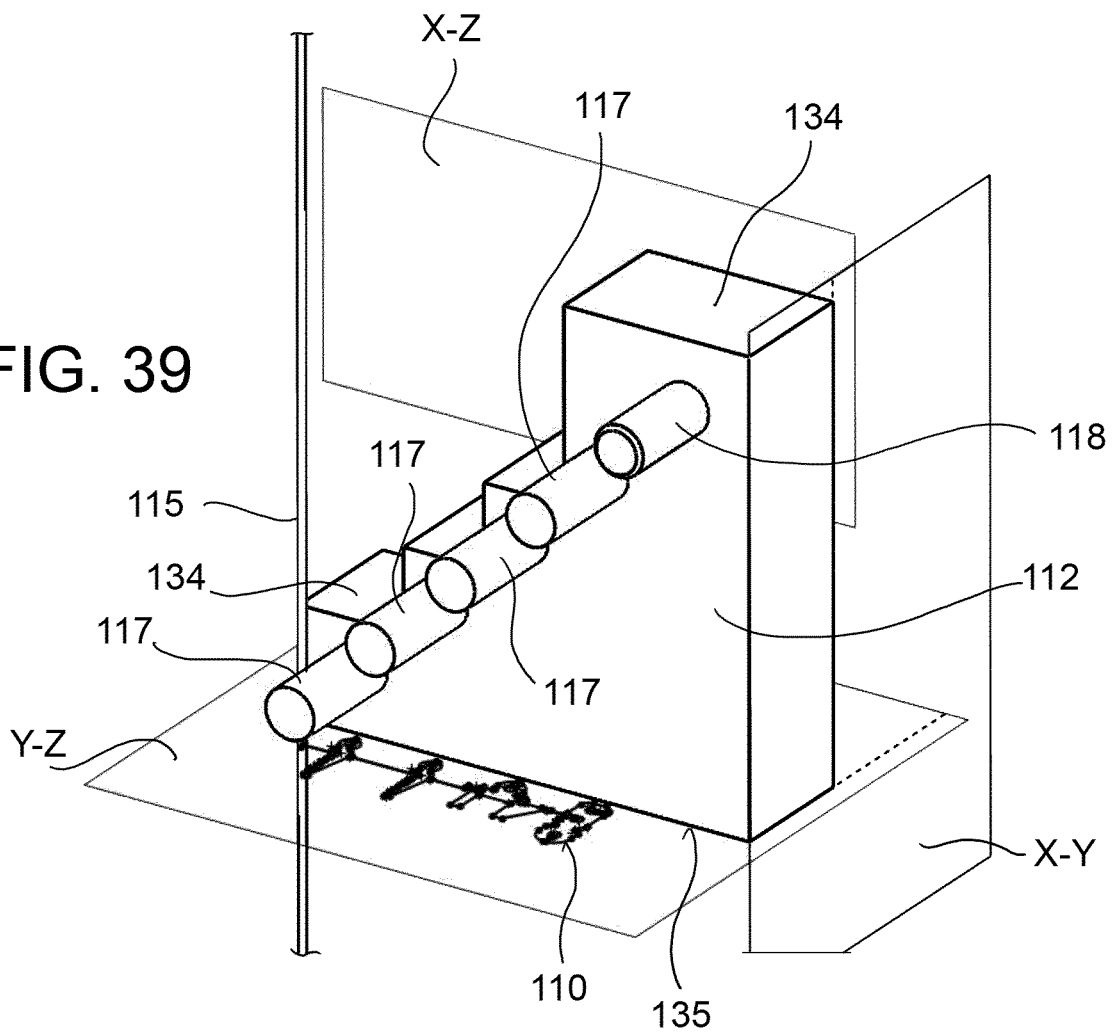
Figure 40:
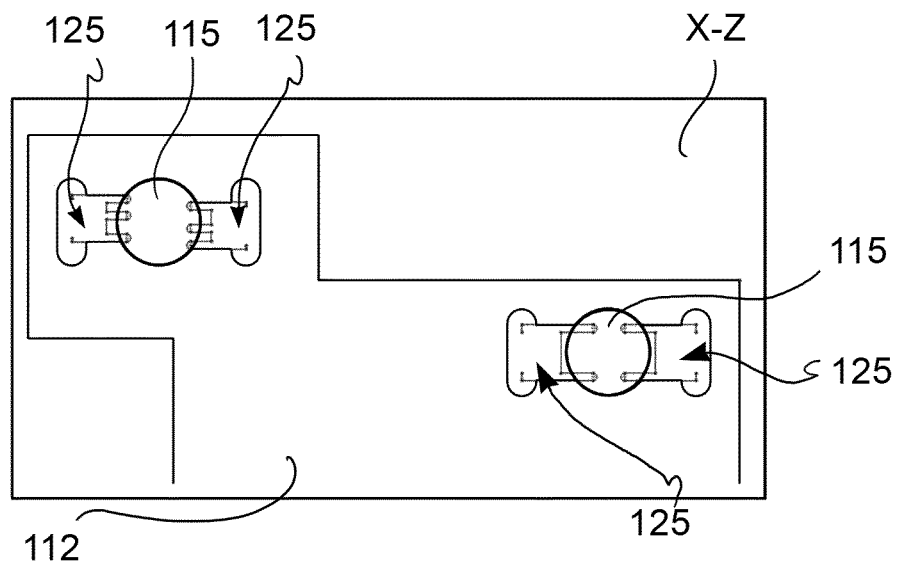
Figure 40B:
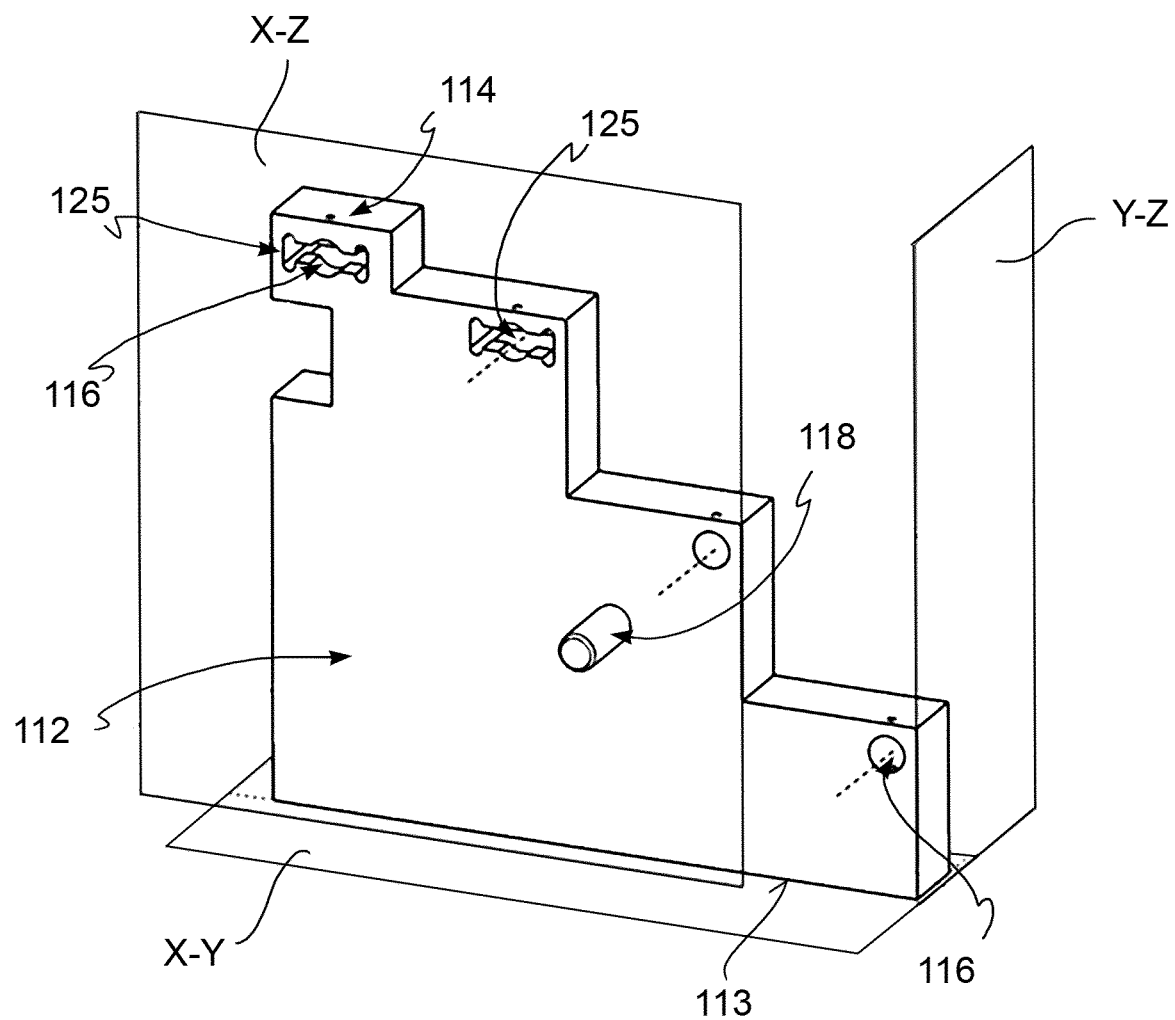
Figure 41:
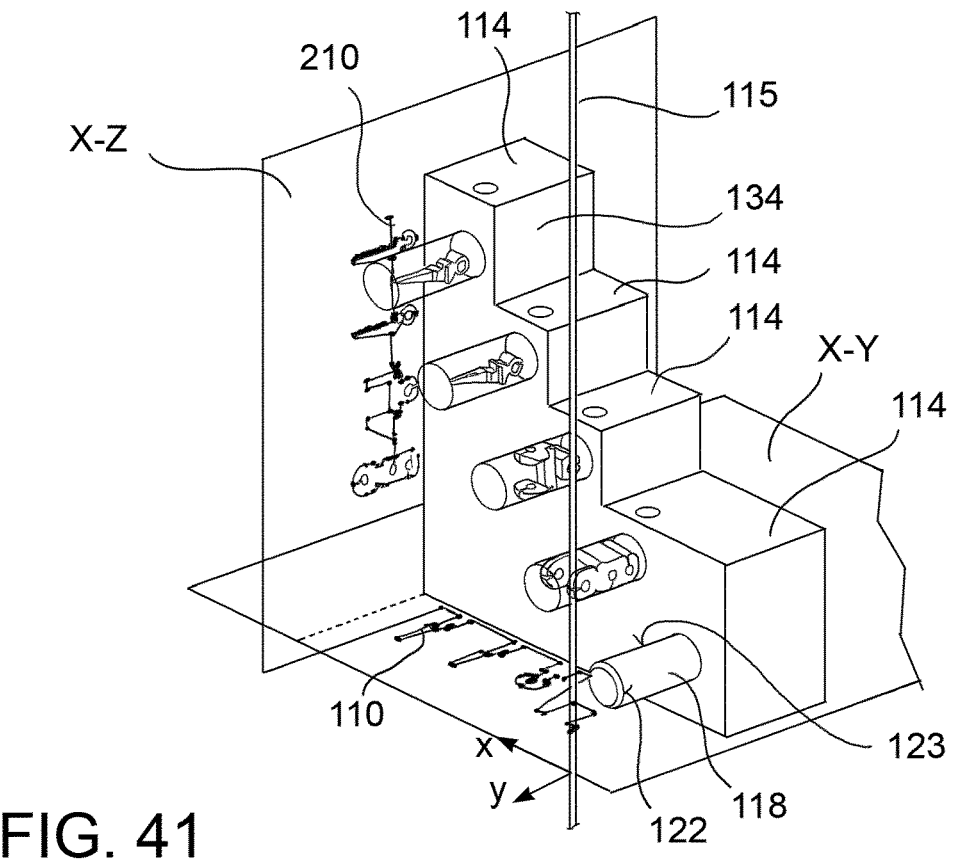
Figure 42:
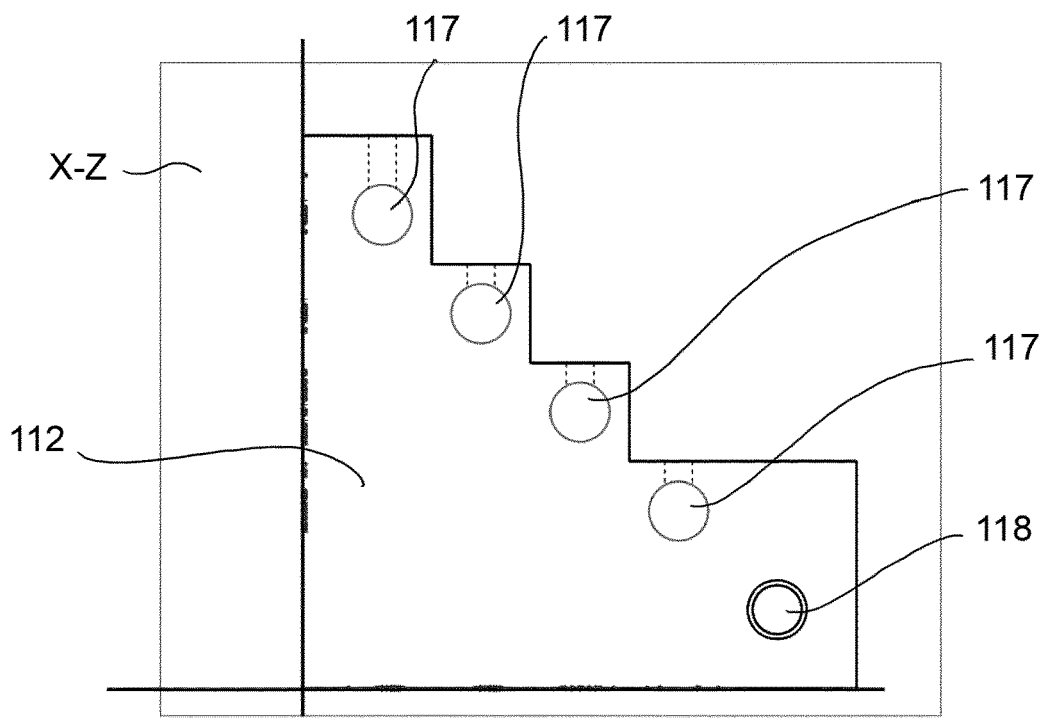
Figure 43:
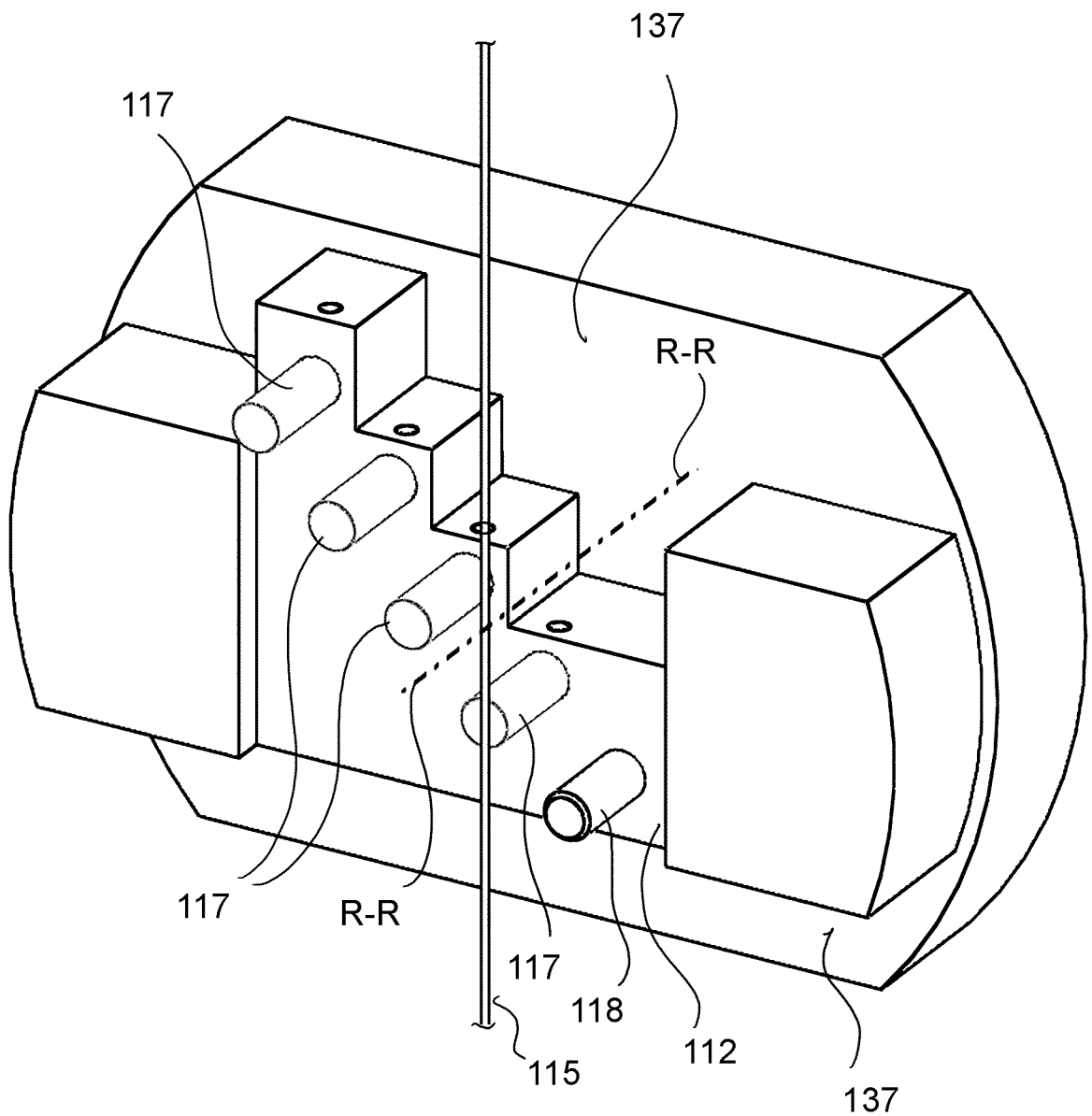

The FIG. 15A is a perspective view that shows a medical instrument.

the FIG. 15B is a perspective view that shows a medical instrument.

the FIG. 15C is a sketch in perspective view that shows a medical instrument.

the FIG. 15D is a sketch in perspective view that shows a medical instrument.

the FIG. 16 is a schematic drawing, viewed from top and with partially transparent parts, which shows a tendon path of two tendons.

the FIG. 17 is a perspective view of an articulated device according to an aspect of the invention.

the FIGS. 18 to 20 are perspective views with isolated parts of some embodiments of an articulated device, according to several aspects of the invention.

the FIG. 21 shows a profile of an articulated device.

the FIGS. 22 to 24 show several poses of some embodiments of an articulated device according to some aspects of the invention.

the FIGS. 25 to 27 shows several embodiments of a terminal tool according to some aspects of the invention.

the FIG. 28 shows a perspective view of a detail of a tendon.

the FIG. 29 shows a perspective view of a detail of a tendon.

the FIG. 30 shows a perspective view of a detail of a tendon.

the FIGS. 31 to 36 are schematics, which show a path of the tendon according to some aspects of the invention.

the FIG. 37 is a schematic in perspective view, which shows a machining fixture according to one aspect of the invention.

the FIG. 38 is a schematic, which shows the profile of a machining cut according to one aspect of the invention.

the FIG. 39 is a schematic in perspective, which shows a phase of a fabrication method according to one aspect of the invention.

the FIG. 40A is a planar view, which shows a detail of a machining fixture according to one aspect of the invention.

the FIG. 40B is a perspective view, which shows a detail of a machining fixture according to one aspect of the invention.

the FIG. 41 is a schematic in perspective view, which shows a phase of a fabrication method according to one aspect of the invention.

the FIG. 42 is a frontal view of a tool according to one aspect of the invention;

the FIG. 43 is a perspective view of a machining fixture mounted on a rotatory support table, according to an aspect of the present invention.

DESCRIPTION OF PREFERRED EMBODIMENTS

According to one embodiment, the term "tendon", or "actuation cable", refers to an element which presents a prevalently longitudinal extension and is suitable to work under tensile loads applied at its endpoints. According to one embodiment, the term "opposite tendon" or "opposite actuation cable" refers to a further tendon suitable to work in an antagonistic way with respect to said tendon. According to one embodiment, in the attached figures, said tendon will generally be indicated by the numeric reference "90" and said opposite tendon will be indicated by the numeric reference increased by one hundred, that is "190". Nonetheless, in figures in which distinguishing between said tendon and said opposite tendon is irrelevant, said tendon and said opposite tendon will both be indicated by the numeric reference 90. According to an embodiment, the concept of "opposite" extends itself to multiple elements and/or parts of elements, such as referred to for said "tendon" above. According to an embodiment, the tendons comprised in a first pair of tendons will be indicated with references "90, 190", and the tendons belonging to a second pair of tendons will be indicated with the references "191, 192".

According to one embodiment, the terms "master-slave", "master" and "slave" refer to the known system of teleoperation.

According to one embodiment, the term "terminal tool" refers to a portion suitable to perform an assigned task, such as for example form the interface with at least on portion of the patient. For example, in a teleoperation system of the master-slave type, said terminal tool, or terminal portion, or terminal member, is at least one portion of an "end-effector".

According to one embodiment, the term "jointed or articulated device" refers to a wrist joint, an elbow joint or a shoulder joint of a robotic or mechatronic structure, in other words, an interconnected assembly of members and articulations suitable to support and/or orient and/or position and/or influence the position of said terminal tool.

According to one embodiment, the members of a jointed or articulated device will be indicated by the progressive annotation "first member", "second member", and so on, to indicate their position within the kinematic chain, in which the "first member" indicates the most proximal member; in other words "first member" indicates the member furthest from the terminal organ. According to one embodiment, the members of the jointed device will be indicated with the terms "wrist member", "elbow member" or "terminal member" to indicate the function exercised by said members. For example, the same member could be simultaneously a "second member" and a "wrist member".

According to one embodiment, the term "work volume", or "work space", or "work field", or "workspace volume" refers to the set of Cartesian poses accessible to the terminal portion of a jointed or articulated device. According to one embodiment, said volume is of a substantially parallelepiped form. According to one embodiment, said work volume is of a substantially cylindrical form.

According to one embodiment, the term "macro-positioning" refers to an initial operation of positioning of at least one portion of the medical instrument from any position to a work position within or adjacent to the operating field; in other words, "macro-positioning" refers to the operation of making the work volume coincide with the operating field.

According to one embodiment, the term "micro-positioning" refers to an operation of positioning at least one portion of a medical instrument in a finer manner than the "macro-positioning". According to one embodiment the micro-positioning takes place in a more limited space, in real time and under the direct control of the control device (master).

According to one embodiment, the prefix "micro-" before a certain object indicates that said object is primarily, but not exclusively, meant to operate on a sub-millimeter scale.

According to one embodiment, the term "rotational joint" refers to a junction between two elements suitable to permit a relative moment of rotation between said two elements around an axis of joint movement.

According to one embodiment, the term "medical instrument" refers to an instrument suitable to be used during at least one phase of a medical surgical and/or cosmetic therapy. According to one embodiment, the term "surgical instrument" refers to a medical instrument specifically suited to be generally used in at least one phase of a surgical therapy. According to one embodiment, the term "microsurgical instrument" or "surgical micro-instrument" refers to a medical instrument specifically suited to be used in at least one phase of a microsurgical therapy.

According to one embodiment, the term "frame" refers to a portion of a medical instrument primarily suited to have a structural holding function. According to one embodiment, the "frame" can comprise at least one shaft, that is a long rigid or flexible element that presents a primarily longitudinal extension. According to one embodiment, said shaft, for example can be of a hollow and/or tubular form.

According to one embodiment, the term "ruled surface" refers to a surface achieved by the union of multiple straight lines. According to one embodiment, if not otherwise explicitly stated, the term "ruled surface" refers to a surface achieved by the union of multiple straight lines substantially parallel to each other, or in other words, a ruled surface of substantially parallel generatrices.

Below, when reference is made to a device, or an assembly, or a method, for microsurgery, it is meant a device, assembly or method, suitable to be applied in microsurgery, i.e. with the simultaneous use of means of optical enlargement such as loupes or microscopes, but also suitable for applications in other surgical therapies, such as general surgery, laparoscopic surgery or endoscopic surgery.

According to an embodiment, to not burden the text or figures, when reference is made to a "first" or "second" element (for example a "first micro-positioning device" and a "second micro-positioning device"), they will be indicated with the same numeric reference, as long as they are functionally indistinguishable (for example "41" above); sometimes, due to a need for clarity, the numerical reference will be specified incremented by one hundred (for example "141" above and "241"); hence, for example, the numerical reference "41" will indicate both said "first micro-positioning device" and said "second micro-positioning device", as well as a "third" micro-positioning device. While when the specific reference, for example "141", is used, it will refer to the specific element, in this case the "first micro-positioning device". Analogously, to not burden the text excessively, the numeric reference relating to an "opposite" element will be omitted, if an element is functionally indistinguishable from its opposite.

According to a general embodiment, a method of manufacturing a jointed device 70, 170, 270 of a medical instrument 60, 160, 260, 360 comprising the following steps:
(a) providing a machining fixture 112 on a wire electrical discharge machine having an electrical discharge wire 115, said machining fixture 112 comprising a plurality of member holes 116 each adapted to accommodate at least one workpiece 117, said workpiece 117 being adapted to form at least one portion of said jointed device 70, 170, 270 of said medical instrument 60, 160, 260, 360;
(b) providing at least two workpieces 117, comprising a first workpiece and a second workpiece, accommodated within at least two member holes 116 of said plurality of member holes 116;
(c) associating said machining fixture 112 to the wire electrical discharge machine so that said electrical discharge wire 115 can cut at most one of said at least two workpieces 117 at time;
(d) cutting said at least two workpieces 117 by said electrical discharge wire 115;

(e) rotating the machining fixture 112 around a fixture rotation axis R-R of a predetermined fixture rotation angle, said predetermined fixture rotation angle being chosen to provide that said electrical discharge wire 115 can cut at most one of said at least two workpieces 117 at time;
(f) cutting said workpieces 117 by said electrical discharge wire.

Thanks to such machining fixture 112 and the above described method, the portion which has already been machined of each workpiece 117, remains within said member seat 116 until the cut on the last plane has been performed. The cuts made the second cutting plane intersect those made in the first cutting plane. That improves the precision of the results particularly when the workpieces have to be joined together.

According to an embodiment, said predetermined fixture rotation angle is substantially equal to 90°.

According to an embodiment, the step (d) is performed on a first cutting plane X-Y along a first cutting profile 110.

According to an embodiment, the step (f) is performed on a second cutting plane Y-Z along a second cutting profile 210.

According to an embodiment, said cutting profile 110 is the trajectory followed by the cutting wire 115 during electro discharge machining and it is orthogonal to his feed rate. Said cutting profile 110 comprises the shapes of a plurality of workpieces.

According to an embodiment, said cutting profile 110 lies on said cutting plane X-Y or Y-Z or X-Z. Said cutting plane X-Y or Y-Z or X-Z is orthogonal to wire feed direction.

According to an embodiment, said cutting profile 110 lies on said cutting plane X-Y, Y-Z, X-Z. Said cutting plane X-Y, Y-Z, X-Z is orthogonal to wire feed direction.

According to an embodiment, the step (d) comprises the substep of shaping said second workpiece differently from said first workpiece. According to an embodiment, the first cutting profile 110 describes on said first workpiece and on said second workpiece different paths.

According to an embodiment, the step (d) comprises the substep of shaping a portion of said second workpiece complementary to a portion of said first workpiece. In this way, is possible to miniaturize the dimensions of parts that are intended to be coupled together.

According to an embodiment, the step (e) comprises the substep of shaping said second workpiece differently from said first workpiece. According to an embodiment, the first cutting profile 210 describes on said first workpiece and on said second workpiece different paths.

According to an embodiment, the step (e) comprises the substep of shaping a portion of said second workpiece complementary to a portion of said first workpiece. In this way, is possible to miniaturize the dimensions of parts that are intended to be coupled together.

According to an embodiment, said method comprises the further steps of:
repeating step (e),
performing step (f) on a third cutting plane X-Z.

According to an embodiment, said fixture rotation axis R-R is orthogonal to both said first cutting plane X-Y and said second cutting plane Y-Z.

According to an embodiment, the orientation of said plurality of member seats 116 are parallel to each other.

According to an embodiment, said fixture rotation axis R-R) is substantially parallel to the orientation of said member seats 116.

According to an embodiment, the method comprises the further step of performing a calibration.

According to an embodiment, said step of performing a calibration is performed before defining a first cutting profile 110 in said first cutting plane X-Y, and before defining a second cutting profile 210 in said second cutting plane Y-Z.

According to an embodiment, said step of performing a calibration comprises the substep of measuring a distance between said first workpiece and said second workpiece along said first cutting plane X-Y or said second cutting plane Y-Z.

According to an embodiment, a machining fixture 112 of a medical instruments 60, 160, 260, 360 comprising a jointed device 70, 170, 270 is provided. Said fixture 112, or machining fixture 112, is adapted to be mounted on a wire electrical discharge machine having an electrical discharge machine wire 115 moving transversely with respect to the feed rate direction of the wire electrical discharge machine.

According to an embodiment, said fixture 112 comprises a plurality of member holes 116, each adapted to accommodate at least one workpiece 117, wherein said at least one workpiece 117 is adapted to form at least one portion of said jointed device 70, 170, 270 of said medical instrument 60, 160, 260, 360.

According to an embodiment, said fixture 112 is suitable for use for at least two cuts on at least two of said plurality of workpieces 117 accommodated in at least two of said plurality of member holes 116, said at least two cuts are performed in at least two cutting planes comprising a first cutting plane X-Y and a second cutting plane Y-Z. According to an embodiment, said first cutting plane X-Y and said second cutting plane Y-Z are mutually orthogonal.

According to an embodiment, said plurality of member holes 116 are arranged in succession on said fixture 112, so that said electrical discharge machine wire 115 intersects at most only one of said workpieces 117 at a time, when said workpieces 117 are mounted in respective member holes 116 and cut both on said fist cutting plane X-Y and said second cutting plane Y-Z.

According to an embodiment, two orthogonal axis lying in the cutting planes X-Y, Y-Z intersect at most only one workpiece 117. According to an embodiment, the cutting wire 115 both when advances substantially orthogonal to said first cutting plane X-Y and substantially orthogonal to said second cutting plane Y-Z, intersects at most only one of said workpieces 117 at a time. According to an embodiment, two lines orthogonal to each other and orthogonal to the member hole 116 axis, intersects at most only one of said workpieces 117 at a time.

Thanks to such a fixture 112 is possible to realize on the same workpieces two cuts on different cutting planes, without a further placement the workpieces 117 on the fixture 112. This allows to improve the precision of manufacturing two or more workpieces intended to be coupled one another.

According to an embodiment, said fixture 112 is associated to a rotatably support table 137 for rotating said fixture 112 around said first fixture rotation axis, avoiding disassembling said fixture 112 from the wire electrical discharge machine, and wherein said first fixture rotation axis is substantially parallel to the intersection line between said first cutting plane X-Y and said second cutting plane Y-Z. The provision of such rotatably support table 137 allows to rotate the fixture 112 in its entirety. Said rotatably support table 137 pivots around a table axis of rotation R-R. The fixture 112 associated to said rotatably support table 137 pivots around a table axis of rotation R-R.

According to an embodiment, said fixture rotation axis R-R is parallel to the line generated from the intersection of said first cutting plane X-Y and said second cutting plane Y-Z.

According to an embodiment, said fixture 112 comprises a first pair of fixing surfaces 113, 114, said first pair of fixing surfaces 113, 114 being precision finished, opposite and substantially parallel to each other and substantially orthogonal to a first cutting plane X-Y. According to an embodiment, said fixture 112 comprises a second pair of fixing surfaces 134, 135, said second pair of fixing surfaces 134, 135 being precision finished, opposite and substantially parallel to each other and substantially orthogonal to a second cutting plane Y-Z.

According to an embodiment, said fastening surfaces are arranged offset, forming a ladder profile.

According to an embodiment, said fixture 112 is suitable for use for at least three cuts on at least two of said workpieces 117 in at least three cutting planes comprising a first cutting plane X-Y, a second cutting plane Y-Z and a third cutting plane X-Z; wherein said plurality of member holes 116 are arranged in succession so that a translating straight line, substantially orthogonal to said first cutting plane X-Y, substantially orthogonal to said second cutting plane Y-Z and substantially orthogonal to said third cutting plane X-Z intersects at most only one of said workpieces 117, when mounted in respective member holes 116. According to an embodiment, said first cutting plane X-Y, second cutting plane Y-Z and said third cutting plane X-Z are mutually orthogonal. According to an embodiment, said fixture 112 further comprises a third pair of precision finished fixing surfaces, opposite and substantially parallel to each other and substantially orthogonal to a third cutting plane X-Z.

According to an embodiment of the invention, a surgical robotic assembly 100 comprises:
- at least one micro-positioning device 41, 141, 241, 341 having multiple degrees of freedom at least of translation.
- at least one medical instrument 60, comprising one jointed or articulated device 70 having multiple rotational degrees of freedom.

According to an embodiment, said medical instrument 60 is connected in series, to said micro-positioning device 41 such that said articulated device 70 reaches a predefined position in a work volume 7 with its terminal portion 77. According to one embodiment, said medical instrument 60 comprises at least a shaft 65, suitable to connect said frame 57 with said jointed device 70.

According to one embodiment, said robotic assembly 100 comprises a support 104 and at least one macro-positioning arm 30, connected to said support 104, with respect to which said macro-positioning arm 30 provides multiple degrees of freedom of macro positioning.

According to one embodiment, said micro-positioning device 41, 141, 241 and 341 is connected in cascade, that is in series, to said macro-positioning arm 30.

According to one embodiment, said micro-positioning device 41 comprises degrees of freedom exclusively of translation.

According to one embodiment, said micro-positioning device 41 comprises a X-Y-Z cartesian kinematic mechanism and a further rotational degree of freedom, around a rotational axis which substantially coincides with the longitudinal direction in which the medical instrument develops.

According to one embodiment, said at least one medical instrument 60, 160, 260, 360 comprising one jointed device 70, 170, 270, has multiple degrees of freedom that are exclusively rotational.

According to one embodiment, a robotic surgical assembly 100 comprises a further micro-positioning device 41, such that it comprises at least a first micro-positioning device 141 and a second micro-positioning device 241.

According to one embodiment, said at least two micro-positioning devices 141, 241 are placed parallel to each other. According to one embodiment, said at least two micro-positioning devices are placed side-by-side to move one medical instrument on the right and one medical instrument on the left.

According to one embodiment, a surgical robotic assembly 100 comprises a further medical instrument 60 such as to comprise at least a first medical instrument 160, connected in cascade, or in series, to said first micro-positioning device 141 and at least a second medical instrument 260, connected in cascade, or in series, to said second micro-positioning device 241.

According to one embodiment, said first medical instrument 160 comprises one jointed device 170 and said second medical instrument comprises a second jointed device 270.

According to one embodiment, said first micro-positioning device 141 and said second micro-positioning device 241 are placed in such a way that the respective terminal portions 77 of each jointed device 70 reach respective work volumes 7 which must at least partially overlap.

The provision of work volumes 7 that at least partially overlap permits an operation in context using at least two medical instruments on one single portion of the patient.

According to one embodiment, said respective work volumes 7 substantially coincide.

According to one embodiment, said macro-positioning arm 30 comprises at least one support member 38, comprising at least one attachment feature 39, suited to hold at least one portion of at least one micro-positioning device 41.

According to one embodiment, said support member 38 is suited to simultaneously carry/receive at least one portion of said first micro-positioning device 141 and at least one portion of said second micro-positioning device 241.

According to one embodiment, said support member 38 comprises at least one other attachment feature 39, such that it comprises at least three attachment features 39, said further attachment feature 39 being suitable to hold at least one portion of a further micro-positioning device 41.

According to one embodiment, said robotic assembly 100 comprises at least three micro-positioning devices 41, 141, 241, 341.

According to one embodiment, said robotic assembly 100 comprises at least three medical instruments 60, 160, 260, 360.

According to one embodiment, said three medical instruments 60, 160, 260, 360 are positioned in cascade, or in series, with a co-respective micro-positioning device 41, 141, 241, 341, of said at least three micro-positioning devices 41, 141, 241, 341.

According to one embodiment, said first micro-positioning device 141, said second micro-positioning device 241 and said third micro-positioning device 341 are located such that the terminal positions 77 of each jointed device 70 reach respective work volumes that are at least partially overlapping.

According to one embodiment, said support member 38 comprises at least three attachment features 39, each suited to hold at least one portion of a micro-positioning device 41.

According to one embodiment, said macro-positioning arm 30 comprises:
one first arm member 31, connected to said support 104 and mobile with respect to said support 104 along a linear sliding guide 36,
a second arm member 32, connected to said first arm member 31 around a first axis of movement a-a.

The provision that said first member of the arm 31 is mobile with respect to said support 104 along a linear sliding guide 36, allows for a up and down movement to get closer or further from the operating field.

According to one embodiment, said macro-positioning arm 30 further comprises a third arm member 33 connected to a second arm member 32 and mobile with respect to said second arm member 32 around a second axis of movement of the arm b-b.

According to one embodiment, said macro-positioning arm 30 further comprises a fourth arm member 34 connected to said third arm member 33 and mobile with respect to said third arm member 33 around a third axis of movement of the arm c-c.

According to one embodiment, said macro-positioning arm 30 further comprises at least one rotational dial nut 43, which is mobile around a fourth axis of movement of the arm d-d, and is suitable to be manipulated to move said support member 38 around said fourth axis of movement of the arm d-d.

According to one embodiment, said five degrees of freedom of said macro-positioning arm 30 are a translational movement which is substantially vertical, three substantially rotational movements around said first, second and third axis of movement of arm a-a, b-b, c-c and at least one rotational movement around said fourth axis of movement of the arm d-d.

According to one embodiment, said rotational dial nut 43 comprises a click or non-continuous movement mechanism defining pre-established displacements.

According to one embodiment, said first axis of movement of the arm a-a, said second axis of movement of the arm b-b and said third axis of movement of the arm c-c are substantially parallel to each other.

According to one embodiment, said fourth axis of movement of the arm d-d is substantially orthogonal to said third axis of movement of the arm c-c.

According to one embodiment, a manual knob 37 moving a rack and pinion mechanism controls the movement of said first member of the arm 31 in said linear sliding guide 36 by its rotational movement.

According to one embodiment, said macro-positioning arm 30 comprises at least one braking system, suitable for blocking the relative movement of at least two of said support 104, said first member of the arm 31, said second member of the arm 32, said third member of the arm 33, said fourth member of the arm 34.

According to one embodiment, said macro-positioning arm 30 comprises at least one release button 35, or unlocking button, which can be switched between a brake (or lock) and a release (or unlock) position.

According to one embodiment, each micro-positioning device 41 comprises a spherical joint 173, said spherical joint 173 is positioned in cascade, or in series, upstream of each micro-positioning device 41.

According to one embodiment, for example shown in FIG. 2B, each micro-positioning device 41, 141, 241 comprises a spherical joint 173, suitable to change the orientation of the medical instrument 60, 160, 260 by moving the micro-positioning device 41, 141, 241, from its base, i.e.

most proximal portion. According to one embodiment, said spherical joint 173 is a universal joint that can be blocked.

According to one embodiment, said micro-positioning device 41 comprises a first motorized slide 51, mobile along a first sliding rail 54 along a first sliding direction f-f.

According to one embodiment, said micro-positioning device 41 comprises a second motorized slide 52, mobile along a second sliding rail 55 along a second sliding direction g-g.

According to one embodiment, said micro-positioning device 41 comprises a third motorized slide 53, mobile along a third sliding rail 56 along a third sliding direction h-h.

According to one embodiment, said first sliding direction f-f is substantially rectilinear.

According to one embodiment, said second sliding direction g-g is substantially rectilinear.

According to one embodiment, said second sliding direction g-g is substantially orthogonal with respect to said first sliding direction f-f.

According to one embodiment, said third sliding direction h-h is substantially rectilinear.

According to one embodiment, said third sliding direction h-h is substantially orthogonal with respect to both said first sliding direction f-f and said second sliding direction g-g. According to one embodiment, the third sliding direction h-h is aligned with the shaft 65.

According to one embodiment, said micro-positioning device 41 is suitable for working with a stepper motor or a servo-motor. According to one embodiment, said micro-positioning device 41 is suitable to work with a piezoelectric motor or an ultrasonic motor.

According to one embodiment, said medical instrument 60 comprises a motorized rotary joint 46, suitable for moving said medical instrument 60 around a longitudinal axis of rotation r-r.

According to one embodiment, said micro-positioning device 41 also comprises a motorized rotary joint 46, suitable for moving said medical instrument 60 around a longitudinal axis of rotation r-r.

According to one embodiment, said axis of longitudinal rotation r-r substantially coincides with its longitudinal axis of development, or axis of the instrument X-X, or longitudinal axis of the shaft X-X, of said medical instrument 60.

According to an embodiment, a shaft angle θ is defined as the angle between the shaft direction X-X of the shaft 65 of said first medical instrument 160 and the shaft direction X-X of the shaft 65 of said second medical instrument 260.

According to one embodiment, said medical instrument 60 comprises one articulated device 70 with two degrees of freedom of rotation. According to one embodiment, said medical instrument 60 comprises one articulated device 70 with two degrees of freedom of rotation orthogonal to each other to form a jointed wrist.

According to one embodiment, said medical instrument 60 comprises a jointed device 70 with at least three degrees of freedom. According to one embodiment, said jointed device 70 has three degrees of freedom of rotation, of which two degrees of freedom of rotation around axes parallel to each other and a third degree of freedom of rotation around said longitudinal axis of rotation r-r.

According to one embodiment, said jointed device 70 has three degrees of freedom of rotation, of which one first degree of freedom of rotation, around a first axis of rotation orthogonal to the axis of the instrument X-X, one second degree of freedom of rotation parallel to the first axis of rotation and a third degree of freedom of rotation orthogonal to the second axis of rotation, such that said second and third degrees of freedom of rotation are close to each other and form a sub-articulation of the wrist.

According to one embodiment, said medical instrument 60 comprises a jointed device 70, which has a further degree of freedom in its terminal portion 77, said further degree of freedom allows an opening and/or closing movement of said terminal portion 77. According to one embodiment, said jointed device 70 comprises a terminal device 77 in said distal portion, in which said terminal device 77 comprises said further degree of freedom of opening and/or closing. For example, said further degree of freedom determines the opening and/or closing of forceps or of a cutting instrument, such as scissors.

According to one embodiment, said medical instrument 60 comprises at least one shaft 65 such as to position its jointed device 70 at a predefined distance from said micro-positioning device 41. According to one embodiment, said shaft 65 is suitable for distancing said jointed device 70 from said micro-positioning device 41 by a predefined distance.

According to one embodiment, said predefined distance is a multiple of the longitudinal extension of said jointed device 70. According to one embodiment, said predefined distance is equal to at least five times the longitudinal extension of said jointed device 70. According to one embodiment, said predefined distance is equal to substantially twenty times the longitudinal extension of said jointed device 70. According to one embodiment said predefined distance is measured along the longitudinal direction of the shaft X-X. According to one embodiment, said predefined distance is equal to substantially fifty times the longitudinal extension of said jointed device 70.

According to one embodiment, said shaft 65 is suitable to connect to said frame with said terminal device 77 at a predefined distance from said frame 57.

According to one embodiment, said shaft 65 has a longitudinal extension between 30 mm and 250 mm, and preferably between 60 mm and 150 mm.

According to one embodiment, said shaft 65 has a longitudinal internal hole. According to one embodiment, said shaft 65 has a hollow tubular form.

According to one embodiment, said medical instrument 60 comprises a motor box 61 suitable to house at least one driving system of at least said jointed device 70, of said medical instrument 60. In this way, the actuation of said jointed device 70 happens internally to said medical instrument 60.

According to one embodiment, a robotic assembly 100 comprises at least one control device 20, suitable to determine the movement of at least one portion of said medical instrument 60, 160, 260, by a master-slave type communication system.

According to one embodiment, said assembly comprises a further control device 20, such that it comprises at least two input devices 20. According to one embodiment, said control device 20 is suitable to determine the motion of said jointed device 70 of said medical instrument 60. According to one embodiment, said control device 20 is suitable to determine the movement of said micro-positioning device 41. The provision of said characteristic allows a translational movement of said control instrument 21 as registered by said detection device 22 to be associated to a translational movement of said terminal device 77 within its workspace 7, 17.

According to one embodiment, said control device 20 is suitable to determine the motion of said micro-positioning device 41 and said medical instrument 60.

The provision of this characteristic allows to move at least a portion of said micro-positioning device 41 and at least a portion of said medical instrument 60 by means of said control instrument 21, such as to determine both rotational and translational movements of said terminal device 77 in said work volume 7.

According to one embodiment, said robotic assembly 100 is suitable to cooperate with a vision system 103 associable to said robotic assembly 100.

According to one embodiment, said vision system 103 is a microscope 103.

The provision of a microscope 103 associable to said robotic assembly allows for retro-fitting with pre-existing microscopes, making said robotic assembly 100 more versatile. For example, said robotic assembly 100 can be used in cooperation with microscopes that have a focusing distance between 100 mm and 500 mm, depending on the focal length of the objective lens used. Furthermore, it allows the swept volume of the robotic assembly 100 to be reduced, during the surgical operation given that it lacks as many parts as possible that require relatively large movements during the movement of the terminal portion of the instrument.

According to one embodiment, said microscope 103 is an optical microscope 103.

According to one embodiment, said microscope 103 is suitable to frame in its field of view said terminal portion 77 of said first medical instrument 160 and/or said terminal portion 77 of said second medical instrument 260 and/or said terminal portion of said third medical instrument 360.

According to one embodiment, said microscope 103 is suitable for framing the work volume 7.

According to one embodiment, at least one video-camera 45, is connected to said support member 38.

According to one embodiment, said video-camera 45 is suitable for framing said terminal portion 77 of said first medical instrument 160 and said terminal portion 77 of said second medical instrument 260.

According to one embodiment, said support 104 comprises at least one display 111, suitable to form a machine input interface.

According to one embodiment, said display 111 is suitable to visualize the images acquired by said video-camera 45.

According to one embodiment, said video-camera 45 is suitable to cooperate with said macro-positioning arm 30 to permit the correct positioning of said at least one medical instrument 60. The provision of this characteristic facilitates the positioning process of at least one portion of said at least one medical instrument 60 within the work volume 7.

According to one embodiment, said first medical instrument 160, said second medical instrument 260 and said support member 38 are disposed in such a way that they substantially form a triangle. Such provision allows to reproduce of the same triangulation existing between the eyes and the arms of the surgeon by means of said robotic assembly 100.

According to one embodiment, said support 104 is at least one of: a mobile cart, a support structure of a microscope, an operating bed, an operating table.

According to one embodiment, a control device 20 for microsurgery for a robotic assembly for microsurgery 100, in which said control device 20 is suitable to at least partially form the master interface of a master-slave pair for a robotic assembly for microsurgery 100, comprises:
- at least one control instrument 21, mobile in space, of a shape and size which lends it to being held and handled like a traditional surgical instrument, that is to say a surgical instrument suitable to operate directly on at least one portion of the patient anatomy 201,
- at least one detection device 22, suitable to detect the position of said control instrument 21 in at least on portion of space.

According to one embodiment said control instrument 21 comprises at least one position sensor 28, which cooperates with said detection device 22, to sense at least the position of said control instrument 21.

According to one embodiment, said detection device 22 generates an electromagnetic field such as to detect at least the position of said control instrument 21 by detecting the position of said at least one position sensor 28. According to one embodiment, said detection device 22 detects at least the position of said control instrument 21 by detecting the position of said position sensor 28 by measuring at least inertial accelerations components. According to one embodiment, said position sensor 28 comprises accelerometers.

According to one embodiment, said detection device 22 is positioned in a base structure 67 of said control device 20.

According to one embodiment, said control instrument 21 comprises at least one forceps articulation 69, effective in a tip portion 68 of said control instrument 21, such as to allow said tip portion 68 a grasping or cutting movement.

According to one embodiment, at least one tip sensor 29 measures an opening angle of said forceps articulation 69.

According to one embodiment, said control instrument 21 has a shape that substantially replicates the shape of a traditional surgical instrument.

According to one embodiment, said control device 20 comprises at least one ergonomic support element for the operator 27, comprising at least one support surface for the operator 25, suitable to support at least one portion of the forearm of the micro-surgeon 200, at least when in operating conditions, such as to provide ergonomic support for the micro-surgeon 200. The provision of such a characteristic allows for improved comfort of the micro-surgeon, determining an improved operating efficiency.

According to one embodiment, a robotic assembly 100, comprises:
- at least one control device 20, as described by one of the embodiments described above,
- at least one surgical micro-instrument 60, 160, 260, 360 comprising at least one terminal portion 77.

According to one embodiment, said terminal portion 77 is suitable to operate on at least one portion of the patient 201.

According to one embodiment, said terminal portion 77 is suitable to handle a surgical needle 202, as shown for example in FIG. 3A-3B.

According to one embodiment, said surgical micro-instrument 60, 160, 260 comprises at least one jointed device 70 and said control instrument 21 is suitable to cooperate with said jointed device 70, 170, 270 so that, when in operating conditions, a first movement of said control instrument 21 with respect to said detection device 22, corresponds to a second movement of said jointed device 70, 170, 270.

According to one embodiment, said macro-positioning arm 30 comprises at least one macro-positioning arm sensor, suitable to cooperate with said detection device 22, such as to detect the position in space of at least one portion of said macro-positioning arm 30 with respect to said detection device 22.

According to one embodiment, said microsurgical robotic assembly 100 is suitable to cooperate with a sensor, suitable to detect the position in space with respect to a single reference system of at least one of: said position sensor 28, said tip sensor 29, said macro-positioning arm sensor, said micro-positioning device sensor, said micro-instrument sensor. According to one embodiment, said microsurgical robotic assembly 100 is suitable to cooperate with a sensor, suitable to detect the position in space with respect to a single reference system of at least two of: said position sensor 28, said tip sensor 29, said macro-positioning arm sensor, said micro-positioning device sensor, said micro-instrument sensor. The provision of this characteristic allows for a teleoperation master-slave system to function adequately independently of the exact position of said detection device 22, said support 104, said macro-positioning arm 30 and said micro-positioning device 41. In other words, said medical instrument 60 is able to follow the movement of control instrument 21 with respect to a same common reference system of coordinates.

According to one embodiment, a microsurgical robotic assembly 100 also comprises:
a further control instrument 21, such as to comprise a first control instrument
and a second control instrument 221;
a further surgical micro-instrument 60, 160, 260 such as to comprise a first surgical micro-instrument 160 and a second surgical micro-instrument 260.

According to one embodiment, said microsurgical robotic assembly 100 comprises at least one further control device 20, such as to comprise a first control device 120 and a second control device 220.

According to one embodiment, said first control device 120 is suitable to form the master interface of said robotic assembly 100 for the first hand of the surgeon 200.

According to one embodiment, a medical instrument 60, 160, 260, 360 comprises at least one frame 57 and one jointed device 70.

According to one embodiment, said jointed device 70 comprises at least one first joint member 71, or first link 71, suitable to connect to at least one portion of said frame 57, and at least a second joint member 72, or second link 72, wherein said first link 71 is connected via a rotational joint 171 to said second link 72.

According to one embodiment, aid medical instrument 60 also comprises at least one tendon 90, 190, suitable for moving at least said second link 72 with respect to said first link 71, by pulling it.

According to one embodiment, at least one of said first link 71, said second link 72 comprises at least a sliding surface 40, 80, 140, 180, suitable to allow the sliding of at least one portion of said tendon 90, 190 over it.

According to one embodiment, said sliding surface 40, 80, 140, 180 is a ruled surface 40, 80, 140, 180, specifically a ruled surface formed by a plurality of portions of straight lines all parallel to each other and substantially parallel to a joint axis of movement P-P, Y-Y.

According to one embodiment, said sliding surface 40, 80, 140, 180 is a ruled surface 40, 80, 140, 180, specifically a ruled surface formed by a plurality of portions of straight lines all parallel to each other and substantially parallel to a joint axis of movement P-P, Y-Y of the rotational joint 171 closest to said sliding surface 40, 80, 140, 180. According to one embodiment, the closest rotational joint 171 is defined by measuring along the direction of the tendon path T-T.

According to one embodiment, said axes of joint movement can be fixed or mobile with respect to a base reference system.

According to one embodiment, said at least one second link 72 is a wrist member 78, and said wrist member 78 comprises at least one sliding surface 40, 80, 140, 180, formed by a plurality of portions of straight lines parallel to each other and substantially parallel to a first joint axis of movement.

According to one embodiment, said wrist member 78 comprises at least one jointing portion 172, suitable to form at least one portion of a second rotational joint 171 having a second joint axis of movement, not parallel to said first joint axis of movement.

According to one embodiment, said first joint axis of movement and said second joint axis of movement are substantially orthogonal to each other.

According to one embodiment, said first joint axis of movement is a pitch axis P-P.

According to one embodiment, said second joint axis of joint movement is a yaw axis Y-Y.

According to one embodiment, said medical instrument 60, 160, 260 has at least one terminal member 77.

According to one embodiment, said terminal member 77 is suitable to contact with one portion with a patient 201, when in operating conditions.

According to one embodiment, said terminal member 77 is suitable to handle a surgical needle 202.

According to one embodiment, said terminal member 77 comprises a cutting surface or blade and can act as a scalpel.

According to one embodiment, said terminal member 77 comprises at least one winding surface 86, made of a plurality of portions of straight lines all parallel to each other and substantially parallel to a joint axis of movement. According to one embodiment, said winding surface 86 is suitable to allow at least one portion of said tendon 90, 190 to be wound up around it.

According to one embodiment, said second joint member 72 is a terminal member 77.

According to one embodiment, said jointed device 70, 170, 270 comprises a third joint member 73, suitable to connect to at least said second joint member 72 by a rotational joint 171.

According to one embodiment, said third joint member 73 is a terminal member 77.

According to one embodiment, said terminal member 77 is connected to said wrist member 78 by a rotational joint 171.

According to one embodiment, said at least one joint member 72 is an elbow member 75, and said elbow member 75 comprises a plurality of sliding surfaces 40, 80, 140, 180 formed by a plurality of portions of straight lines all parallel to each other and substantially parallel to a single joint axis of movement.

According to one embodiment, said elbow member 75 comprises at least one jointing portion 172, suitable to form at least one portion of a rotational joint 171.

According to one embodiment, said jointed device 70 comprises a third joint member 73, suitable to be connected to at least said second joint member 72 by a rotational joint 171, in which said second joint member 72 is an elbow member 75 and said third joint member 73 is a wrist member 78.

According to one embodiment, said elbow member 75 is connected by a rotational joint 171 to said first joint member 71, and in which said wrist member 78 is connected via a rotational joint 171 to said elbow joint member 75.

According to one embodiment, said jointed device 70 comprises a fourth joint member 74, suitable to connect to at least said third joint member 73 via a rotational joint 171.

According to one embodiment, said fourth joint member 74 is a terminal member 77.

According to one embodiment, said terminal member 77 comprises at least one winding surface 86, formed by a plurality of portions of straight lines all parallel to each other and substantially parallel to a joint axis of movement, wherein said winding surface 86 is suitable to allow the winding of at least one portion of said tendon 90, 190 around it.

According to one embodiment, said jointed device 70 comprises said first member 71, connected to said wrist member 78 via a rotational joint 171, connected to said terminal member 77 via a rotational joint 171.

According to one embodiment, said jointed device 70 comprises said first member 71, connected to said elbow member 75 by a rotational joint 171, connected to said wrist member 78 by a rotation joint 171, itself connected to said terminal member 77 by a rotational joint 171. It should be apparent to those skilled in the art that making use of joint members similar to 71, 72, 73, a jointed device 70 can be assembled to include a serial sequence of members, of which from zero to a plurality of elbow joint members 75, a plurality of, preferably orthogonal, pairs of wrist joint members 78 and at least one terminal joint member 77.

According to one embodiment, said winding surface 86 is a ruled surface.

According to one embodiment, said winding surface is substantially unsuitable for said tendon 90, 190 to slide over it. This is because said tendon 90, 190 terminates close to said winding surface 86, on the joint member which comprises said winding surface 86.

According to one embodiment, said medical instrument 60 comprises at least one pair of tendons comprising one tendon 90 and one opposite tendon 190, and said tendon 90 and said opposite tendon 190 are suitable to connect their second termination endpoints 92, or second tendon termination 92, to respective tendon fastening points 82, or point of tendon termination 82, of said second joint member 72, such as to move said second joint member 72 around its joint axis in opposite directions.

According to one embodiment, said medical instrument 60 which comprises at least one pair of tendons comprising one tendon 90 and one opposite tendon 190, and said tendon 90 and said opposite tendon 190 are suitable to connect in their second termination endpoints 92 to respective tendon fastening points 82, or tendon termination features 82, of said terminal member 77, such as to move it around its joint axis in opposite directions.

The provision of such a feature makes sure that said tendon 90 and said opposite tendon 190 can work in an antagonistic fashion, for example both said tendon 90 and said opposite tendon 190 move said terminal member around the yaw axis Y-Y. Hence no passive or free joint movement can occur, and instead there are only positively guided and controlled movements.

According to one embodiment, said tendon 90 and opposite tendon 190 are suitable to connect by means of their second termination endpoints 92 to respective tendon fastening points 82, or tendon termination features 82, of at least one of said first, second, third and fourth joint members 71, 72, 73, 74.

According to one embodiment, said tendon 90 and opposite tendon 190 are suitable to connect by means of their second termination endpoints 92 in respective tendon fastening points 82, or tendon termination feature 82, of at least one of said elbow member 75, wrist member 78 and terminal member 77.

According to one embodiment, said medical instrument 60 comprises at least one shaft 65, suitable to guide said at least one tendon 90, 190. Said shaft 65 is a shaft according to one of any of the previously described embodiments.

According to one embodiment, said jointed device 70 has a longitudinal extension smaller than 10 millimeters.

According to one embodiment, said jointed device 70 has a volume inferior to 10 cubic millimeters.

According to one embodiment, said terminal member 77 comprises at least one first portion of terminal member 177 and at least a second portion of terminal member 277. According to one embodiment, said first portion of terminal member 177 and said second portion of terminal member 277, are mobile with respect to each other around a joint axis of movement such as to determine a grasping or cutting movement. According to one embodiment, said joint axis of movement is said yaw axis Y-Y.

According to one embodiment, said medical instrument 60, which comprises at least one pair of tendons, comprises a tendon 90 and an opposite tendon 190, in which one of said tendon 90 and said opposite tendon 190 is suitable to connect by means of its second endpoint 92 to a respective tendon fastening point 82, or tendon termination feature 82, p on said first terminal member 177, and in which the other one of said tendon 90 and said opposite tendon 190 is suitable to connect by means of its second endpoint 92 to a respective tendon fastening point 82, or tendon termination feature 82, on said second terminal member 277, such as to move said first portion of terminal member 177 and said second portion of terminal member 277 with movements in opposite directions.

According to one embodiment, each of said first portion of terminal member 177 and said second portion of terminal member 277 comprise at least one winding surface 86.

According to one embodiment, said medical instrument 60 comprises at least one pair of tendons comprising one tendon 90 and one opposite tendon 190, in which said tendon 90 and said opposite tendon 190 are suitable to connect by means of their second endpoints 92 in respective tendon fastening points 82, or tendon termination feature 82, of said terminal member 77, such as to move said third joint member 73 with respect to said fourth joint member 74 such as to determine a grasping or cutting movement.

According to one embodiment, said tendon 90 and said opposite tendon 190 wind their distal portions around at least one portion of said at least one winding surface 86 of terminal member 77.

According to one embodiment, said sliding surface 40, 80, 140, 180 is a lateral sliding surface 40, 140 suitable to extend away from the center volume of said jointed device 70, 170, 270 such as to determine that at least one portion of tendon is deflected away and runs not in contact with said jointed device 70.

According to one embodiment, said lateral sliding surface 40, 140 joins a surface of the member on which it is built, with at least a continuity surface 64, sharing a local tangent plane. According to one embodiment, said lateral sliding surface 40, 140 forms at least one sharp edge 63 with the member on which it is built.

According to one embodiment, said lateral sliding surface 40, 140 joins a surface of the member on which it is built with a continuity surface 64 on one side and on the other side forms one sharp edge 63 with the member on which it is built.

According to one embodiment, said sliding surface 40, 80, 140, 180 is a joint sliding surface 80, 180 that at least partially surrounds an axis of joint movement. According to one embodiment, said sliding surface 40, 80, 140, 180 is a joint sliding surface 80, 180 that at least partially surrounds at least one of said pitch axis P-P and said yaw axis Y-Y, and in which said joint sliding surface 80, 180 is oriented opposite with respect to at least one of said pitch axis P-P and said yaw axis Y-Y, such as to allow at least one intersection between the tendon path T-T of said tendon 90 and the tendon path T-T of said opposite tendon 190. In other words, said joint sliding surface 80, 180 is not suitable to face towards said joint axis of movement of the closest rotational joint 171, when in operating conditions.

According to one embodiment, said joint sliding surface is convex and partially surrounds at least one of said pitch axis P-P or yaw axis Y-Y, such as to permit at least one intersection of two opposite tendons on itself.

According to one embodiment, the term "closest joint" refers to the rotational joint 141 which is closest in distance to the sliding surface 40, 80, 140, 180 along the tendon path T-T.

According to one embodiment, on said joint sliding surface 80, 180 the tendon path T-T of said tendon 90 and the tendon path T-T of said opposite tendon 190, although they do not intersect, they at least partially overlap in a projection plane orthogonal to the direction of said axis of joint movement of the closest rotational joint 171.

According to one embodiment, on said joint sliding surface 80, 180 the tendon path T-T of said tendon 90 and the tendon path T-T of said opposite tendon 190 are distinct from each other and parallel on a projection plane parallel to the joint axis of movement of the closest rotational joint 171.

According to one embodiment, the tendon path T-T of said tendon 90 overlaps with the tendon path T-T of said opposite tendon 190 at least on a projection plane orthogonal to the direction of said joint axis of movement of the closest joint. According to one embodiment, the tendon path T-T of said tendon 90 is substantially parallel to the tendon path T-T of said opposite tendon 190 on a projection plane parallel to said joint axis of movement of the closest rotational joint.

According to one embodiment, the tendon path T-T of each tendon 90 are substantially parallel to each other, on a projection plane parallel to the said joint axis of movement of the closest rotational joint 171.

According to one embodiment, each tendon path T-T is substantially stationary over the joint member which it contacts. In other words, even when the tendon 90 is sliding, the overall tendon path T-T is substantially always in the same position with respect to the joint member of said medical instrument 60, which it contacts.

Such a feature is uniquely realized by provisioning that said sliding surface 40, 80, 140, 180 of said winding surfaces 86 has a cooperative geometrical relationship with said tendon termination feature 82, which is in turn fittingly positioned on a portion of said medical instrument.

According to one embodiment, said tendon path T-T remains substantially stationary over the joint member which it contacts for both tendon 90 and opposite tendon 190 that determines opposite joint movements.

According to one embodiment, the tendon path T-T of each tendon 90 is substantially stationary in its section over said frame 57, except for said deflectable portion 93. Said deflectable portion 93 is in fact suitable to be deflected by the pusher assembly 94, not unlike a guitar string.

According to one embodiment, said at least one tendon 90, 190, when in operating conditions, follows a tendon path T-T that is entirely composed of successive straight in-flight sections 9, which are not in contact with any sliding surface 40, 80 or winding surfaces 86, and curved sections which are in contact with sliding surfaces 40, 80 or winding surfaces 86 of the joint members 71, 72, 73, 74, 75, 77, 78.

According to one embodiment, each tendon termination feature 82 is positioned such as to support each tendon 90, 190 such that its tendon path T-T is stationary with respect to the joint member closest to it.

According to one embodiment, said tendon termination feature 82 is positioned such as to maintain its tendon path T-T of each tendon 90 substantially always in contact with said winding surface 86, when in operating conditions.

According to one embodiment, said tendon termination feature 82 is positioned such that the tendon path T-T of each tendon 90, 190 does not enter in contact with the tendon path T-T of any other tendon 90, 190, when in operating conditions.

According to one embodiment, said tendon termination feature 82 is positioned such that each tendon 90, when in operating conditions, slides on at least one sliding surface 40, 80, describing a curved section of the tendon path T-T substantially parallel to the curved section of the tendon path T-T described by any other tendon 90, 190 when it slides on the same sliding surface 40, 80.

According to one embodiment, said medical instrument 60 is a surgical instrument, suitable to be applied in at least one of the following fields: microsurgery, minimally invasive surgery and laparoscopic surgery.

According to one embodiment, said medical instrument 60 is suitable for being used for a biopsy. According to one embodiment, said medical instrument 60 is suitable to be used for an endoscopic procedure.

According to one embodiment, said tendon 90, 190 has a substantially circular cross section. According to one embodiment, the diameter of said tendon 90, 190 is variable in different portions of said tendon 90, 190. According to one embodiment, the mechanical properties of said tendon 90, 190 are variable in different portions of said tendon 90, 190. According to one embodiment, said tendon 90, 190 is obtained by joining portions of tendons with different characteristics. According to one embodiment, the composition of said tendon 90, 190 is variable in different portions of said tendon 90, 190.

According to one embodiment, said tendon path T-T in at least one portion of the tendon is substantially locally orthogonal to the generatrices of the sliding surface 40, 80, 140, 180 on which the tendon slides, in every operating condition, that is for any rotational angle of the rotational joints 171. These characteristics contribute to avoiding that said tendon path T-T of each of said tendons is ever deflected, that is to say that it never bends in a direction parallel to the axis of joint movement of the closest rotational joint 171.

According to one embodiment, said tendon path T-T is substantially locally orthogonal to the generatrices of the sliding surfaces 40, 80, 140, 180 on which it slides.

According to one embodiment, said jointed device 70 is primarily fabricated from metallic materials.

According to one embodiment, said joint members are suitable to be polished with the aim of further reducing the friction generated by the sliding of said at least one tendon, when said tendon slides over it.

According to one embodiment, a tendon drive system 50 for a medical instrument 60, 160, 260 comprises at least one pusher assembly 94.

According to one embodiment, said medical instrument 60, 160, 260 comprises a frame 57 and at least one tendon 90, 190, exclusively suitable to work under tensile loads applied at its endpoints, in which a tendon direction T-T is defined, or a tendon path T-T, substantially coinciding with the direction of longitudinal development of said tendon 90, and in which said tendon 90 is fastened at its first endpoint 91, or proximal tendon endpoint 91, or first tendon termination 91, to said frame 57.

According to one embodiment, said pusher assembly 94 is suitable to apply a force over at least one portion of said deflectable portion 93 of said tendon 90 along a pushing direction transversal to the tendon path T-T such as to deflect the tendon path T-T and induce an increased tensile load in said tendon 90.

When said pusher assembly pushes in said pushing direction, transversal to the tendon path T-T, it tends to lengthen locally, only locally, said tendon path. Such a localized path lengthening, which create a larger, local tendon loop is directly related to the amount of advancement of the pusher assembly. The creation of such a larger local tendon loop results at the opposite end of the tendon, in a proportional moving back of the distal endpoint of the tendon 92 which is fastened to the tendon termination feature 82 on the joint member and hence results in a movement of the joint member.

According to one embodiment, said tendon 90 also comprises a second tendon endpoint 92, or distal tendon endpoint 92, suitable to pull a mobile element, which can be connected to said second distal tendon endpoint 92.

According to one embodiment, following said tendon along its tendon path T-T one first encounters said first tendon endpoint 91, then said at least tendon deflectable portion 93, and then said second tendon endpoint 92.

According to one embodiment, said mobile element is at least one portion of said medical instrument 60, 160, 260, which is mobile with respect to said frame 57.

According to one embodiment, when said tendon deflectable portion 93 is deflected by said pusher assembly 94, said tendon 90 determines the movement of at least one portion of said jointed device 70 with respect to said frame 57.

According to one embodiment, said pusher assembly 94 also comprises at least one sterile barrier 87, suitable to substantially impede mutual bacterial contamination of the two environments it separates.

According to one embodiment, said sterile barrier 87 is placed between said pushing element 95 and said plunger 96.

According to one embodiment, said sterile barrier is of a form and material suitable to transmit the push of said pushing element 95 to said plunger 96.

According to one embodiment, said drive system 50 comprises at least two tendon guiding elements 97, or guiding pulleys, positioned along said tendon direction T-T such that when said pusher assembly determines a deflection of said tendon path T-T, said at least said two tendon guiding elements 97 cooperate to confine the deflection of said tendon path T-T to the tendon path section between said two guiding elements 97.

According to one embodiment, said plunger 96 comprises at least one plunger idle pulley 98, suitable to push on said tendon deflectable portion 93, and in which said plunger idle pulley 98 is suitable to freely turn around its axis, and in this way to reduce the sliding friction over said tendon deflectable portion 93 at least when pushed by said plunger 96.

According to one embodiment, said plunger idle pulley 98 is a ball bearing.

According to one embodiment, said second tendon endpoint 92 is a boss or a loop or a knot.

According to one embodiment, said tendon drive system 50 comprises at least one pretensioning element 99, suitable for maintaining said tendon 90 pretensioned.

According to one embodiment, said tendon drive system 50 comprises at least one further pusher assembly 94, or opposite pusher assembly 194, opposed to said pusher assembly 94 and suitable to push on at least one portion of tendon deflectable portion 93 of said opposite tendon 190, along a transversal pushing direction of tendon T-T such as to deflect the tendon path T-T and to induce an increased tensile load in said opposite tendon 190 and said tendon 90. In other words, said tendon 90 and said opposite tendon are suitable to work opposed to each other like antagonistic muscles of the human body that cooperate to determine the adduction and abduction movements of a joint.

According to one embodiment, said opposite pusher assembly 194 pushes on said tendon deflectable portion 93 of said opposite tendon 190 along a pushing direction transversal to said tendon path T-T, deflecting said tendon path T-T, inducing tensile load in said opposite tendon 190, from its proximal portion 18 and inducing tensile load in said tendon 90, from its distal portion 19.

According to one embodiment, said opposite tendon 190 comprises a second endpoint 92, or distal endpoint 92, suitable to pull a mobile element associable to said second tendon endpoint 92 of said opposite tendon 190.

According to one embodiment, said opposite tendon 190 comprises a second endpoint 92, or distal endpoint suitable to pull a common, single mobile element, associable to both said second tendon endpoint 92 of said tendon 90 and said second tendon endpoint 92 of said opposite tendon 190. According to one embodiment, said tendon 90 and said opposite tendon 190 have lengths such that said common, single mobile element is in a reference position when said tendon 90 and said opposite tendon 190 are pretensioned by their respective pretensioning elements.

According to one embodiment, said tendon 90 and said opposite tendon 190 are two portions of a single tendon 90.

According to one embodiment, said tendon drive system 50 comprises an opposite pretensioning element 199, suitable for maintaining said opposite tendon 190 pretensioned.

According to one embodiment, said plurality of tendons 90 and said plurality of opposite tendons 190 are positioned on a portion of a drum 59, or drum 59, of said frame 57 such that the tendon path T-T of each tendon 90, 190 runs separate with respect to the path of all other tendons 90, 190.

According to one embodiment, said plurality of tendons 90 and said plurality of tendons 190 are positioned substantially radially, or as rays, on said drum 59. According to one embodiment, said plurality of tendons 90 and said plurality of opposite tendons 190 are configured one said drum 59 like a cylinder of a radial engine, and in which the paths of said tendon 90 and said opposite tendon 190 do not cross each other on said drum 59.

According to one embodiment, said tendon 90 is fabricated in a material that is less hard than the material of said jointed device 70. The provision of this characteristic allows the fabrication of a medical instrument 60 comprising a jointed device 70 with greater resistance to wear, caused by the sliding of tendon 90 over at least a portion of said jointed device 70. Furthermore, this characteristic avoids any wear and loss of material of the surface of the jointed device 70 over which the tendon slides. In other words, the provision of this characteristic avoids said jointed device 70 from becoming scratched due to the effects of the tendon 90 sliding over it, when in operating conditions.

According to one embodiment, said tendon 90, 190 is made of polyethylene. According to one embodiment, said tendon 90, 190 is made of high molecular weight polyethylene, or UHMWPE. According to one embodiment, said tendon 90, 190 is made of Kevlar. According to one embodiment, said tendon 90, 190 is made of Vectran. According to one embodiment, said tendon 90, 190 is made of Zylon, or PBO. According to one embodiment, said tendon 90, 190 is made of a combination of the above materials.

According to one embodiment, said tendon 90 comprises at least one tendon endpoint 91, suitable to be glued to said frame 57.

A method for the fabrication of said medical instrument 60, 160, 260 is described below.

According to one possible operating mode, a fabrication method for the medical instrument 60, 160, 260 comprises a phase of fabrication of a medical instrument 60, 160, 260 according to one of any embodiments previously described, by at least one additive manufacturing technique.

According to one possible operating mode, a fabrication method of a medical instrument 60, 160, 260 comprises a phase of fabrication a medical instrument by micro-injection molding. In other words, a fabrication method for the medical instrument 60, 160, 260 comprises a phase of fabrication of a medical instrument by means of micromolding.

A fabrication method of the jointed device 70, 170, 270 is described below.

According to an embodiment, a fabrication method of a jointed device 70, 170, 270 comprises at least the following phases, in the preferred order indicated below:
(A''') provide a machining fixture 112 on an EDM machine and arrange a plurality of workpieces 117 on said machining fixture 112.
(B''') cut the desired geometry on said workpieces 117 with cutting lines parallel to each other.

The provision of a single cutting step on said workpieces with cutting lines parallel to each other, allows the machining of surfaces that are parallel to each other on said workpieces, with an extreme precision of parallelism.

According to one possible operating mode, the machining method described above allows the machining of ruled surfaces characterized by parallel generatices on said workpieces 117.

According to one possible operating mode, one machining method as described above allows the cutting of workpieces of very small dimension, for example of millimetric or sub-millimetric dimensions.

According to one embodiment, said machining method is suitable to fabricate at least one jointed device 70 that comprises a plurality of joint members 71, 72, 73, 74, 75, 76, 77, 78.

According to one possible operating mode, said machining method is suitable to machine parallel cuts on said workpieces 117 such as to form joint members comprising surfaces parallel to each other.

According to one possible operating mode, said machining method is suitable for machining parallel cuts on said workpieces 117 such as to form joint members suitable to be assembled in a complementary fashion because they comprise surfaces that are parallel to each other.

According to one possible operating mode, said EDM machine is suitable to perform wire EDM and comprises a cutting wire 115.

According to one embodiment, said cutting wire 115, or EDM wire 115, or electrical discharge machine wire 115 is of a diameter between 30 microns and 100 microns, and is preferably of 50 microns.

The provision of a machining method as described above allows exclusively thermal energy to be transferred to the piece being machined 117, avoiding any mechanical energy to be transferred to the piece being machined 117, for example inducing flexion, as it is the case when carrying out cuts with a milling machine.

According to one embodiment, said machining method is suitable to fabricate at least one jointed device for applications in the medical-surgical sector.

According to one embodiment, said machining method is suitable to fabricate at least one jointed device, suitable for applications in precision mechanics, for example suitable for use in watchmaking. According to one embodiment, said machining method is suitable to fabricate at least one jointed device, suitable for applications in the jewelry and/or fashion jewelry sector.

According to one embodiment, said machining method is suitable for the fabrication of at least one jointed device, suitable for applications in the assembly of electromechanical products.

According to one possible operating mode, the phase (A''') comprises the following sub-phases:
mount a plurality of workpieces on said machining fixture 112 in their respective member seats 116.

According to one possible operating mode, a sub-phase is first carried out during said phase (A'''):
(A1''') provide a machining fixture 112 on an EDM machine; and then the sub-phase:
(A2''') arrange a plurality of workpieces 117 on said machining fixture 112.

According to a possible operating mode, one method comprises the following further phase between the sub-phase (A1''') and the sub-phase (A2'''):
(C''') carry out a calibration.

According to one possible operating mode, one method comprises the following further phase between the phase (A''') and the phase (B'''):
(C''') carry out a calibration.

According to one possible operating mode, one method comprises the following further phases after the phase (B''').
(D''') rotate said machining fixture 112.
repeat said phase (B''').

According to one possible operating mode, said phase of rotating said machining fixture 112 comprises a further phase of using a rotary table to rotate said machining fixture 112, avoiding to dismount said machining fixture 112 from the cutting machine to carry out the following phases:
rotate said machining fixture 112;
carry out a second calibration, or cut calibration, exclusively on said reference rod 118,
repeat said phase (B''').

According to one possible operating mode, said phase (C'''), carry out a calibration, comprises the following sub-phases:
switch on the EDM machine;
provide a reference rod 118 with its axis parallel to said member seats 116 of the workpieces 117;
bring said cutting wire 115 in contact with a first portion 122 of said reference rod 118, or portion facing towards the side of wire approach 122;
measure, or register, the position of said wire;
and/or
measure, or register, the position of said cutting wire 115, when it is in contact with a first portion of a first workpiece to be machined, or the portion facing the side of wire approach; execute the previous phase for each workpiece 117;

and/or
- bring the cutting wire 115 in contact with a second rod portion 123 of said reference rod 118, or portion facing the side of wire departure 123, opposite with respect to said first rod portion 122;
- measure, or register, the position of said cutting wire 115;
- compute the position of the axis of said reference rod 118 as a midpoint between the position of said wire when in contact with said first rod portion and the position of said wire when in contact with said second rod portion.

and/or
- measure, or register, the position of said cutting wire 115 when in contact with a second portion of said first workpiece, or the portion facing the side of wire departure;
- compute the position of said first workpiece as a midpoint between the position of said wire when in contact with said first portion of the workpiece and the position of said wire when in contact with said second portion of the workpiece;

and/or
- execute the previous phase for each workpiece 117;

and/or
- repeat the procedure for all cutting planes X-Y, Y-Z, X-Z.

According to one embodiment, said machining fixture 112 of a jointed device 70, 170, 270 is suitable to be mounted on a machine for EDM.

According to one embodiment, said machining fixture 112 is suitable to perform at least two cuts on different cutting planes on workpieces 117 by using a single cutting profile 110 per cutting plane.

According to one realization, said machining fixture 112 comprises a first pair of fixing surfaces 113, 114, which are rectified, opposite and substantially parallel to each other and substantially orthogonal to a first plane of cutting X-Y.

According to one embodiment, said machining fixture 112 comprises a second pair of fixing surfaces 134, 135, which are rectified, opposite and substantially parallel to each other and substantially orthogonal to a second plane of cutting Y-Z.

According to one embodiment, said first pair of fixing surfaces 113, 114 and said second pair of fixing surfaces 134, 135 are rectified.

According to one embodiment, each pair of locating surfaces comprises at least one base fixing surface 113, 135 and at least one fixture fixing surface 114, 134.

According to one embodiment, said plurality of member seat 116 are sequentially arranged such that a translating straight line, substantially orthogonal to said first cutting plane X-Y, or substantially orthogonal to said second cutting plane Y-Z, would intersect at most only one of said workpieces 117 at a time, when said workpieces are mounted in respective member seats 116.

According to one embodiment, said member seats 116 are substantially parallel to each other.

According to one embodiment, said machining fixture 112 also comprises a pair of locating surfaces, opposite and substantially parallel to each other and substantially orthogonal to a third cutting plane X-Z.

According to one embodiment, said third pair of locating surfaces comprises at least a guide hole 125, and the EDM wire 115 of said EDM machine is inserted in at least one said guide hole 125, to avoid the EDM wire coming into contact with at least one machining fixture 112, during the cut.

According to one embodiment, said machining fixture 112 also comprises:
- a plurality of member seats 116, each suitable to receive at least one workpiece 117, said workpiece 117 being suitable to realize at least one portion of said jointed device 70, 170, 270.

According to one embodiment, said machining fixture 112 also comprises at least one reference rod 118, suitable to allow for the cut calibration.

According to one embodiment, said machining fixture 112 comprises at least one fixing element, or fastening element, suitable to firmly connect said at least one workpiece 117 in its respective member seat 116.

According to one embodiment, said at least one fastening element is conductive glue.

According to one embodiment, said at least one fastening element is a grub screw.

According to one embodiment, said grub screw is suitable to be mounted in a threaded hole supplied in said at least one fastening surface.

According to one embodiment, said fastening grub screw, is suitable to penetrate in said threaded hole of said fastening surface.

According to one embodiment, said machining fixture 112 comprises four member seats 116 and a reference rod 118.

According to one embodiment, each member seat 116 is substantially positioned at the same distance from its respective fastening surface.

According to one embodiment, said fastening surfaces are positioned in a stepwise manner, such as to form a stair shape in profile. In other words, said fastening surfaces are positioned in a stepwise manner, such as to form a stair shape in profile with respect to at least one cutting plane X-Y, Y-Z, X-Z.

According to one embodiment, said machining fixture 112 has a surface facing towards any cutting plane X-Y, Y-Z, X-Z inferior to 10000 square millimeters.

According to one embodiment, said machining fixture 112 has a surface facing towards any cutting plane X-Y, Y-Z, X-Z inferior to 5000 square millimeters.

According to an embodiment, a shaft angle $\theta$ is defined as the angle between the shaft direction X-X of the shaft 65 of said first medical instrument 160 and the shaft direction X-X of the shaft 65 of said second medical instrument 260.

According to an embodiment, a medical instrument 60, 160, 260, 360 includes:
- at least a joint member 71, 72, 73, 74 of a jointed device 70,
- a frame 57 including a shaft 65
- a tendon 90, 190 suitable to move said joint member 71, 72, 73, 74 with respect to said frame 57
- a plunger 96 mobile along a degree of freedom with respect to said frame 57, in contact with said tendon 90, 190 and suitable to actuate said tendon 90, 190
- a pushing element 95 mobile along a linear trajectory and including an actuator
- a sterile barrier 87 suitable to substantially impede mutual bacteria contamination of the two environments it separates, placed between said pushing element 95 and said plunger 96,
- wherein said plunger 96 is free to move away from said sterile barrier 87 and/or pushing element 95 and said pushing element 95 pushes on said sterile barrier 87 bringing it in contact with said plunger 96 and thus moves said plunger 96.

According to one embodiment, said pushing element 95 pushes on a plunger 96 in a pushing direction directed towards the inside of said frame 57, to move said plunger 96 along its degree of freedom with respect to said frame 57.

According to one embodiment, said pushing element 95 exchanges with said plunger 96 a force that is always directed in said pushing direction. In other words, said pushing element 95 is not suitable to exchange with said plunger 96 a pulling force, in other words said pushing element 95 cannot pull said plunger 96.

According to one embodiment, said pushing element 95 includes a lead screw and nut type actuator.

According to one embodiment, said actuator includes a ball screw.

According to one embodiment, said pushing element 95 includes a piston.

According to one embodiment, said plunger 96 has two portions one first portion of plunger 145 suitable to be in contact with said pushing element 95 and one second portion of plunger 146 to suitable to be in contact with said tendon 90, 190.

According to one embodiment, said first portion of plunger 145 is exposed from the frame 57 to be pushed by said pushing element 95.

According to one embodiment, said first portion of plunger 145 extends outside of frame 57 to be accessible by said pushing element 95.

According to one embodiment, said first portion of plunger 145 is flush with said frame 57 to be accessible by said pushing element 95.

According to one embodiment, said first portion of plunger 145 includes a pushing surface 147 suitable to be engaged with said pushing element 95.

According to one embodiment, said pushing elements 95 has a reciprocal pushing surface 148

According to one embodiment, said pushing element 95 pushes said plunger 96 transmitting a linear force through said a reciprocal pushing surface 148.

According to one embodiment, said pushing element 95 includes at least one pushing element idle pulley not represented, suitable to push on said pushing surface 147.

According to one embodiment, said pushing element 95 pushes said plunger 96 transmitting a linear force through said one pushing element idle pulley.

According to one embodiment, said pushing surface 147 and reciprocal pushing surface 148 are flat.

According to one embodiment, said pushing surface 147 and reciprocal pushing surface 148 are curved surface that mate with each other.

According to one embodiment, said pushing surface 147 and reciprocal pushing surface 148 are sliding surfaces that slide with respect to each other as said pushing element 95 moves along a linear trajectory.

According to one embodiment, said second portion of plunger 96 in contact with said tendon 90, 190.

According to one embodiment, said medical instrument 60, 160, 260, 360 includes at least one tensioning element 99, suitable for impose a preload on said tendon 90.

According to one embodiment, said tensioning element 99 is a spring.

According to one embodiment, said tensioning element 99 is suitable to apply a force between the frame 57 and the plunger 96, in the direction of moving said plunger 96 so as to impose a preload on said tendon 90.

According to one embodiment, said tensioning element 99 is suitable to apply a force between the frame 57 and the plunger 96, in the direction of moving said plunger 96 away from said pushing element 95.

According to one embodiment, said tensioning element 99 is suitable to apply a force between the frame 57 and the plunger 96, in the direction of moving said plunger 96 towards the inside of said frame 57.

According to one embodiment, said preload is substantially proportional to the compression movement of said spring 99.

According to one embodiment, said second portion of plunger 146 pushes on at least one tendon deflectable portion 93 of said tendon 90.

According to one embodiment, said tendon deflectable portion 93 of said tendon 90 extends from a first guiding pulley 197 and second guiding pulley 297.

According to one embodiment, said second portion of plunger 146 moves in a space provided between said a first guiding pulley 197 and said second guiding pulley 297.

According to one embodiment, said plunger 96 changes the length of tendon 90 path between said a first guiding pulley 197 and said second guiding pulley 297 of an amount linearly proportional to the plunger 96 motion along said degree of freedom of plunger 96 with respect to said frame 57.

According to one embodiment, said second portion of plunger 146 includes at least one plunger idle pulley 98, suitable to push on said tendon deflectable portion 93, According to one embodiment, said tendon 90 has a first tendon endpoint 91 fastened to said joint member 71, 72, 73, 74.

According to one embodiment, said tendon 90 has a second tendon endpoint 91 fastened to said frame 57.

According to one embodiment, said first tendon endpoint 91, is fastened to said second portion of plunger 146, instead than to said frame 57.

According to one embodiment, said frame 57 includes a upper frame portion 58 and a lower frame portion 59 the latter including a shaft 65.

According to one embodiment, said plunger 96 is mobile along a degree of freedom with respect to said frame 57.

According to one embodiment, said plunger 96 is jointed to said upper frame portion 58 with a linear joint.

According to one embodiment, said plunger 96 is jointed to said lower frame portion 58 with a rotational joint not represented.

According to one embodiment, said plunger 96 moves linearly along a degree of freedom with respect to said frame 57.

According to one embodiment, said plunger 96 is maintained in a proper alignment by means of linear bushings not represented inserted in the first frame section 58.

According to one embodiment, said plunger 96 is maintained in a proper alignment with upper frame 58 by means of respective shoulder surfaces 88.

According to one embodiment, said plungers 96 is a rocker that rotates around a pivot of said frame 57.

According to one embodiment, said sterile barrier 87 is of a form and material suitable to transmit the push of said pushing element 95 to said plunger 96.

According to one embodiment, said sterile barrier 87 is a flexible continuous layer of material.

According to one embodiment, said sterile barrier 87 lays in between said pushing element 95.

According to one embodiment, said sterile barrier 87 is trapped between said pushing surface 147 and said reciprocal pushing surface 148.

According to one embodiment, said medical instrument 60, 160, 260, 360 includes a plurality of tendons 90 and of pairs of plungers 96 and associated pushing element 95.

According to one embodiment, said sterile barrier 87 is a flexible continuous layer of material.

According to one embodiment, said sterile barrier 87 is trapped between each plunger 96 and associated pushing element 95.

According to one embodiment, said sterile barrier 87 is made of a stretchable material that stretches as said plungers 96 move with respect to said frame 57 exerting forces that do not substantially impede the motion of said plungers 96.

According to one embodiment, said sterile barrier 87 is a drape.

According to one embodiment, said sterile barrier 87 is a loose fitting drape that stretches as said plungers 96 move with respect to said frame 57 exerting forces that do not substantially impede the motion of said plungers 96.

Due to the provision of a pushing element 95 of a medical instrument 60, 160, 260, 360 according to one aspect of the invention, suitable to move a jointed device across a sterile barrier allows the production of a medical instrument, which is highly reliable and sterile.

Due to the provision of a plunger 96 of a medical instrument 60, 160, 260, 360 according to one aspect of the invention, it is possible to employ a simple sterile barrier in a shape of a drape or continuous flexible sheet of material.

Due to the provision of a plunger 96 of a medical instrument 60, 160, 260, 360 according to one aspect of the invention, it is possible to increase the precision of the commanded motion using pushing elements with high precision linear actuators.

Due to the provision of a plunger 96 of a medical instrument 60, 160, 260, 360 according to one aspect of the invention, it is possible to protect the tendons 90 inside said frame 57 while allowing sterile barrier 87 to be external to said frame.

Due to the provision of a plunger 96 of a medical instrument 60, 160, 260, 360 according to one aspect of the invention, it is possible to provide tensioning to said tendons 90, 190 for any joint member 71 position of said jointed device 70.

Due to the provision of a plunger 96 of a medical instrument 60, 160, 260, 360 according to one aspect of the invention, it is possible to avoid lost motion and backlash effects associated to changes of direction of motion of which are altogether avoided making use of a continued pushing action of said pushing element on said plunger.

Due to the provision of a sterile barrier 87 of a medical instrument 60, 160, 260, 360 according to one aspect of the invention, it is possible to provide a sterile barrier that is not attached to pushing element and so it is easier to deploy for the surgical staff.

According to one embodiment, said pushing element 95 includes a sensor 150.

According to one embodiment, said pushing element 95 includes a sensor 150 suitable to detect contact between said pushing element 95 and said plunger 96 through said sterile barrier 87.

According to one embodiment, said pushing element 95 includes a force sensor 151 suitable to measure the pushing force exchanged between said pushing element 95 and plunger 96 through said sterile barrier 87.

According to one embodiment, said force sensor 151 is a mono-axial load sensor measuring a component of pushing force along the linear trajectory of motion of said pushing element 95.

According to one embodiment, said pushing element 95 includes a pressure sensor 152 suitable to measure the pressure exchanged between said pushing element 95 and plunger 96 through said sterile barrier 87.

According to one embodiment, said pressure sensor 152 is a thin film pressure sensor glued to said reciprocal pushing surface 148 of said pushing element 95.

According to one embodiment, said pushing element 95 includes a non contact proximity sensor 153 suitable to measure the distance between said reciprocal pushing surface 148 and pushing surface 147 through said sterile barrier 87.

Due to the provision of a pushing element 95 of a medical instrument 60, 160, 260, 360 according to one aspect of the invention, suitable to move a jointed device across a sterile barrier allows the production of a medical instrument, which is highly reliable and sterile.

Due to the provision of a sensor 150 of a medical instrument 60, 160, 260, 360 according to one aspect of the invention, it is possible to sense through a sterile barrier a sensed quantity related to the interaction between said jointed device 70 and patient 201 anatomy.

Due to the provision of a sensor 150 of a medical instrument 60, 160, 260, 360 according to one aspect of the invention, it is possible to detect contact between said pushing element 95 and plunger 96 through a sterile barrier.

Due to the provision of a sensor 150 of a medical instrument 60, 160, 260, 360 according to one aspect of the invention, it is possible to sense a pushing force through a sterile barrier related to tension of tendon 90, 190.

According to one embodiment, each control device 20 is equipped with a support clamp or bracket, which can be independently positioned, for example by connecting it to the operating table 102. Said control devices 20 are connected to the surgical robotic assembly 100 by a power cable 107, also suitable for the transmission of control data.

According to one embodiment, to simplify the transport of the surgical robotic assembly 100, a retractable handle 106 and a foot platform 105 are positioned on a posterior side. The cart 104 has a control panel 108 on a posterior surface for the management of the parameters of the surgical robotic assembly 100 by the user and for the display of messages or warnings of the machine itself. On/Off switches (power buttons) and an emergency stop button are present on the same side. A power cable 107 supplies electrical current to the entire system, while the video data acquired by the digital microscope are passed to the surgical robotic assembly 100 via a communication cable 109, such as to be able to integrate vision-derived information into the controls. According to one embodiment, said surgical robotic assembly 100 comprises a foot platform 105, suitable to be used together or alternatively to a retractable handle 106 for the transport of the robotic assembly 100 during its positioning in the operating room, placed on the bottom of the posterior side of the cart.

Said foot platform 105 allows the foot of an operator responsible for the movement of said robotic assembly 100 to rest on it, such that the robotic assembly 100 can also be pushed from the base, eliminating the risk of its tipping over while it is moved.

According to one embodiment, at least one tendon 90 winds around at least four guiding pulleys 197, 297, 397, 497, thus defining a third guide element 397 and a fourth guide element 497. Between said third guide element 397 and said fourth guide element 497, a tendon guide element 89 keeps the tendon 90 in the correct position and avoids derailing of the tendon 90, even in cases such as an anomalous loss of tension.

According to one embodiment, the joint members that form the jointed device 70, 170, 270 and its terminal device 77, reproduce the kinematics of the human wrist adding a grasping degree of freedom of movement at the tip, for a total of three degrees of freedom of movement.

According to one embodiment, a first joint member 71 and a second joint member 72 are connected to each other by a rotational joint 171 around a first axis of rotation P-P, followed by a first portion of the terminal member 177 and a second portion of the terminal member 277, both connected to said second joint member 72, which freely rotate around a second axis of joint movement Y-Y, orthogonal to the first axis of joint movement P-P and providing a terminal device 77 at the tip.

According to one embodiment, the first member 71 locks on or is jointed in a concentric manner with the shaft 65 of the medical instrument 60 and is rigidly attached to it via fastening pins 76.

According to one embodiment, the members that make up the jointed device 70 are in fact rotationally connected to each other by a axis support feature of the rotational joint 171. Each member has joint sliding surfaces 80, or joint winding surfaces 86 for the tendons 90, both around the joint axis of movement P-P, Y-Y and along its body.

According to one embodiment, all members that form the jointed device 70 and the terminal device 77 are fabricated by a wire EDM performed on two orthogonal work planes X-Y, Y-Z.

According to one embodiment, fabricating the first member 71 starting from a cylindrical piece to be machined 117, said first member presents two circular surfaces that allow its concentric insertion into the shaft 65.

According to one embodiment, said circular surfaces present mating features on a lower portion, such as through-holes, that permit the rigid attachment of said first member of shaft 65 by means of fastening pins 76. Said first member 71 presents on a distal portion two features to support rotational joint 171, each characterized by a cylindrical seat centered around said first axis of joint movement P-P and a lateral shoulder surface.

According to one embodiment, all holes, being machined by wire EDM such as the pin holes 79, have extra machining grooves 49 resulting from the passage of the cutting wire 115.

According to one embodiment, having defined said first section plane containing the axis of the instrument X-X and the first joint movement axis P-P, the first member 71 presents two opposite tendon sliding surfaces 40, 140 each having rounded shapes that are symmetrically opposite i.e. mirrored with respect to said section plane.

According to one embodiment, being machined by wire EDM, each sliding surface 80, 180, 40, 140 is resulting from the sweeping motion of parallel straight generatrices that move directly along a cutting profile 110.

According to one embodiment, the actuation cables 90 slide in two groups of three, respectively along the two lateral sliding surfaces 40, 140, one opposite to the other on the first member 71 and they cross said section plane before the first axis of rotation to then continue onto second member 72.

According to one embodiment, said second member 72 has a joint sliding surface 80 proximally, arranged around said first axis of joint movement P-P having a cylindrical portion.

According to one embodiment, said joint sliding surface 80 is formed by parallel straight generatrices following the wire EDM cutting profile.

According to one embodiment, a pin holding feature 76 and a lateral shoulder surface characterize the joint of the first member 71 around the first axis of joint movement P-P. Two tendon termination features 82 are laterally derived from the second member 72 allowing the fastening of second tendon endpoint 92 of the second member by knot or gluing. Distally, two support features for the third and fourth rotational joint are each characterized by a pin hole 79 around the second axis of joint movement Y-Y and a lateral shoulder surface.

According to one embodiment, the second axis of joint movement Y-Y is orthogonal to the first axis of joint movement P-P. Being machined by wire EDM, the pin hole 79 has machining grooves 49, resulting from the cutting wire 115.

According to one embodiment, the third member 73 is characterized by a pin hole 79 located around the second axis of joint movement Y-Y. The third member 73 is mated to the second member 72 by a seat for a joint pin and an associated lateral shoulder surface. A winding surface 86 of the actuation cables 90, 190 allows the winding of the actuation cables 90, 190 around that winding surface 86 that is concentric to the second axis of joint movement Y-Y.

Laterally to the third member 73 a tendon termination feature 82 and tendon fastening points 82 are derived. The tendon termination feature 82 allows the passage of the tendons 90, and the tendon fastening point 82 holds the second tendon endpoint 92, 192 of the third member 73, defined by knots.

According to one embodiment fastening pins 76 are inserted in the pin holes 79 of the members of the jointed device 70. The fastening pins 76 are preferentially made of hard metal, rectified and polished to reduce sliding friction.

A method for machining tridimensional, assemblable mechanical micro-components by EDM is described below. In particular it regards the fabrication of jointed devices 70 of a characteristic outer diameter inferior to 4 mm for application in micro-surgery. Furthermore, the main characteristics of a specific machining fixture 112, which is a fundamental element for the set up of a production process in an economically sustainable fashion and which is capable of guaranteeing the required precision, are described below.

According to one embodiment, the need to produce micro-parts with many mechanical details and a high level of precision requires the use of hard metals as a structural material and requires wire EDM as the machining process for the parts. As is known, EDM is a subtractive fabrication process in which material is removed by a conductive piece with a series of current discharges between the piece itself and an electrode kept at an electrical voltage difference, separated by a dielectric liquid such as water or oil, until the desired shape is obtained. In particular, during wire EDM machining, the workpiece 117 is held fixed and is immersed in a bath of dielectric liquid while a metal cutting wire 115, made of copper or brass for example, and of a diameter varying between 0.5 mm and 0.02 mm, continuously runs between two bobbins. The cutting wire 115 is sustained by an upper guide and a lower guide, which being driven by a computer numeric control system in the horizontal plane, carry out two-dimensional cutting profiles. The movement of the guides is very precise, and the overall machining resolution is close to 1 micron ($\mu$m), nevertheless, the planar cut substantially limits the fabrication of three-dimensional parts. Despite the fact that some advanced machines have an upper guide, which can move independently in the horizontal plane, the ability to produce complex 3D parts has not substantially increased.

The primary advantages of wire EDM comprise:
the possibility of machining hard metals,
absence of direct contact between the tool and the piece to be machined 117
delicate details can be machined without distortion,
a good superficial finish can be obtained,
complex shapes, otherwise difficult to produce with conventional cutting instruments can be produced, while maintaining very low tolerances.

The manual phases for the fastening each single, metallic workpiece to be machined 117 to the machine for each of the cutting planes and the following calibration of the machine itself, are very slow phases during the fabrication of the parts and are also the phases which result in the greatest geometric errors that hinder the perfect mating between micro-parts produced individually.

According to one embodiment, in order to substantially decrease the fabrication time and guarantee the precision required for the correct mating of the fabricated micro-parts, a machining fixture 112 is provided, which intended specifically for this use. It provides a mechanical support, which allows the simultaneous fastening and machining of all the workpieces 117, simplifying assembly of at least a portion of a jointed device 70 on one or more difference planes, with a single cutting profile 110 and a single calibration step.

According to one possible operating mode, the frontal plane of the machining fixture 112 has member holes 116, suitable to hold the workpieces 117 with very tight tolerance, that is to say at least H6h5.

According to one possible operating mode, the frontal plane of the machining fixture 112 has a "stepped" profile to allow threading short through holes on the stepped lateral planes.

According to one possible operating mode, grub screws M2 fasten the workpieces 117 to the machining fixture 112 and guarantee a perfect electrical conductivity with said machining fixture 112, which fundamental for a successful EDM process.

According to one possible operating mode, the grub screws disappear under the plane to which they are screwed, i.e. are headless, to avoid limiting securing the fixture along those planes, with a vise of an EDM machine.

According to one possible operating mode, an alternative to the grub screws and to the threaded holes associated to the grub screws, is the use of conductive glue, to fasten the workpieces 117 to the machining fixture 112 and guarantee a perfect electrical conductivity with said machining fixture 112.

According to one possible operating mode, the arrangement of the workpieces 117 on the machining fixture 112 is such that they not overlap in the work planes, for example in the X-Y and Y-Z planes, such that different and independent details or profiles can be cut for each plane on each workpiece 117, by providing a single and continuous cutting profile 110 for the wire.

According to one possible operating mode, the gap, or non-overlapping section, between two adjacent workpieces is minimized such as to keep the dimensions of the machining fixture 112 as compact as possible. In this way it is possible to minimize the distance between the upper and lower guides, improving the machining precision.

According to one possible operating mode, a metallic reference rod 118 is inserted in the machining fixture 112 and is used for calibration of the EDM machine once the machining fixture 112 and the workpieces 117 are mounted on the machine.

According to one possible operating mode, a first calibration is provisioned, which is carried out only once for a given machining fixture 112, loaded with all the workpieces 117 and a given EDM machine being used for the machining. Said first calibration is capable to identify and compensate all errors related to the EDM machine and to the geometric errors of the machining fixture 112, such as for example those related to the relative position between the reference rod 118 and the workpieces 117.

According to one possible operating mode, once the positions of the workpieces 117 are defined with respect to the reference rod 118 in the various cutting planes, the cutting profiles 110 are generated, taking into account of any differences of the actual positions with the nominal ones.

According to one possible operating mode, said first calibration will be repeated only if the EDM machine is changed or a new machining fixture 112 is being used.

According to one possible operating mode, each time the machining fixture 112, loaded with the workpieces 117, is secured to the vise of the EDM machine before a cut, a second calibration procedure is foreseen, or a cut calibration, performed only on the calibration rod 118. This cut calibration process eliminates geometric offset and errors related to the manual fastening of the fixture and identifies the origin of the machine reference system with respect to the axis of the reference rod.

According to one possible operating mode, to allow the correct fastening of the machining fixture 112 to the vise of the EDM machine, said machining fixture 112 has at least a pair of fastening or fixing surfaces 113, 114, opposite and parallel to each other, and rectified, meant to be gripped by the jaws of the vise, and a flat posterior X-Z surface, rectified and orthogonal to the fixing surfaces 113, 114, meant to be flush with an reference surface of the machine, orthogonal to the vise's clamp.

According to one possible operating mode, by not using rotary table in the EDM machine, it is necessary that the machining fixture 112 have a pair of fixing surfaces 113, 114 that are flat, parallel and rectified, opposite to each other for each cut plane provisioned for the fabrication of the micro-components.

According to one possible operating mode, other cutting planes can be produced by appropriately modifying the machining fixture 112.

According to one possible operating mode, to machine in a third orthogonal plane, it is necessary to provision openings 125 in the machining fixture that allow the cutting wire 115 to be inserted on the inside of the machining fixture and hence avoid the cutting of portions of the machining fixture 112, for example. Several independent cutting profiles must be used however without requiring further calibrations. Nevertheless, at the end of every cutting profile 110 in said plane, the cutting wire 115 must be cut and reinserted in the next opening 125.

According to one possible operating mode, the fabrication process used for the fabrication of parts of a jointed device 70, provisions the insertion of four workpieces 117 composed of metallic cylinders made of tool steel, into member holes 116 on the front side of said machining fixture 112 and then their fastening with grub screws of M2 size.

According to one possible operating mode, all three-dimensional micro-part that form the jointed device 70 for micro-medical applications, are machined from metallic workpieces 117, in particular steel cylinders of 3 millimeter outer diameter and 12 millimeter length, that are machined by wire EDM on two planes, X-Y and Y-Z.

According to one possible operating mode, the machining fixture 112 loaded with the workpieces 117 is secured on the vise of the EDM machine by using the fixing surfaces 113, 114 as reference planes for the fastening and then the calibration in the X-Y plane is performed using the axis of the reference rod 118, rigidly attached to the machining fixture 112, as a reference. The first cutting profile 110 is performed, machining all the workpieces 117 fastened to the machining fixture 112, in the X-Y plane.

According to one possible operating mode, the machining fixture 112 is then removed from the machine and remounted, rotated by 90° to machine along said second plane Y-Z of the machining fixture 112.

According to one possible operating mode, a second calibration for the second work plane Y-Z is performed and then the cut of the second cut profile 210 is carried out.

According to one possible operating mode, by equipping the EDM machine with a rotating or orientable table, it is possible to perform the cut calibration process just once and rotate the work plane as necessary between one cut profile and the next.

According to one possible operating mode, at the end of the second cut profile 210 the components produced are completely detached from the workpiece and can be collected in the EDM machine bath.

Due to the provision of a robotic assembly, according to one embodiment it is possible to control the positioning and simultaneous motion of at least two jointed medical instruments, each comprising one jointed device operative within a workspace, in a reliable, precise and easily controllable manner, potentially reaching every body part of the patient with the terminal portions of said medical instruments.

The provision of a medical instrument comprising a jointed device moved by tendons according to one embodiment, reduces the complexity of its machining, for example by eliminating the provision of channels or sheaths, allowing extreme miniaturization of the medical instrument, without reducing its reliability during use or assembly.

Due to the provision of a jointed device according to one embodiment, comprising ruled surfaces with all parallel generatrices for the sliding of said tendons as well as tendon termination features arranged in a specific geometrical relationship to said surfaces, it is possible to do without tendon guide channels or sheaths, still guaranteeing parallelism of the tendons and hence allowing an extreme miniaturization of the jointed device.

Due to the provision of a fabrication method according to the invention, as well as a machining fixture, suitable to guarantee the simultaneous positioning of several workpieces in a manner that permits to their cutting lines to remain parallel to each other, it is possible to obtain a single cut path by a EDM cutting wire for each cutting plane, on a plurality of workpieces. In this way, it is possible to generate parallel surface on said pieces, with high tolerances, even in cases where very detailed, small shapes are machined.

Due to the provision of a fabrication method according to the invention, it is possible to produce micromechanical parts guaranteeing a high degree of precision as well as surfaces suitable for medical and/or surgical applications.

Due to the provision of a fabrication method, according to one aspect of the invention, it is possible to produce a medical instrument more rapidly with respect to known solutions, and as a consequence, more cost-efficiently.

Due to the provision of a machining fixture, as well as a fabrication method, according to one aspect of the invention, it is possible to obtain a fast and efficient process, even for repeated positioning of the workpieces within the machine.

Due to the provision of an improved machining fixture for EDM according to one aspect of the invention, which accelerates the cutting process on a plurality of cut planes, it is possible to reduce the number and duration of the phases dedicated to calibrating the machine.

Due to the provision of a fabrication method for electro-erosion according to one aspect of the invention, which permits the machining of micromechanical parts comprising cavities and ridges, that, even when leaving a groove between two prongs 81 of material, are suitable to form pin holding features without having to machine holes, it is possible to significantly reduce the machining time.

Due to the provision of a tendon 90 comprising a second tendon endpoint 92 as described above, it is possible to obtain a jointed device 70 in which its members do not require tendon guides or channels to facilitate the tendon 90 routing, without said tendons 90 interfering with each other. In fact, the geometric location of said tendon endpoints 92 is chosen in a way that said tendons 90 run substantially parallel to each other and parallel to said sliding surface 40, 80.

Due to the provision of a sliding surface, for example lateral sliding surfaces 40 and joint sliding surfaces 80, as previously described, it is possible to for said tendons to slide over the jointed device with low friction.

Due to the cooperation between said sliding surfaces 40, 80 and the geometric location of said first tendon endpoints 91 and said second tendon endpoints 92 it is possible to guarantee that the friction forces between the tendon and the sliding surface, as well as the fastening reactions at the first and second tendon endpoints 91 and 92 are substantially parallel to each other and along a same axis.

Due to cooperation between said sliding surfaces 40, 80 and the geometric location of said first tendon endpoints 91 and said second tendon endpoints 92, it is possible to obtain an extreme miniaturization of said medical instrument 60. For example, in this way it is possible to do without pulleys and/or other tendon guides, which are not suitable to be miniaturized beyond a certain threshold. For example, according to one embodiment, the shaft 65 of said medical instrument can measure 3 millimeter in outer diameter.

Due to the provision of a fabrication method based on EDM as previously described, it is possible to fabricate an entire jointed device with only one placement step in a machine, decreasing the fabrication time and cost, without decreasing the reliability or precision of machining.

Due to the provision of a fabrication method according to one embodiment, it is possible to produce joint members of a jointed device having ruled surfaces with parallel generatrices, such as to allow a tendon sliding over them maintain a stationary path with respect to said joint member. This allows the friction between the tendon and the sliding surface of the joint member to be reduced to a minimum, facilitating the miniaturization of the jointed device.

Due to the provision of a fabrication method based on EDM as previously described, suitable to transfer only thermal stimulation to the workpieces, it is possible to obtain parts of submillimeter dimensions, allowing an extreme miniaturization of said medical instrument 60, still maintaining a satisfying cut precision due to the provision of cutting on a plurality of workpieces in a single passing.

Due to the provision of a tool, as well as a method of EDM according to the invention, suitable for performing, with a single wire passing, the cut of parts in a plurality of workpieces which will be assembled together after machining, it is possible to obtain matings with millimetric precision, particularly suitable for building rotational joints features such as prongs, pivot holes, profiles of joint members, allowing hence to reliably mount pieces by snap-fit, or with controlled backlash between the same parts.

Although some combinations of embodiments described above can be seen in the attached figures, an expert of the field will also be able to configure combinations not shown in the figures, without departing from the scope of the following claims.

To satisfy specific and temporary needs, a person skilled in the art can carry out a number of modifications, adaptations and substitutions of elements with other functionally equivalent elements, without departing from the scope of the following claims.

REFERENCE LIST 7 work volume, or common workspace volume
9 tendon
16 point of intersection
18 proximal tendon portion
19 distal tendon portion
20 control device
21 control instrument
22 detection device
23 connection cable
24 communication and power cable
25 operator support surface
26 status signal light
27 operator support element
28 position sensor
29 tip sensor
30 macro-positioning arm
31 first arm member
32 second arm member
33 third arm member
34 fourth arm member
35 release button, or brake release button
36 linear sliding guide
37 manual knob
38 support member
39 attachment feature
40 sliding surface
41 micro-positioning device
43 rotation dial nut
45 video camera
46 motorized rotary joint
47 base portion
48 plunger locking hole
49 machining groove
50 tendon drive system
51 first motorized slide, or first motorized micro-slide
52 second motorized slide, or second motorized micro-slide
53 third motorized slide, or third motorized micro-slide
54 first slide rail
55 second slide rail
56 third slide rail
57 frame
58 first frame portion, or upper frame
59 second frame portion, drum, or lower frame
60 medical instrument or micro-instrument or surgical micro-instrument
61 motor box
62 mechanical transmission box
63 sharp edge of lateral sliding surface
64 continuity surface of lateral gliding surface
65 shaft, or hollow shaft
67 control device base structure
68 tip portion of control device
69 forceps articulation of control device
70 jointed or articulated device
71 first member or first joint member, or first link
72 second member or second joint member, or second link
73 third member or third joint member, or third link
74 fourth member or fourth joint member, or fourth link
75 elbow member, or elbow link
76 fastening pin
77 terminal device, or terminal member, or terminal portion
78 wrist member or wrist joint member
79 pin hole
80 sliding surface or joint sliding surface
81 prong
82 tendon termination feature, or tendon fastening point.
83 surface
84 tendon fastening surface
86 winding surface, or ruled winding surface
87 sterile barrier
88 shoulder surface
89 tendon guide element
90 tendon, or actuation cable, or tendon of a first pair of tendons
91 first endpoint or first tendon endpoint, or proximal tendon endpoint, or first tendon termination
92 second endpoint or second tendon endpoint, or distal tendon endpoint, or second tendon termination
93 tendon deflectable portion or deflectable portion
94 pusher assembly or pushing means
95 pushing element, piston, actuation piston or linear actuation piston.
96 plunger or sliding shaft
97 guiding elements, or tendon guiding elements, or guiding pulleys
98 plunger idle pulley
99 tensioning element, or oretensioning element, or spring
100 robotic assembly, or robotic surgical assembly, or surgical robotic assembly, robotic assembly for microsurgery or microsurgical robotic assembly
102 operating table
103 vision system, microscope, or surgical microscope
104 support or cart
105 foot platform
106 retractable handle
107 power cable
108 control panel
109 communication cable
110 cutting profile, or cutting line
111 display
112 machining fixture
113 first fixing surface of the first pair of fixing surfaces
114 second fixing surface of the first pair of fixing surfaces
115 cutting wire, or EDM wire, or electrical discharge machine wire
116 member holes or member seats
117 workpieces or pieces to be machined
118 reference rod
120 first control device
122 first rod portion
123 second rod portion
125 guide hole or opening 134 first fixing surface of the second pair of fixing surfaces
135 second fixing surface of the second pair of fixing surfaces
137 rotatary support table
141 first micro-positioning device
145 first portion of plunger
146 second portion of plunger
147 pushing surface
148 reciprocal pushing surface
150 sensor
151 force sensor
152 pressure sensor
153 proximity sensor
160 first medical instrument
170 first jointed device
171 rotational joint
172 jointing portion
173 spherical joint
177 first portion of terminal member
190 opposite tendon, or opposite tendon of a first pair of tendons
191 tendon of a second pair of tendons
192 opposite tendon of a second pair of tendons
194 opposite pusher assembly or opposite pushing means
197 first guiding element, or first guiding pulleys
199 opposite tensioning element, opposite pretensioning element, or opposite spring
210 second cut profile
220 second control device
221 second control instrument
241 second micro-positioning device
260 second medical instrument
270 second jointed device
277 second portion of terminal member
297 second tendon guiding element, or second tendon guiding pulley
397 third tendon guiding element, or third tendon guiding pulley.
497 fourth tendon guiding element, or fourth tendon guiding pulley.
200 surgeon, or microsurgeon
201 patient
202 surgical needle
341 third micro-positioning device
360 third medical instrument
T-T tendon direction or tendon path
X-X longitudinal shaft direction, or instrument axis
P-P pitch axis, or first axis of joint movement
Y-Y yaw axis, or second axis of joint movement
a-a first axis of arm movement
b-b second axis of arm movement
c-c third axis of arm movement
d-d fourth axis of arm movement
e-e longitudinal axis of base portion of macropositioning arm
f-f first slide direction
g-g second slide direction
h-h third slide direction
r-r longitudinal axis of rotation
X-Y first cutting plane
Y-Z second cutting plane
X-Z third cutting plane
R-R table axis of rotation, or fixture rotation axis
θ shaft angle

The invention claimed is:

1. A machining fixture for a wire electrical discharge machine having an electrical discharge wire, comprising a plurality of member holes, each member hole of said plurality of member holes being configured to accommodate a workpiece;
   wherein said machining fixture is configured to perform two cuts on each of plurality of workpieces accommodated in each of said plurality of member holes, said two cuts being performed in a first cutting plane and a second cutting plane; and
   wherein said plurality of member holes are sequentially arranged in an inclined plane so that when a translating straight line of said electrical discharge wire is substantially orthogonal to said first cutting plane, the translating straight line of said electrical discharge wire cuts no more than one workpiece of said plurality of workpieces in a first cutting direction, and when the translating straight line of said electrical discharge wire is substantially orthogonal to said second cutting plane, the translating straight line of said electrical discharge wire cuts no more than one workpiece of said plurality of workpieces in a second cutting direction when said plurality of workpieces are mounted in respective member holes of the plurality of member holes of the machining fixture.

2. The machining fixture according to claim 1, wherein said two cutting planes are mutually orthogonal.

3. The machining fixture according to claim 1, further comprising a reference rod for cut calibration.

4. The machining fixture according to claim 1, wherein each of the two cutting planes comprise two orthogonal axes, and wherein said two orthogonal axes intersect no more than one workpiece.

5. The machining fixture according to claim 1, wherein a frontal plane of the machining fixture has a stepped profile.

6. The machining fixture according to claim 1, comprising at least one fixing element to firmly connect said at least one workpiece in a respective member seat.

7. The machining fixture according to claim 1, comprising a first pair of precision finished fixing surfaces, the first pair of fixing surfaces being opposite and substantially parallel to each other and substantially orthogonal to a first cutting plane of said two cutting planes.

8. The machining fixture according to claim 7, comprising a second pair of precision finished fixing surfaces, the second pair of fixing surfaces being opposite and substantially parallel to each other and substantially orthogonal to a second cutting plane of said two cutting planes.

9. The machining fixture according to claim 1, wherein each member hole is substantially positioned at a same distance from a respective fastening surface of the fixture.

10. The machining fixture according to claim 9, wherein each fastening surface comprises a threaded hole for receiving a grub screw.

11. The machining fixture according to claim 9, wherein the fastening surfaces are arranged in a stepwise configuration having a ladder profile.

12. The machining fixture according to claim 1, wherein said plurality of member holes are parallel to one another.

13. The machining fixture according to claim 1, comprising a surface facing towards a cutting plane having an area less than 10000 square millimeters.

14. The machining fixture according to claim 1, comprising a surface facing towards a cutting plane having an area less than 5000 square millimeters.

15. The machining fixture according to claim 1, associated to a rotatable support table for rotating said fixture around a first fixture rotation axis parallel to a line of intersection of said first cutting plane and said second cutting plane.

\* \* \* \* \*